US006495562B1

(12) United States Patent
Bruncko et al.

(10) Patent No.: US 6,495,562 B1
(45) Date of Patent: Dec. 17, 2002

(54) NAPHTHAMIDINE UROKINASE INHIBITORS

(75) Inventors: Milan Bruncko, Lake Bluff; Christopher Robin Dalton, Mundelein; Vincent Louis Giranda; Jianchun Gong, both of Gurnee; Willian J. McClellan, Waukegan; Vicki L. Nienaber, Gurnee; Todd Warren Rockway, Grayslake, all of IL (US); Daryl Richard Sauer, Trevor, WI (US); Moshe Weitzberg, Highland Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/842,382

(22) Filed: Apr. 25, 2001

Related U.S. Application Data
(60) Provisional application No. 60/199,395, filed on Apr. 25, 2000.

(51) Int. Cl.⁷ ........................ C07D 213/02; A61K 41/47
(52) U.S. Cl. ........................................ 514/307; 546/147
(58) Field of Search ........................ 546/147; 514/307

(56) References Cited

U.S. PATENT DOCUMENTS

| 3,632,593 A | 1/1972 | Gautier et al. ............... 546/332 |
| 3,754,093 A | 8/1973 | Shigezane et al. .......... 514/637 |
| 3,919,225 A | 11/1975 | Arnold et al. ............... 544/242 |

FOREIGN PATENT DOCUMENTS

| AU | 7730198 | 2/1999 |
| EP | 0540051 | 5/1993 |
| EP | 0568289 | 11/1993 |
| EP | 5576343 | 11/1996 |
| JP | 6227971 | 8/1994 |
| WO | 9616940 | 6/1996 |
| WO | 9905096 | 2/1999 |
| WO | 9905124 | 4/1999 |

OTHER PUBLICATIONS

Alliegro, M.A. et al., "Inhibition of In Vitro Angiogenesis by Ami loride", *Journal of Cell Biology*, vol. 155 [3 pt 2], (1991), p. 402a.
Aoyama, T. et al., "Synthesis and Structure—Activity Study of Protease Inhibitors. IV. Amidinonaphthols and Related Acyl Derivatives", *Chemical and Pharmaceutical Bulletin*, vol. 33, No. 4 (1985), pp. 1458–1471.
Berge, S.M. et al., "Pharmaceutical Salts", *Journal of Pharmaceutical Sciences*, vol. 66, (1997), pp. 1–19.
Blasti, F. et al., "Urokinase–Type Plasminogen Activator: Proenzyme, Receptor, and Inhibitors", *Journal of Cell Biology*, vol. 104, (1987), pp. 801–804.
Dano, K. et al., *Advances in Cancer Research*, vol. 44, (1985), pp. 139–266.

Higuchi, T.et al., *Prodrugs as Novel Delivery Systems*, vol. 14, of A.C.S. Symposium series, 1980.
Katakura, S. et al., Molecul ar Model of an inteaction between factor Xa and DX –9095a, a novel factor Xa inhibitor: contribution of the acetimidoylpyrrolidine moiety of the inhibitor to potency and selectivity for serine proteases, *Eur. J. Med. Chem.*, vol. 30, No.5 (1995), pp387–396.
Kellen, J.A. et al., "Antimetastatic Effecy of Amiloride in an Animal Tumour Model", *Anticancer Research*, vol. 8 (1988), pp. 1373–1376.
Littlefield, B. A., "Plasminogen Activators in Endometrial Physiology and Embryo Implantaion: A Review", *Annals of the New York Academy of Sciences*, vol. 622 (1991), pp. 167–175.
Loozen, H.J.J. et al, "A Short Route to Functionalized Naphthalene", *Journal of Organic Chemistry*, vol. 40, No. 4 (1975), pp. 520–521.
Nagahara, T. et al., Dibasic (Amidinoar yl)propanoic Acid Derivatives as Novel Blood Coagulation Factor Xa Inhibitors, *Journal of Medicinal Chemistry*, vol. 37, No. 8 (Apr. 15, 1994), pp. 1200–1207.
Prescot, ed., *Methods in Cell Biology*, vol. XIV, Academic Press, New York, NY (1976), p. 33 et seq.
Roche, E.B. et al., Bioreversible Carriers in Drug Design: Theory and Application, American Pharmaceutical Association and Pergamon Press (1987).
Saksela, O. "Plasminogen Activation and Regulation of Pericellular Proteolysis", *Biochimica et Biophysica ACTA*, vol. 823, (1985), pp. 35–36.
Storzebecher, J. et al., Synthetische Inhibitoren der Serinproteinasen, *Pharmazie*, vol. 33, No.9 (1978), pp1599–602.
Teague, S.J. et al., "The Synthesis of Highly Functionalized Naphthalene Derivatives", *Synthesis*, vol. 5, (1986), pp. 427–429.
Testa, J.E. et al., "The Role of Urokinase–Type Plasminogen Activator in Aggressive Tumor Cell Behavior", *Cancer Metastasis Reviews*, vol. 9, (1990), pp. 353–367.

Primary Examiner—Zinna Northington Davis
(74) Attorney, Agent, or Firm—Gregory W. Steele; B. Gregory Donner

(57) ABSTRACT

Compounds having the formula

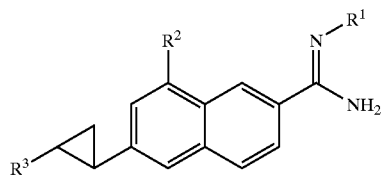

are inhibitors of urokinase and are useful in the treatment of diseases in which urokinase plays a role. Also disclosed are urokinase-inhibiting compositions, methods for the preparation of urokinase-inhibitors, and a method of inhibiting urokinase in a mammal.

18 Claims, No Drawings

NAPHTHAMIDINE UROKINASE INHIBITORS

CROSS-REFERENCE TO RELATED APPLICATIONS

This application claims benefit of the U.S. Provisional Patent Application Ser. No. 60/199,395, filed Apr. 25, 2000.

TECHNICAL FIELD

The instant invention provides naphthamidine compounds which inhibit urokinase, methods for making the compounds, pharmaceutical compositions containing the compounds, and methods of treatment using the compounds.

BACKGROUND OF THE INVENTION

Urokinase is a proteolytic enzyme which is highly specific for a single peptide bond in plasminogen. Plasminogen activation (cleavage of this bond by urokinase) results in formation of plasmin, a potent general protease.

Many cell types use urokinase as a key initiator of plasmin-mediated proteolytic degradation or modification of extracellular support structures such as extracellular matrix (ECM) and basement membrane (BM). Cells exist, move, and interact with each other in tissues and organs within the physical framework provided by ECM and BM. Movement of cells within ECM or across BM requires local proteolytic degradation or modification of the structures and allows cells to invade adjacent areas previously unavailable prior to the degradation or modification.

Cellular invasiveness initiated by urokinase is central to a variety of normal and disease-state physiological processes (*J. Cell Biol.* 1987, 104, 801–804 and *Adv. Cancer Res.* 1985, 44, 139–266). Such processes include angiogenesis, bone restructuring, embryo implantation in the uterus, infiltration of immune cells into inflammatory sites, ovulation, spermatogenesis, tissue remodeling during wound repair and organ differentiation, fibrosis, tumor invasion, metastatic spread of tumor cells from primary to secondary sites, and tissue destruction in arthritis. Amiloride, for example, a known urokinase inhibitor of only moderate potency, has been reported to inhibit tumor metastasis in vivo (*Anticancer Res.* 1988, 8, 1373–1376) and angiogenesis in vitro (*J. Cell Biol.* 1991, 115[3 Pt 2], 402a).

Inhibitors of urokinase, therefore, have mechanism-based anti-angiogenic, anti-arthritic, anti-inflammatory, anti-retinopathic (for angiogenesis-dependent retinopathies), contraceptive and tumoristatic uses.

SUMMARY OF THE INVENTION

In its principle embodiment, the instant invention provides a compound of formula (I)

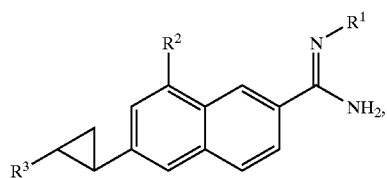

(I)

or a pharmaceutically acceptable salt thereof, wherein
$R^1$ is hydrogen or hydroxy;
$R^2$ is selected from the group consisting of hydrogen, halo, alkyl, alkenyl, alkynyl, alkoxyalkyl, heterocycloalkyl, aryl, heteroaryl, cycloalkyl, and —$NR^aR^b$, wherein $R^a$ and $R^b$ are independently selected from the group consisting of hydrogen, aryl, and heteroaryl; and $R^3$ is 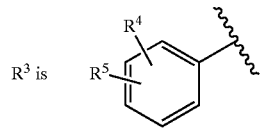

wherein $R^4$ and $R^5$ are on adjacent carbon atoms and, taken together with the carbon atoms to which they are attached, are pyridine or a nitrogen-containing heterocycloalkyl, wherein the groups defining $R^3$ can be optionally substituted with one, two, three, four, or five substituents independently selected from the group consisting of alkyl, cycloalkyl, (cycloalkyl)alkyl, hydroxy, hydroxyalkyl, aryl, arylalkyl, alkanoyl, alkoxycarbonyl, alkenyl, alkynyl, halo, haloalkyl, heteroaryl, heteroarylalkyl, and a nitrogen protecting group.

In another embodiment, the instant invention provides a pharmaceutical composition comprising a compound of formula (1), or a pharmaceutically acceptable salt thereof, in combination with a pharmaceutically acceptable carrier.

In another embodiment, the instant invention provides a method of inhibiting urokinase in a mammal in recognized need of such treatment comprising administering to the mammal a pharmaceutically acceptable amount of a compound of formula (I), or a pharmaceutically acceptable salt thereof.

In another embodiment, the instant invention provides a method for the preparation of a compound of formula (I), the method comprising:

(a) reacting a compound of formula (Ia)

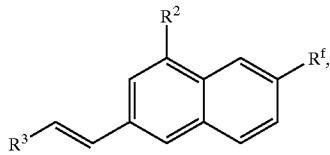

(Ia)

wherein $R^f$ is cyano or —$C(=NR^1)NH_2$ and wherein $R^2$ and $R^3$ are as previously defined, with diazomethane or trimethylsilyldiazomethane in the presence of a palladium catalyst;

(b) optionally reacting the product from step (a) with an anionic nitrogen source.

DETAILED DESCRIPTION OF THE INVENTION

Compounds of the instant invention comprise 6,8-disubstituted 2-naphthamidines which are useful for the treatment of urokinase-mediated diseases.

When used throughout this specification and the appended claims, the following terms have the meanings indicated:

The term "alkanoyl," as used herein, represents an alkyl group attached to the parent molecular moiety through a carbonyl group.

The term "alkenyl," as used herein, represents a monovalent straight or branched chain group of one to six carbon atoms containing at least one carbon-carbon double bond. The alkenyl groups of this invention can be optionally substituted with an alkoxy, amino, aryl, aryloxy, heteroaryl, heteroaryloxy, hydroxy, thioalkoxy, thioaryloxy, or thioheteroaryloxy substituent, wherein the aryl and the heteroaryl substituents can be further optionally substituted with one, two, or three substituents independently selected from the group consisting of alkyl, alkoxy, amino, halo, and cycloalkyl.

The term "alkoxy," as used herein, represents an alkyl group attached to the parent molecular moiety through an oxygen atom.

The term "alkoxyalkyl," as used herein, represents an alkoxy group attached to the parent molecular moiety through an alkyl group.

The term "alkoxycarbonyl," as used herein, represents an alkoxy group attached to the parent molecular moiety through a carbonyl group.

The term "alkyl," as used herein, represents a saturated straight or branched chain monovalent group of one to six carbon atoms derived from a hydrocarbon group. The alkyl groups of this invention can be optionally substituted.

The term "alkynyl," as used herein, represents a monovalent straight or branched chain group of one to six carbon atoms containing at least one carbon-carbon triple bond. The alkynyl groups of this invention can be optionally substituted with an alkoxy, amino, aryl, aryloxy, heteroaryl, heteroaryloxy, hydroxy, thioalkoxy, thioaryloxy, or thioheteroaryloxy substituent, wherein the aryl and the heteroaryl substituents can be further optionally substituted with one, two, or three substituents independently selected from the group consisting of alkyl, alkoxy, amino, halo, and cycloalkyl.

The term "amino," as used herein, represents —NR$^{10}$R$^{11}$ wherein R$^{10}$ and R$^{11}$ are independently selected from the group consisting of hydrogen, alkyl, aryl, heteroaryl, arylalkyl, cycloalkyl, and (cycloalkyl)alkyl; or R$^{10}$ and R$^{11}$, together with the nitrogen atom to which they are attached, form a ring selected from the group consisting of piperazinyl, morpholinyl, thiomorpholinyl, thiomorpholinyl dioxide, piperidinyl, and pyrrolidinyl.

The term "anionic nitrogen source," as used herein, represents lithium hexamethyldisilazide, potassium hexamethyldisilazide, or sodium hexamethyldisilazide.

The term "aryl," as used herein, represents phenyl, naphthyl, dihydronaphthyl, tetrahydronaphthyl, indanyl, and indenyl. Aryl groups having an unsaturated or partially saturated ring fused to an aromatic ring such as dihydronaphthyl, tetrahydronaphthyl, and indanyl can be attached through either the saturated or unsaturated part of the group. The aryl groups of this invention can be optionally substituted with one, two, three, four, or five substituents independently selected from the group consisting of alkanoyl, alkyl, alkoxy, alkoxyalkyl, cycloalkyl, (cycloalkyl)alkyl, perfluoroalkyl, hydroxy, hydroxyalkyl, halo, haloalkyl, nitro, alkoxycarbonyl, perfluoroalkoxy, and —NR$^c$R$^d$, wherein R$^c$ and R$^d$ are independently hydrogen or alkyl.

The term "arylalkyl," as used herein, represents an aryl group attached to the parent molecular moiety through an alkyl group.

The term "aryloxy," as used herein, represents an aryl group attached to the parent molecular moiety through an oxygen atom.

The term "cycloalkyl," as used herein, represents a saturated monovalent cyclic hydrocarbon.

The term "(cycloalkyl)alkyl," as used herein, represents a cycloalkyl group attached to the parent molecular moiety through an alkyl group.

The term "halo," as used herein, represents F, Cl, Br, and I.

The term "haloalkyl," as used herein, represents an alkyl group substituted by one, two, three, or four halogen atoms.

The term "heteroaryl," as used herein, represents a cyclic, aromatic group having five or six ring atoms, wherein at least one ring atom is selected from the group consisting of oxygen, sulfur, and nitrogen, and the remaining ring atoms are carbon. The five-membered rings have two double bonds and the six-membered rings have three double bonds. Heteroaryl groups of this invention include those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, thiene, triazole, and tetrazole by the removal of a hydrogen atom from a carbon atom in the ring. The term "heteroaryl" also includes bicyclic groups in which any of the above heteroaryl rings is fused to a phenyl ring. Examples of bicyclic heteroaryls include benzofuryl, benzothienyl, indolyl, isoquinolinyl, and quinolinyl, and the like. The heteroaryl groups of this invention can be optionally substituted with one, two, three, or four substituents independently selected from the group consisting of alkyl, cycloalkyl, (cycloalkyl)alkyl, hydroxy, hydroxyalkyl, aryl, arylalkyl, alkanoyl, alkoxycarbonyl, alkenyl, alkynyl, halo, haloalkyl, heteroaryl, heteroarylalkyl, a nitrogen protecting group, and —NR$^c$R$^d$, wherein R$^c$ and R$^d$ are as previously defined.

The term "heteroarylalkyl," as used herein, represents a heteroaryl group attached to the parent molecular moiety through an alkyl group.

The term "heteroaryloxy," as used herein, represents a heteroaryl group attached to the parent molecular moiety through an oxygen atom.

The term "heterocycloalkyl," as used herein, represents a non-aromatic five-, six- or seven-membered ring having between one and three heteroatoms independently selected from oxygen, sulfur, and nitrogen. The five-membered rings have zero to one double bond, the six-membered ring has zero to two double bonds, and the seven-membered ring has zero to three double bonds. Heterocycloalkyl groups of this invention include those derived from 1,2-dihydropyridinyl, 1,4-dihydropyridinyl, 3,4-dihydropyridinyl, 1,2,3,4-tetrahydropyridinyl, and piperidinyl by the removal of a hydrogen atom from a carbon atom in the ring. Heterocycloalkyl groups can also be fused to phenyl rings to provide bicyclic groups which can be attached to the parent molecular moiety through a carbon atom on either the phenyl part or the heterocycloalkyl part of the bicyclic group. Examples of these fused heterocycloalkyls include 1,2,3,4-tetrahydro-5-isoquinolinyl, 1,2,3,4-tetrahydro-6-isoquinolinyl, 1,2,3,4-tetrahydro-7-isoquinolinyl, 1,2,3,4-tetrahydro-8-isoquinolinyl, 3,4-dihydro-5-isoquinolinyl, 3,4-dihydro-6-isoquinolinyl, 3,4-dihydro-7-isoquinolinyl, 3,4-dihydro-8-isoquinolinyl, and the like. The heterocycloalkyl groups of this invention can be optionally substituted with one, two, three, or four substituents independently selected from the group consisting of alkyl, cycloalkyl, (cycloalkyl)alkyl, hydroxy, hydroxyalkyl, aryl, arylalkyl, alkanoyl, alkoxycarbonyl, alkenyl, alkynyl, halo, haloalkyl, heteroaryl, heteroarylalkyl, a nitrogen protecting group, and —NR$^c$R$^d$, wherein R$^c$ and R$^d$ are as previously defined.

The term "hydroxy," as used herein, represents —OH.

The term "hydroxyalkyl," as used herein, represents a hydroxy group attached to the parent molecular moiety through an alkyl group.

The term "nitro," as used herein, represents —NO$_2$.

The term "nitrogen-protecting group," as used herein, represents groups intended to protect an amino group against undesirable reactions during synthetic procedures. Common nitrogen-protecting groups comprise formyl, acetyl, propionyl, pivaloyl, tert-butylacetyl, 2-chloroacetyl, 2-bromoacetyl, trifluoroacetyl, trichloroacetyl, phthalyl, ortho-nitrophenoxyacetyl, α-chlorobutyryl, benzoyl, 4-chlorobenzoyl, 4-bromobenzoyl, 4-nitrobenzoyl, benzenesulfonyl, and para-toluenesulfonyl, benzyloxycarbonyl, para-chlorobenzyloxycarbonyl, para-methoxybenzyloxycarbonyl, tert-butyloxycarbonyl (Boc), benzyloxycarbonyl (Cbz), and the like.

The term "palladium catalyst," as used herein, refers to palladium complexes which enhance the rate of reactions. Examples of catalysts include palladium (II) acetate, palladium (II) chloride, and palladium (II) dibenzylideneacetone. Each of these catalysts can be used with triphenylphosphine, triphenylarsine, or a trialkylphosphine such as tributylphosphine optionally present.

The term "perfluoralkoxy," as used herein, represents a perfluoroalkyl group attached to the parent molecular moiety through an oxygen atom.

The term "perfluoroalkyl," as used herein, represents an alkyl group wherein each hydrogen radical bound to the alkyl group has been replaced by a fluoride radical.

The term "pharmaceutically acceptable salt," as use herein, represents those salts which are, within the scope of sound medical judgment, suitable for use in contact with the tissues of humans and lower animals without undue toxicity, irritation, allergic response and the like and are commensurate with a reasonable benefit/risk ratio. The salts can be prepared in situ during the final isolation and purification of the compounds of the instant invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to, ammonium, tetramethylammonium, tetraethylammonium, methylamine, dimethylamine, trimethylamine, triethylamine, ethylamine and the like.

The term "prodrug," as used herein, represents compounds that are rapidly transformed in vivo to yield the parent compounds of formula (I). such as, for example, by hydrolysis in blood. Prodrugs of these compounds include compounds of formula (I), wherein R$^1$ is hydroxy.

The term "thioalkoxy," as used herein, represents an alkyl group attached to the parent molecular moiety through a sulfur atom.

The term "thioaryloxy," as used herein, represents an aryl group attached to the parent molecular moiety through a sulfur atom.

The term "thioheteroaryloxy," as used herein, represents a heteroaryl group attached to the parent molecular moiety through a sulfur atom.

In accordance with methods of treatment and pharmaceutical compositions of the instant invention, the compounds can be administered alone or in combination with other inhibiting agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally adminstered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The inhibitory effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefor.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable nonirritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of the instant invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Preferred embodiments of the instant invention include, but are not limited to, compounds of formula (I) and formula (Ia), wherein $R^3$ is optionally substituted isoquinolinyl, optionally substituted 3,4-dihydro-6-isoquinolinyl, optionally substituted 3,4-dihydro-7-isoquinolinyl, optionally substituted 1,2,3,4-tetrahydro-6-isoquinolinyl, optionally substituted 1,2,3,4-tetrahydro-7-isoquinolinyl, or optionally substituted 3,4-dihydro-6-isoquinolinyl.

Specific compounds of the instant invention include, but are not limited to, 8-(3-furyl)-6-(2-(1-isopropyl-3,4-dihydro-7-isoquinolinyl) cyclopropyl)-2-naphthalenecarboximidamide,
6-(2-(1-isopropyl-7-isoquinolinyl)cyclopropyl)-2-naphthalenecarbonximidamide,
8-(3-furyl)-6-(2-(1-isopropyl-2-methyl-1,2,3,4-tetrahydro-7-isoquinolinyl)cyclopropyl)-2-naphthalenecarboximidamide,
6-(2-(1-isopropyl-3,4-dihydro-7-isoquinolinyl) cyclopropyl)-8-((1E)-3-methoxy-1-propenyl)-2-naphthalenecarboximidamide,
6-(2-(1-isopropyl-2-methyl-1,2,3,4-tetrahydro-7-isoquinolinyl)cyclopropyl-8-((1E)-3-methoxy-1-propenyl)-2-naphthalenecarboximidamide,
N'-hydroxy-6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide,
6-(2-(1-isopropyl-3,4-dihydro-7-isoquinolinyl) cyclopropyl)-8-tetrahydro-3-furanyl-2-naphthalenecarboximidamide,
6-(2-(1-isopropyl-3,4-dihydro-7-isoquinolinyl) cyclopropyl)-8-((1E)-3-methyl-1-butenyl)-2-naphthalenecarboximidamide,
6-(2-(1-cyclohexyl-3,4-dihydro-7-isoquinolinyl) cyclopropyl)-2-naphthalenecarboximidamide,
6-(2-(1-phenyl-3,4-dihydro-7-isoquinolinyl)cyclopropyl)-2-naphthalenecarboximidamide,
6-(2-(2-methyl-1-propyl-1,2,3,4-tetrahydro-7-isoquinolinyl)cyclopropyl)-2-naphthalenecarboximidamide,
6-(2-(1-cyclohexyl-2-methyl-1,2,3,4-tetrahydro-7-isoquinolinyl)cyclopropyl)-2-naphthalenecarboximidamide,
6-(2-(1-isopropyl-3,4-dihydro-7-isoquinolinyl) cyclopropyl)-2-naphthalenecarboximidamide,
6-(2-(2-acetyl-1-isopropyl-1,2,3,4-tetrahydro-7-isoquinolinyl)cyclopropyl)-2-naphthalenecarboximidamide,
6-(2-(1-isopropyl-2-methyl-1,2,3,4-tetrahydro-7-isoquinolinyl)cyclopropyl)-2-naphthalenecarboximidamide,
6-(2-(2-benzyl-1-isopropyl-1,2,3,4-tetrahydro-7-isoquinolinyl)cyclopropyl)-2-naphthalenecarboximidamide,
6-(2-(1-isopropyl-1,2,3,4-tetrahydro-7-isoquinolinyl) cyclopropyl)-2-naphthalenecarboximidamide,
6-(2-(1-isopropyl-2-(3-pyridinylmethyl)-1,2,3,4-tetrahydro-7-isoquinolinyl)cyclopropyl-2-naphthalenecarboximidamide,
6-(2-(2-cyclopropylmethyl)-1-isopropyl-1,2,3,4-tetrahydro-7-isoquinolinyl)cyclopropyl)-2-naphthalenecarboximidamide,
6-(2-(2-ethyl-1-isopropyl-1,2,3,4-tetrahydro-7-isoquinolinyl)cyclopropyl)-2-naphthalenecarboximidamide,
6-(2-(2-ally-1-1-isopropyl-1,2,3,4-tetrahydro-7-isoquinolinyl)cyclopropyl)-2-naphthalenecarboximidamide,
6-(2-(2-(2-hydroxyethyl)-1-isopropyl-1,2,3,4-tetrahydro-7-isoquinolinyl)cyclopropyl)-2-naphthalenecarboximidamide,
6-(2-(1,2-diisopropyl-1,2,3,4-tetrahydro-7-isoquinolinyl) cyclopropyl)-2-naphthalenecarboximidamide,
6-((1S,2S)-2-(1-isopropyl-3,4-dihydro-7-isoquinolinyl) cyclopropyl)-2-naphthalenecarboximidamide,
-((1R,2R)-2-(1-isopropyl-3,4-dihydro-7-isoquinolinyl) cyclopropyl)-2-naphthalenecarboximidamide,
6-(2-(4,4-diethyl-1-isopropyl-3,4-dihydro-6-isoquinolinyl) cyclopropyl)-2-naphthalenecarboximidamide,
6-(2-(4,4-diethyl-1-isopropyl-3,4-dihydro-6-isoquinolinyl) cyclopropyl)-2-naphthalenecarboximidamide,
6-(2-(4,4-diethyl-1-isopropyl-2-methyl-1,2,3,4-tetrahydro-6-isoquinolinyl)cyclopropyl)-2-naphthalenecarboximidamide,
6-(2-(1-isopropyl-2-(2,2,2-trifluoroethyl)-1,2,3,4-tetrahydro-7-isoquinolinyl)-2-naphthalenecarboximidamide, 8-((1E)-3,3-dimethyl-1-butenyl)-6-(2-(1-isopropyl-3,4-dihydro-7-isoquinolinyl)cyclopropyl)-2-naphthalenecarboximidamide, 8-bromo-6-(2-(1-isopropyl-3,4-dihydro-7-isoquinolinyl)cyclopropyl)-2-naphthalenecarboximidamide, 8-bromo-6-(2-(1-isopropyl-2-methyl-1,2,3,4-tetrahydro-7-isoquinolinyl)cyclopropyl)-2-naphthalenecarboximidamide, 6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide, 6-(2-(1-isopropyl-2-methyl-1,2,3,4-tetrahydro-7-isoquinolinyl)cyclopropyl)-8-((1E)-3-methyl-1,3-butanienyl)-2-naphthalenecarboximidamide, 8-cyclopropyl-6-(2-(1-isopropyl-2-methyl-1,2,3,4-tetrahydro-7-isoquinolinyl)cyclopropyl)-2-naphthalenecarboximidamide, 6-(2-(1-isopropyl-2-methyl-1,2,3,4-tetrahydro-7-isoquinolinyl)cyclopropyl)-8-(2-methoxyphenyl)-2-naphthalenecarboximidamide, 6-(2-(1-isopropyl-2-methyl-1,2,3,4-tetrahydro-7-isoqunolinyl)cyclopropyl)-8-vinyl-2-naphthalenecarboximidamide, 6-(2-(1,2,3,4-tetrahydro-6-isoquinolinyl)cyclopropyl)-2-naphthalenecarboximidamide, 6-(2-(2-acetyl-1,2,3,4-tetrahydro-6-isoquinolinyl)cyclopropyl)-N'-hydroxy-2-naphthalenecarboximidamide, 6-(2-(4-ethyl-1,2,3,4-tetrahydro-6-isoquinolinyl)cyclopropyl)-2-naphthalenecarboximidamide, 6-((2-(2-benzyl-4-ethyl-1,2,3,4-tetrahydro-6-isoquinolinyl)cyclopropyl)-2-naphthalenecarboximidamide, 6-(2-(4-ethyl-2-methyl-1,2,3,4-tetrahydro-6-isoquinolinyl)cyclopropyl)-2-naphthalenecarboximidamide, 6-(2-(1-isopropyl-3,4-dihydro-6-isoquinolinyl)cyclopropyl)-2-naphthalenecarboximidamide, 6-(2-(1-isopropyl-3,4-dihydro-6-isoquinolinyl)cyclopropyl)-2-naphthalenecarboximidamide, 6-(2-(4-ethyl-1-isopropyl-3,4-dihydro-6-isoquinolinyl)cyclopropyl)-2-naphthalenecarboximidamide, 8-bromo-6-(2-(1-cyclohexyl-3,4-dihydro-7-isoquinolinyl)cyclopropyl)-2-naphthalenecarboximidamide, 8-bromo-6-(2-(1-cyclohexyl-2-methyl-1,2,3,4-tetrahydro-7-isoquinolinyl)cyclopropyl)-2-naphthalenecarboximidamide, 6-(2-(1-cyclohexyl-3,4-dihydro-7-isoquinolinyl)cyclopropyl)-8-((1E)-3-methyl-1-butenyl)-2-naphthalenecarboximidamide, 6-(2-(1-cyclohexyl-2-methyl-1,2,3,4-tetrahydro-7-isoquinolinyl)cyclopropyl)-8-((1E)-3-methyl-1-butenyl)-2-naphthalenecarboximidamide, and 8-allyl-6-(2-(1-isopropyl-2-methyl-1,2,3,4-tetrahydro-7-isoquinolinyl)cyclopropyl)-2-naphthalenecarboximidamide.

Determination of Biological Activity

The efficacy of the compounds of the instant invention as urokinase inhibitors was determined by measuring the inhibition of the urokinase enzyme Abbokinase (Abbott Laboratories, Abbott Park, Ill.) on substrate S-2444 of formula pyroGlu-Arg-pNA-HCl (DiaPharma Group, Inc. Distributor of Chromogenix) at 200 $\mu$M.

The assay was performed in a 96 well polystyrene, flat bottom plate in a 50 mM Tris/0.15 M NaCl+0.5% Pluronic F-68 (Sigma P-5556), pH 7.4 with HCl buffer. The compounds of this invention, 10 mM in DMSO, were diluted with DMSO to eight half log concentrations, for example:

1200 $\mu$M, 400 $\mu$M, 120 $\mu$M, 40 $\mu$M, 12 $\mu$M, 4 $\mu$M, 1 $\mu$M and 0.4 $\mu$M. Four concentrations were chosen, then 5 $\mu$l of each were diluted to a total assay volume of 200 $\mu$L. The final compound concentrations in the assay, according to the above example, were 30 $\mu$M, 10 $\mu$M, 3 $\mu$M, 1 $\mu$M, 0.3 $\mu$M, 0.1 $\mu$M, 0.03 $\mu$M and 0.01 $\mu$M, respectively. The substrate S-2444 was used at 200 $\mu$M in the assay. Several vials were reconstituted as directed on the vial, aliquoted, and stored frozen The enzyme was further diluted in assay buffer and 10 $\mu$L was used in the assay. Enzyme concentration in the assay was 2–3 nM. The assay was performed as follows: 175 $\mu$L of buffer was pipetted into the polystyrene plate, and 5 $\mu$L solution of a compound of this invention in DMSO was added. The mixture was vortexed, treated with 10 $\mu$L of enzyme in buffer, vortexed, treated with 10 $\mu$L of substrate in water, and vortexed. The plate was placed in a Spectromax® (Molecular Devices Corporation, Sunnyvale, Calif.) plate reader to follow the course of the reaction for 15 minutes at 405 nm. The Spectromax® calculated the reaction rates which were used to calculate percent inhibition of the compounds of this invention versus the reaction rate of the enzyme in the absence of any inhibitor. The Ki's of the inhibitors were calculated from the percent inhibition and previously established Km. The compounds of this invention inhibit urokinase as shown by the data for representative examples in Table 1.

TABLE 1

Inhibitory Potency of Representative Compounds Against Urokinase

| Example | Ki ($\mu$M) | Example | Ki ($\mu$M) |
|---|---|---|---|
| 1 | 0.041 | 29 | 0.36 |
| 2 | 0.48 | 30 | 0.278 |
| 3 | 0.025 | 31 | 0.35 |
| 4 | 0.059 | 32 | 0.35 |
| 5 | 0.021 | 33 | 1.44 |
| 7 | 0.045 | 34 | 0.051 |
| 8 | 0.021 | 35 | 0.128 |
| 9 | 0.050 | 36 | 0.054 |
| 10 | 0.142 | 37 | 0.010 |
| 11 | 0.128 | 38 | 0.04 |
| 12 | 0.025 | 39 | 0.037 |
| 13 | 0.26 | 40 | 0.81 |
| 14 | 0.143 | 41 | 0.014 |
| 15 | 0.16 | 46 | 0.18 |
| 16 | 0.12 | 48 | 0.029 |
| 17 | 0.25 | 49 | 0.278 |
| 18 | 0.047 | 50 | 0.043 |
| 19 | 0.144 | 51 | 0.123 |
| 20 | 0.084 | 52 | 0.53 |
| 21 | 0.084 | 53 | 0.343 |
| 22 | 0.291 | 54 | 0.343 |
| 23 | 0.058 | 55 | 0.255 |
| 24 | 0.054 | 56 | 0.018 |
| 25 | 0.063 | 57 | 0.025 |
| 26 | 0.048 | 58 | 0.010 |
| 27 | 0.13 | 59 | 0.010 |
| 28 | 0.058 | 60 | 0.015 |

The pharmacokinetic behavior of selected compounds of formula (I) were evaluated in Sprague-Dawley rats and cynomolgus monkeys. In a series of parallel studies, group rats (n=3/group) and female cynomolgus monkeys (n=3/group) received a single 5 mg/kg IV or oral dose of selected compounds of formula (I). The compounds were prepared as solutions in either 0.2% hydroxpropyl methyl cellulose in water containing approximately 5% DMSO or in an ethanol:propylene glycol:D5W vehicle containing sodium hydroxide or hydrochloric acid (as needed for solubility) for both oral and IV dosing. All animals were fasted overnight prior to dosing and throughout the study. Water was provided freely. Sequential blood samples were obtained from each animal at selected time points after dosing. Plasma was separated by centrifugation at 4° C. and frozen until analysis. The parent drug was selectively removed from the plasma contaminants by liquid-liquid extraction with a mixture of ethyl acetate and hexanes under acidic conditions. The parent drug was separated from coextracted contaminants using reverse phase HPLC with MS quantitation of the analytes. The plasma concentrations of the representative compounds of formula (I) were plotted as plasma concentrations (μg/mL) versus time (hours after dosing) for both the IV and oral dosing, and areas under the curve (AUC's) were determined for each method of dosing. The data were normalized, and the fraction of drug available systemically (F) was determined for the representative compounds of formula (I) by dividing the AUC for the oral dosing by the AUC for the IV dosing. The representative compounds of formula (I) tested showed surprisingly high F values, indicating excellent systemic blood levels.

As shown by the good oral bioavailability and the high F value determined from the pharmacokinetic studies, the compounds of the instant invention, including, but not limited to, those specified in the examples, are useful for the treatment of disease caused or exasercbated by urokinase.

Synthetic Methods

Abbreviations which have been used in the descriptions of the scheme and the examples that follow are: THF for tetrahydrofuran; MTBE for methyl tert-butyl ether; LAH for lithium aluminum hydride; DMAP for 4-dimethylaminopyridine; DBU for 1,8-diazabicyclo[5.4.0]undec-7-ene; NBS for N-bromosuccinimide; DMF for N,N-dimethylformamide; NMP for N-methylpyrrolidinone; DME for 1,2-dimethoxyethane; LiHMDS for lithium hexamethyldisilazide; LDA for lithium diisopropylamine; KHMDS for potassium hexamethyldisilazide; NaHMDS for sodium hexamethyldisilazide, OAc for acetate; dba for dibenzylideneacetone; TFA for trifluoroacetic acid; and $BF_3 \cdot OEt_2$ for boron trifluoride etherate.

The compounds and processes of the instant invention will be better understood in connection with the following synthetic schemes which illustrate methods by which the compounds of the instant invention can be prepared. The compounds can be prepared by a variety of synthetic routes. Representative procedures are shown in Schemes 1–7. The groups $R^1$, $R^2$, $R^3$, $R^4$, and $R^5$ are defined above. It will be readily apparent to one of ordinary skill in the art that the compounds can be synthesized by substitution of the appropriate reactants and agents in the syntheses shown below.

Scheme 1

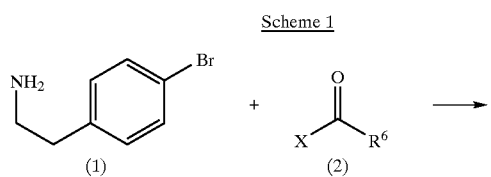

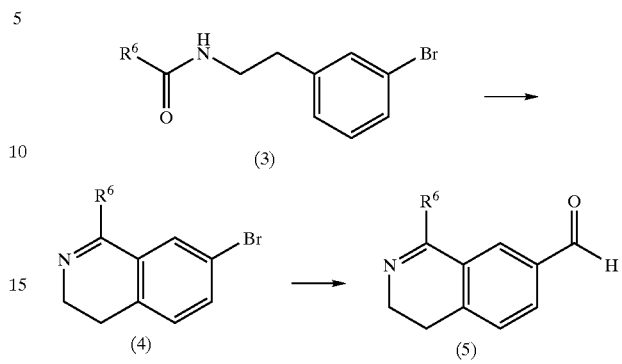

As shown in Scheme 1, compounds of formula (1) can be condensed with compounds of formula (2) (X is OAc or Cl) in the presence of base to provide compounds of formula (3). Representative bases include triethylamine, DMAP, pyridine, and 2,6-lutidine. Examples of solvents used in these reactions include dichloromethane, 1,2-dichloroethane, carbon tetrachloride, chloroform. The reaction temperature is about 10° C. to about 40° C. and depends on the method chosen. Reaction times are typically about 1 to about 12 hours. In a preferred embodiment, compounds of formula (1) in dichloromethane at room temperature are treated with compounds of formula (2), triethylamine, and DMAP, and stirred for 3 hours to provide compounds of formula (3).

Compounds of formula (3) can be converted to compounds of formula (4) by treatment with oxalyl chloride in the presence of ferrous (III) chloride, and treatment of the resulting product with sulfuric acid. Examples of solvents used in these reactions include dichloromethane, 1,2-dichloroethane, carbon tetrachloride, and chloroform. Reaction temperatures are about −78° C. to about 70° C., and reaction times are typically about 1 to about 48 hours.

Conversion of compounds of formula (4) to compounds of formula (5) can be accomplished by treatment with a formylating agent. Representative formylating agents include CO/catalytic palladium, butyllithium/N,N-dimethylformamide, butyllithium/N-formylmorpholine, and butyllithium/N-formylpiperidine. Examples of solvents used in these reactions include THF, dioxane, diethyl ether, and MTBE. The reaction temperature is about −78° C. to about 50° C. and depends on the method chosen. Reaction times are about 0.5 to about 12 hours. In a preferred embodiment, compounds of formula (3) in THF at −78° C. are treated with butyllithium and N-formylmorpholine, warmed to room temperature, and stirred for 15 minutes to provide compounds of formula (5).

Scheme 2

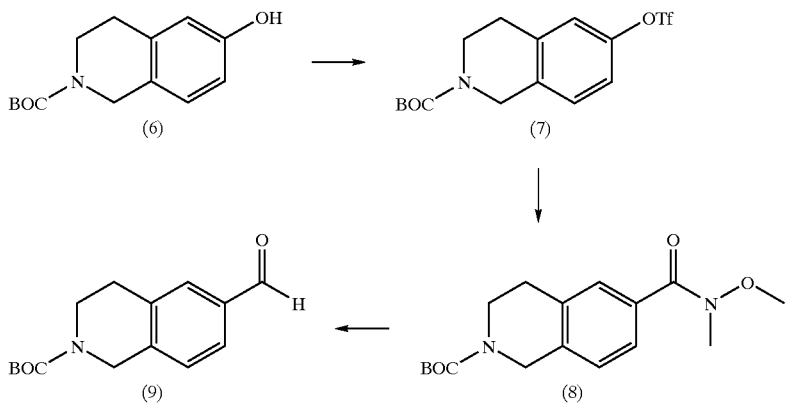

As shown in Scheme 2, compounds of formula (6) can be converted to compounds of formula (7) by treatment with trifluormethanesulfonic anhydride in the presence of base. Representative bases include triethylamine, diisopropylethylamine, pyridine, and 2,6-lutidine. Examples of solvents used in these reactions include dichloromethane, 1,2-dichloroethane, carbon tetrachloride, and chloroform. The reaction temperature is about −10° C. to about 35° C. and depends on the method chosen. Reaction times are typically about 2 to about 48 hours. In a preferred embodiment, compounds of formula (6) in dichloromethane at 0° C. are treated with trifluoromethanesulfonic anhydride in the presence of triethylamine, warmed to room temperature, and stirred for 48 hours to provide compounds of formula (7).

Conversion of compounds of formula (7) to compounds of formula (8) can be accomplished by treatment with carbon monoxide in the presence of catalytic palladium, water, and base, followed by treatment with N,O-dimethylhydroxylamine hydrochloride in the presence of an activating agent and base. Representative palladium catalysts include $PdCl_2(dppf)$, $PdCl_2(PPh_3)_2$, and $Pd(OAc)_2$, and representative bases include triethylamine, diisopropylethylamine, pyridine, and 2,6-lutidine. Examples of activating agents used in these reactions include (O-(-7-azabenzotriazol-1-yl)-N,N,N',N'-tetramethyluronium hexafluorophosphate, O-benzotriazol-1-yl-N,N,N',N'-tetramethyluronium hexafluorophosphate, and O-benzotriazol-1-yl-N,N,N',N'-tetramethyluronium tetrafluoroborate. Representative solvents include THF, MTBE, diethyl ether, and 1,2-dimethoxyethane. The reaction temperature is about 20° C. to about 125° C. and depends on the method chosen. Reaction times are typically about 12 to about 48 hours. In a preferred embodiment, compounds of formula (7) in THF and water are treated with triethylamine and $PdCl_2(dppf)$, heated to 115° C., stirred under 400 psi of carbon monoxide for 18 hours, cooled to room temperature, filtered, treated with diisopropylethylamine, N,O-dimethylhydroxylamine hydrochloride, and (O-(7-azabenzotriazol-1-yl)—N,N,N',N'-tetramethyluronium hexafluorophoshphate, and stirred for 16 hours to provide compounds of formula (8).

Compounds of formula (8) can be converted to compounds of formula (9) by treatment with a reducing agent. Representative reducing agents include LAH, sodium triacetoxyborohydride, lithium tri-tert-butoxyaluminohydride, and diisobutylaluminum hydride. Examples of solvents used in these reactions include THF, 1,2-dimethoxyethane, MTBE, and diethyl ether. The reaction temperature is about −10° C. to about 25° C. and depends on the method chosen. Reaction times are typically about 0.5 to about 12 hours. In a preferred embodiment, compounds of formula (8) in THF at 0° C. are treated with LAH and stirred for 30 minutes to provide compounds of formula (9).

Scheme 3

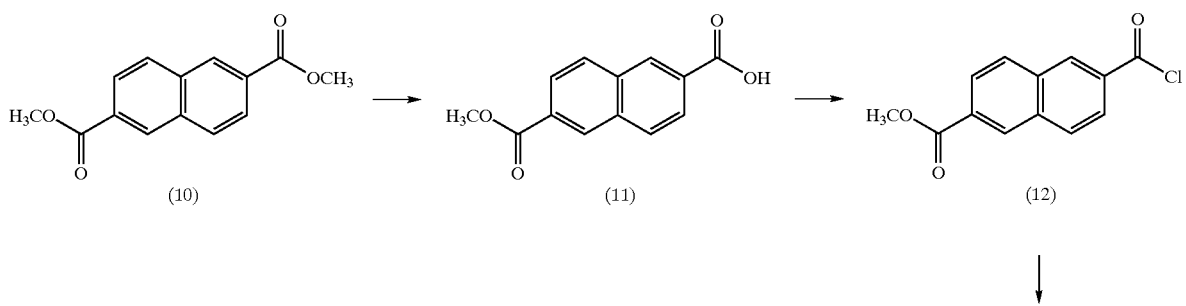

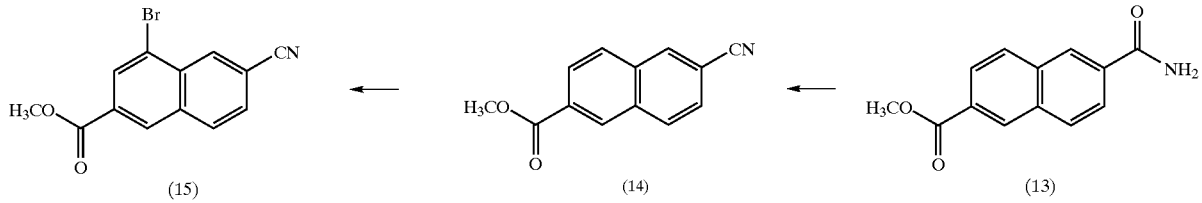

As shown in Scheme 3, compounds of formula (10) can be converted to compounds of formula (11) by treatment with base. Representative bases include potassium hydroxide, lithium hydroxide, and sodium hydroxide. Examples of solvents used in these reactions include methanol, ethanol, water, dioxane, and mixtures thereof. The reaction temperature is about 25° C. to about 110° C. and depends on the method chosen. Reaction times are typically about 0.5 to about 12 hours. In a preferred embodiment, compounds of formula (10) in dioxane are treated with potassium hydroxide in methanol, heated to 70° C., and stirred for 30 minutes to provide compounds of formula (11).

Conversion of compounds of formula (11) to compounds of formula (12) can be accomplished by treatment with a chlorinating agent in the presence of catalytic base. Representative chlorinating agents include $SOCl_2$, $PCl_5$, and $PPh_3/CCl_4$. Examples of bases used in these reactions include DMAP, DBU, and 2,6-lutidine. Representative solvents include toluene, hexanes, benzene, and mesitylene. The reaction temperature is about 25 to about 100° C. and depends on the method chosen. Reaction times are typically about 0.5 to about 12 hours. In a preferred embodiment, compounds of formula (11) in toluene are treated with thionyl chloride and DMAP, heated to reflux for 1 hour, cooled to 85° C., and stirred for 0.5 hours to provide compounds of formula (12).

Compounds of formula (12) can be converted to compounds of formula (13) by treatment with ammonia. Examples of solvents used in this reaction include dichloromethane, carbon tetrachloride, 1,2-dichloroethane, and chloroform. The reaction temperature is about 20° C. to about 45° C. and depends on the method chosen. Reaction times are typically about 10 minutes to about 1 hour. In a preferred embodiment, compounds of formula (12) in dichloromethane at room temperature are treated with dry ammonia gas for 15 minutes to provide compounds of formula (13).

Conversion of compounds of formula (13) to compounds of formula (14) can be accomplished by treatment with a dehydrating reagent. Representative dehydrating reagents include triphosgene, phosgene, $SOCl_2$, and $P_2O_5$. Examples of solvents used in these reactions include, trimethylphosphite, DMF, pyridine, and mixtures thereof. The reaction temperature is about 25° C. to about 100° C. and depends on the method chosen. Reaction times are typically about 0.5 to about 12 hours. In a preferred embodiment, compounds of formula (13) in trimethylphosphite at room temperature are treated with triphosgene, stirred for 20 minutes, heated to 80° C., and stirred for 1 hour to provide compounds of formula (14).

Compounds of formula (14) can be converted to compounds of formula (15) by treatment with a brominating agent. Representative brominating agents include NBS, dibromodimethylhydantoin/trifluoromethanesulfonic acid, $Br_2$, and HOBr. Examples of solvents used in these reactions include dichloromethane, carbon tetrachloride, chloroform, and 1,2-dichloroethane. The reaction temperature is about 25° C. to about 50° C. and depends on the method chosen. Reaction times are typically about 1 to about 36 hours. In a preferred embodiment, compounds of formula (14) in dichloromethane at room temperatue are treated with dibromodimethylhydantoin and trifluoromethanesulfonic acid and stirred for 18 hours to provide compounds of formula (15).

Scheme 4

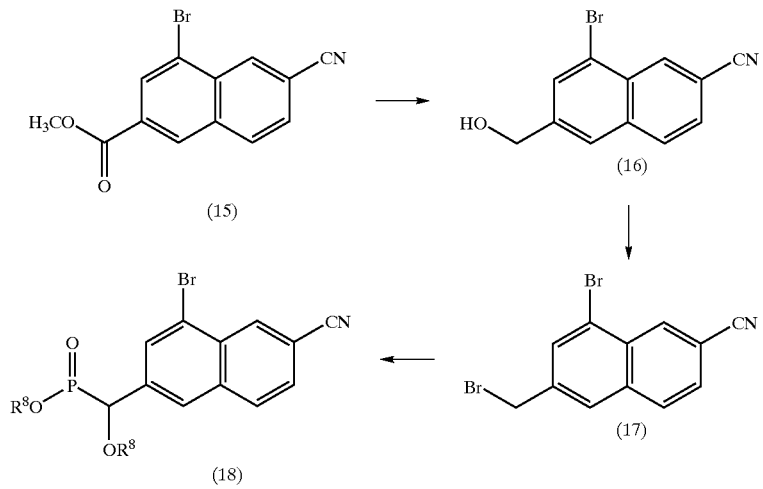

As shown in Scheme 4, compounds of formula (15) can be converted to compounds of formula (16) by treatment with a reducing agent. Representative reducing agents include borane/pyrrolidine complex, LAH, diisobutylaluminium hydride, $CaBH_4$, and lithium tri-tert-butoxyaluminum hydride. Examples of solvents used in these reactions include THF, pentane, MTBE, diethyl ether, and mixtures thereof. The reaction temperature is about −10° C. to about 30° C. and depends on the method chosen. Reaction times are typically about 0.5 to about 12 hours. In a preferred embodiment, compounds of formula (15) at 0° C. are treated with a solution of borane/pyrrolidine in THF and pentane, stirred for 15 minutes, warmed to room temperature, and stirred for 5 hours to provide compounds of formula (16).

Conversion of compounds of formula (16) to compounds of formula (17) can be accomplished by treatment with a brominating agent. Representative brominating agents include $NBS/PPh_3$, $LiBr/PBr_3$, $Br_2/PPh_3$, and $CBr_4/PPh_3$. Examples of solvents used in these reactions include dichloromethane, 1,2-dichloroethane, and THF. The reaction temperature is about 0° C. to about 35° C. and depends on the method chosen. Reaction times are typically about 8 to about 24 hours. In a preferred embodiment, compounds of formula (16) are treated with $PPh_3$ and NBS, warmed to room temperature, and stirred for 16 hours to provide compounds of formula (17).

Compounds of formula (17) can be converted to compounds of formula (18) by treatment with a trialkylphosphite. Representative trialkylphosphites include trimethylphosphite and triethylphosphite. Examples of solvents used in these reactions include DMF, NMP, dioxane, and DME. The reaction temperature is about about 80° C. to about 160° C. and depends on the method chosen. Reaction times are typically about 1 to about 12 hours. In a preferred embodiment, compounds of formula (17) in DMF are treated with triethylphospite, heated to 155° C., and stirred for 3 hours to provide compounds of formula (18).

As shown in Scheme 5, compounds of formula (18) can be condensed with compounds of formula (5) (synthesized in Scheme 1) or with compounds of formula (9) (synthesized in Scheme 2) in the presence of base to provide compounds of formula (19). Representative bases include LiHMDS, LDA, KHMDS, and butyllithium. Examples of solvents used in these reactions include THF, DME, diethyl ether, and MTBE. The reaction temperature is about 0° C. to about 25° C., and depends on the method chosen. Reaction times are typically about 0.5 to about 12 hours. In a preferred embodiment, compounds of formula (18) in THF at 5° C. are treated with LiHMDS, stirred for 30 minutes, treated with compounds of formula (5) or compounds of formula (9), warmed to room temperature, and stirred for 16 hours to provide compounds of formula (19).

Compounds of formula (20) can be prepared by the cross-coupling of compounds of formula (19) with an appropriately substituted organometallic reagent ($R^2$—M) in the presence of a catalyst. Representative coupling partners include organoboranes, organomagenesium halides, and organostannanes. Examples of catalysts used in these reactions include $Pd(PPh_3)_4$, $PdCl_2(PPh_3)_2$, and $Pd(OAc)_2$. Solvents used in these reactions include THF, NMP, DMF, and acetonitrile. The reaction temperature is about 25° C. to about 100° C. and depends on the method chosen. Reaction times are typically about 1 to about 24 hours.

Compounds of formula (20) can be converted to compounds of formula (21) by treatment with diazomethane or trimethylsilyldiazomethane in the presence of a palladium catalyst. Representative palladium catalysts include $Pd(OAc)_2$, $PdCl_2$, and $Pd_2(dba)_3$. Examples of solvents used in these reactions include THF, diethyl ether, and MTBE. The reaction temperature is about −10° C. to about 25° C. and depends on the method chosen. Reaction times are typically about 30 minutes to about 1 hour. In a preferred embodiment, compounds of formula (20) in THF are treated with diazomethane and $Pd(OAc)_2$ and stirred for 20 minutes to provide compounds of formula (21).

Scheme 5

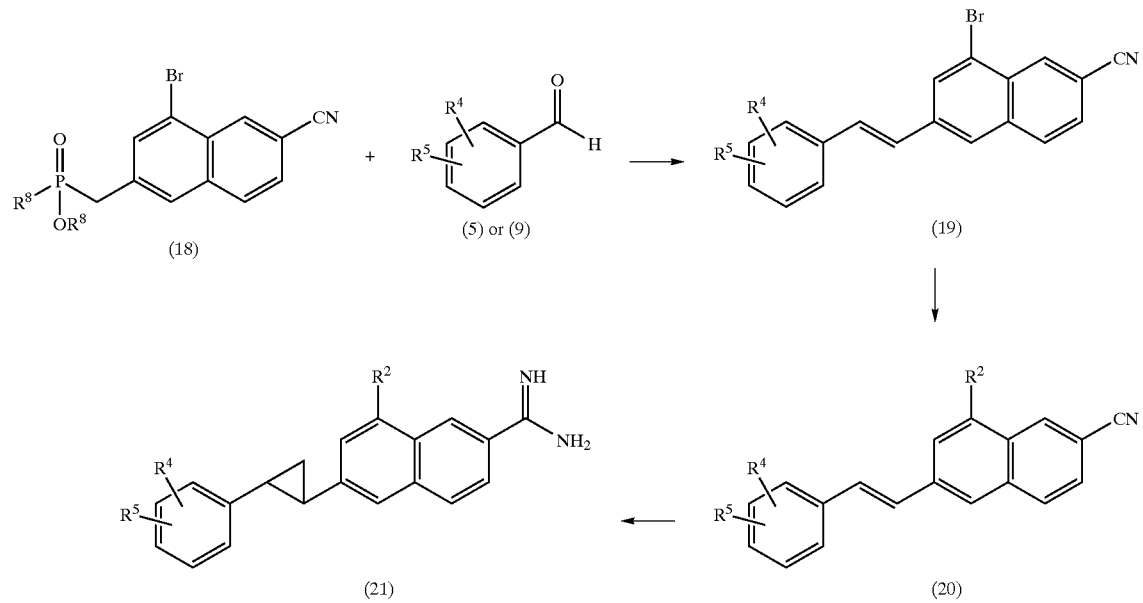

Scheme 6

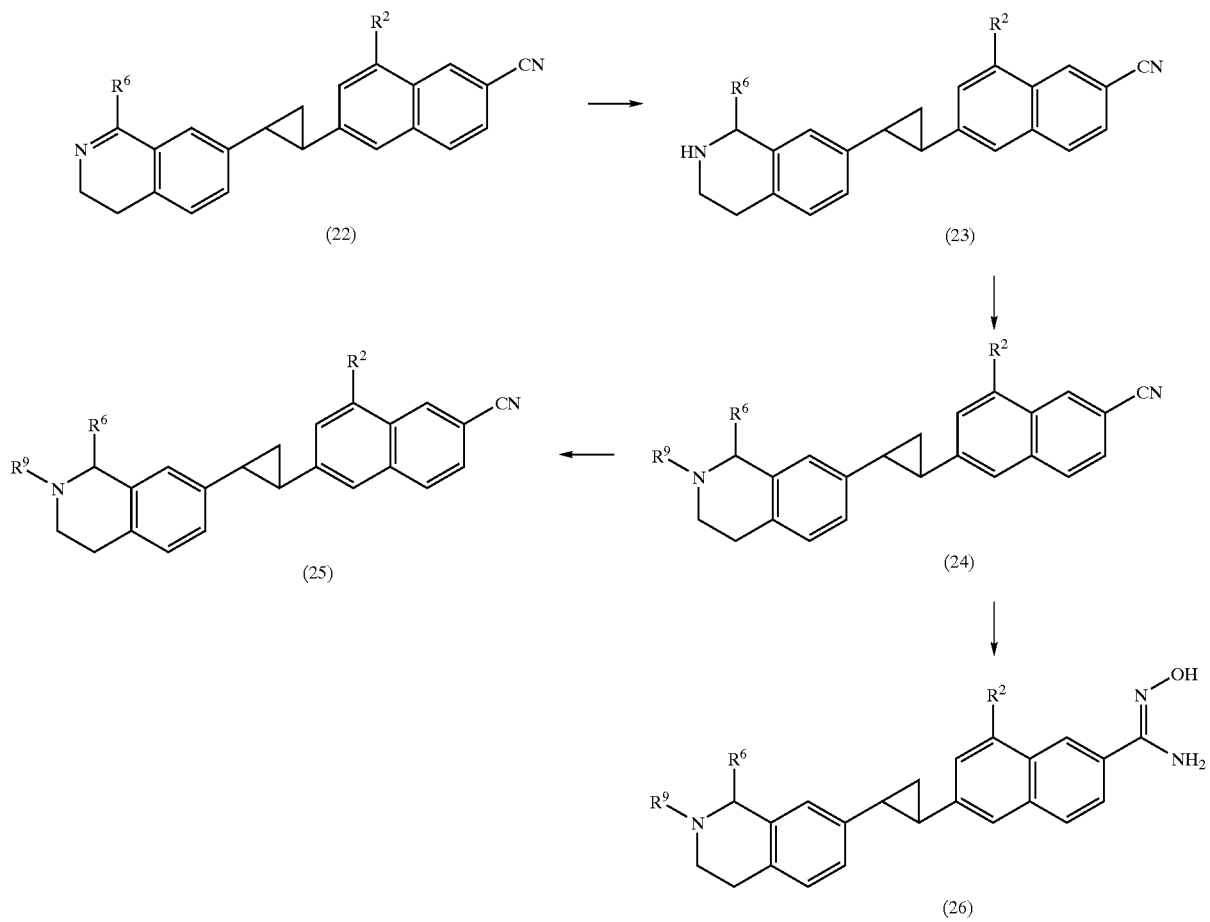

As shown in Scheme 6, compounds of formula (22) can be converted to compounds of formula (23) by treatment with a reducing agent. Representative reducing agents include diisobutylaluminum hydride, sodium borohydride, and sodium triacetoxyborohydride. Examples of solvents used in these reactions include methanol, ethanol, isopropanol, and n-propanol. The reaction temperature is about 20° C. to about 40° C. and depends on the method chosen. Reaction times are typically about 0.5 to about 6 hours. In a preferred embodiment, compounds of formula (22) in methanol at room temperature are treated with sodium borohydride and stirred for 30 minutes to provide compounds of formula (23).

Conversion of compounds of formula (23) to compound of formula (24) can be accomplished by treatment with an appropriately substituted aldehyde in the presence of a reducing agent ($R^9$ is alkyl), or by treatment with an acylating agent in the presence of base ($R^9$ is acyl). Representative reducing agents include sodium triacetoxyborohydride and sodium cyanoborohydride, while representative bases include potassium carbonate, sodium carbonate, and sodium bicarbonate. Examples of solvents used in these reactions include dichloromethane, dioxane, chloroform, and THF. The reaction temperature is about –10° C. to about 35° C. and depends on the method chosen. Reaction times are typically about 2 to about 36 hours.

Compounds of formula (24) can be converted to compounds of formula (25) by treatment with an anionic nitrogen source such as lithium hexamethyldisilazide, potassium hexamethyldisilazide, or sodium hexamethyldisilazide followed by treatement with acid. Representative acids include HCl, $H_2SO_4$, and $HNO_3$. Examples of solvents used in this reaction include THF, hexanes, MTBE, diethyl ether, and mixtures thereof. The reaction temperature is about –10° C. to about 35° C. and depends on the method chosen. Reaction times are typically about 1 to about 36 hours. In a preferred embodiment, compounds of formula (24) in THF at 0° C. are treated with lithium hexamethyldisilazide in hexanes, warmed to room temperature, stirred for 18 hours, treated with 10% HCl, and stirred for 24 hours to provide compounds of formula (25).

Compounds of formula (24) can also be converted to compounds of formula (26) by treatment with hydroxylamine. Examples of solvents used in this reaction include ethanol, methanol, and isopropanol. The reaction temperature is about 25° C. to about 100° C. and depends on the method chosen. Reaction times are typically about 1 to about 12 hours. In a preferred embodiment, compounds of formula (24) in ethanol are treated with hydroxylamine hydrochloride and triethylamine, heated to 80° C., and stirred for 2.5 hours to provide compounds of formula (26).

Scheme 7

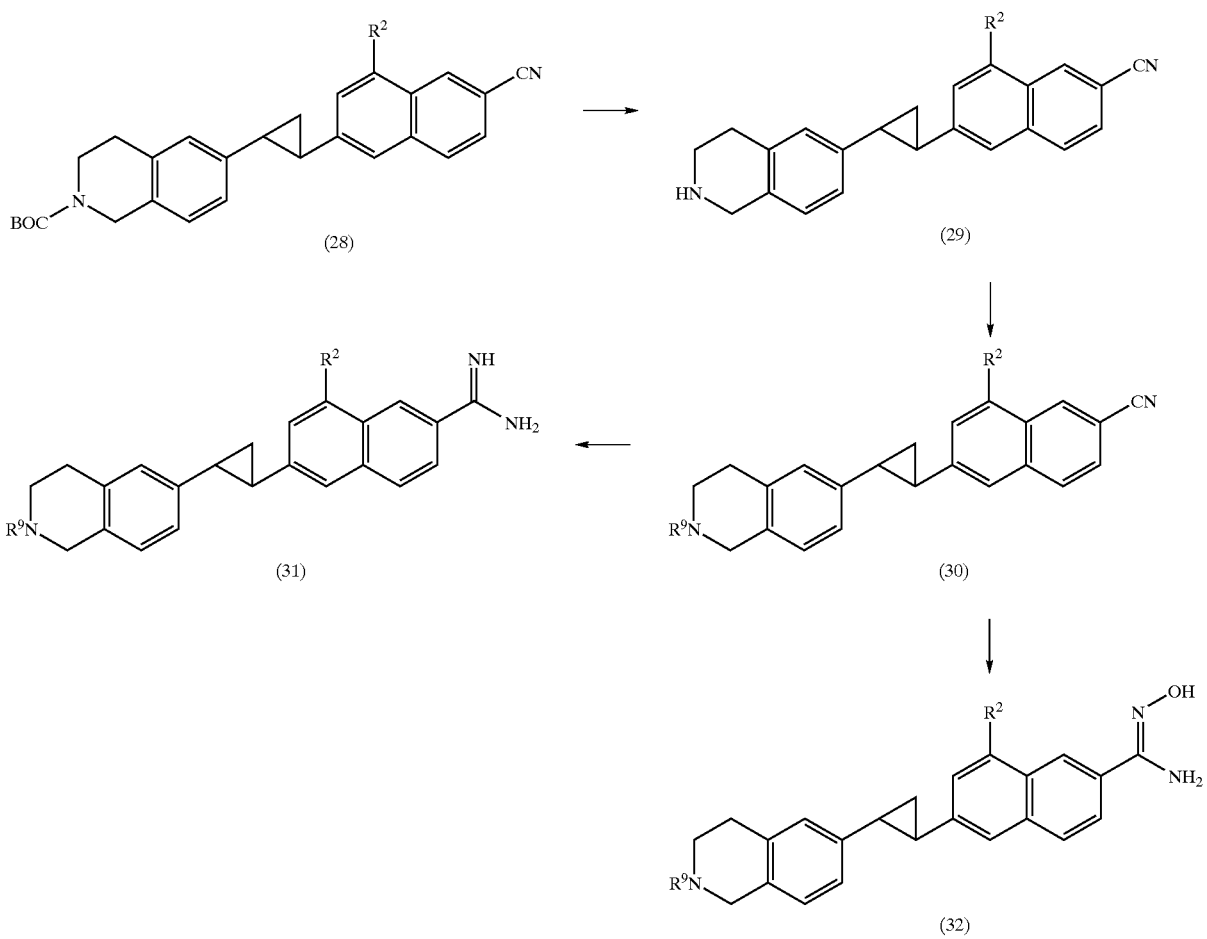

As shown in Scheme 7, compounds of formula (28) can be subjected to deprotection conditions to provide compounds of formula (29). Representative deprotection conditions include HCl, TFA, trimethylsilyliodide, and aluminum trichloride. Examples of solvents used in these reactions include dichloromethane, chloroform, water, THF, and mixtures thereof. The reaction temperature is about 0° C. to about 50° C. and depends on the method chosen. Reaction times are typically about 0.5 to about 12 hours. In a preferred embodiment, compounds of formula (28) in dichloromethane at room temperature are treated with trifluoroacetic acid and stirred for 1 hour to provide compounds of formula (29).

Compounds of formula (29) can be converted to compounds of formula (30) and subsequently to compounds of formula (31) or (32) following the procedures described in Scheme 6.

The instant invention will now be described in connection with certain preferred embodiments which are not intended to limit its scope. On the contrary, the instant invention covers all alternatives, modifications, and equivalents as can be included within the scope of the claims. Thus, the following examples, which include preferred embodiments, will illustrate the preferred practice of the instant invention, it being understood that the examples are for the purposes of illustration of certain preferred embodiments and are presented to provide what is believed to be the most useful and readily understood description of its procedures and conceptual aspects.

EXAMPLE 1

8-(3-furyl)-6-(2-(1-isopropyl-3,4-dihydro-7-isoquinolinyl)cyclopropyl)-2-naphthalenecarboximidamide

EXAMPLE 1A 6-(methoxycarbonyl)-2-naphthoic acid

A solution of dimethyl 2,6-naphthalenedicarboxylate (39.6 g, 162 mmol) in dioxane (1.2 L) was heated to 70–80° C., slowly treated with a solution of KOH (9.1 g, 162 mmol) in methanol (162 mL), heated to 70° C., stirred for 30 minutes, cooled to room temperature, and filtered. The solid was washed sequentially with dioxane and diethyl ether, dissolved in water, adjusted to pH<7 with 1M HCl, and filtered. The solid was washed with water and dried to provide the desired product.

MS (DCl/NH$_3$) m/e 231 (M+H)$^+$.

EXAMPLE 1B methyl 6-(chlorocarbonyl)-2-naphthoate

A suspension of Example 1A (15.0 g, 65.0 mmol) in toluene (190 mL) was treated with thionyl chloride (20 mL, 276 mmol) and DMAP (15 mg), heated to reflux for 1 hour, cooled to 85° C., and stirred for 35 minutes. The mixture was distilled to remove 60 mL of solvent, cooled to room temperature, triturated with hexanes, and filtered to provide the desired product.

MS (DCI/NH$_3$) m/e 249 (M+H)$^+$.

EXAMPLE 1C methyl 6-(aminocarbonyl)-2-naphthoate

A solution of Example 1B (15.0 g, 60.3 mmol) in dichloromethane (400 mL) at room temperature was treated with dry ammonia gas and stirred for 15 minutes. The resulting precipitate was collected by filtration, washed with water, and dried to provide the desired product.

MS (DCI/NH$_3$) m/e 230 (M+H)$^+$.

EXAMPLE 1D methyl 6-cyano-2-naphthoate

A suspension of Example 1C (31.0 g, 135 mmol) in trimethylphosphite (450 mL) at room temperature was treated with triphosgene (27.0 g, 136 mmol), stirred for 20 minutes, heated to 80° C., stirred for 1 hour, and cooled to room temperature. The resulting slurry was treated with water and filtered. The solid was washed with water and dried to provide the desired product.

MS (DCI/NH$_3$) m/e 212 (M+H)$^+$.

EXAMPLE 1E methyl 4-bromo-6-cyano-2-naphthoate

A solution of Example 1D (5.50 g, 26.0 mmol) in dichloromethane (125 mL) at room temperature was treated with dibromodimethylhydantoin (4.47 g, 15.6 mmol) and trifluoromethanesulfonic acid (2.51 mL, 28.4 mmol), stirred in darkness for 18 hours, and poured into saturated NaHSO$_3$. The mixture was adjusted to pH>7 with Na$_2$CO$_3$, and extracted with ethyl acetate. The combined extracts were washed with brine, dried (Na$_2$SO$_4$), filtered, and concentrated. The concentrate was recrystallized from ethanol/ethyl acetate to provide the desired product.

MS (DCI/NH$_3$) m/e 307 (M+NH$_4$)$^+$.

EXAMPLE 1F 8-bromo-6-(hydroxymethyl)-2-naphthonitrile

A solution of pyrrolidine (0.747 g, 10.5 mmol) in THF (20 mL) at 5° C. was treated with 1M BH$_3$ in THF (10.5 mL, 10.5 mmol), stirred for 1 hour, treated with 2M n-butyllithium in pentane (5.25 mmol, 10.5 mmol), stirred for 30 minutes, and warmed to room temperature over 30 minutes. The solution was cooled to 0° C., treated with Example 1E (2.90 g, 10.0 mmol), stirred for 15 minutes, warmed to room temperature, and stirred for 5 hours. The mixture was cooled to 0° C. and treated slowly with 2M HCl (27 mL). The aqueous phase was extracted with dichloromethane, and the combined extracts were washed with water and brine, dried (MgSO$_4$), filtered, and concentrated to provide the desired product of sufficient purity for subsequent use without further purification.

MS (DCI/NH$_3$) m/e 279 (M+NH$_4$)$^+$;
$^1$H NMR (300 MHz, DMSO-d$_6$) δ8.55 (s, 1H), 8.19 (d, 1H), 8.03 (s, 1H), 7.99 (d, 1H), 7.90 (dd, 1H), 5.58 (t, 1H), 4.72 (d, 2H).

EXAMPLE 1G 8-bromo-6-(bromomethyl)-2-naphthonitrile

A suspension of Example 1F (2.13 g, 8.16 mmol) and triphenylphosphine (2.15 g, 8.13 mmol) in dichloromethane (40 mL) at 0° C. was treated in small portions with NBS (1.45 g, 8.13 mmol), warmed to room temperature, and stirred for 16 hours. The mixture was washed with saturated NaHCO$_3$, dried (MgSO$_4$), filtered, and concentrated. The concentrate was dissolved in dichloromethane and passed through a pad of silica gel to provide the desired product.

MS (DCI/NH$_3$) m/e 341 (M+NH$_4$)$^+$;
$^1$H NMR (300 MHz, DMSO-d$_6$) δ8.58 (s, 1H), 8.21 (d, 1H), 8.20 (s, 1H), 8.13 (d, 1H), 7.95 (dd, 1H), 4.90 (s, 1H).

EXAMPLE 1H diethyl(4-bromo-6-cyano-2-naphthyl) methylphosphonate

A suspension of Example 1G (0.43 g, 1.31 mmol) and triethylphosphite (0.34 mL, 2.0 mmol) in DMF (2 mL) was heated to 155° C., stirred for 3 hours, and concentrated to provide the desired product of sufficient purity for subsequent use without further purification.

MS (DCI/NH$_3$) m/e 399 (M+NH$_4$)$^+$;
$^1$H NMR (300 MHz, DMSO-d$_6$) δ8.55 (s, 1H), 8.17 (d, 1H), 8.00 (s, 1H), 7.99 (s, 1H), 7.91 (dd, 1H), 3.99 (sext, 4H), 3.51 (d, 2H), 1.18 (t, 6H).

EXAMPLE 1I 7-bromo-1-isopropyl-3,4-dihydroisoquinoline

The desired product was prepared from 2-(4-bromophenyl)ethylamine and 2-methylpropanoyl chloride according to the procedure described in *J. Org. Chem.* 1991, 56, 6034.

MS (ESI(+)) m/e 252 (M+H)$^+$.

EXAMPLE 1J 1-isopropyl-3,4-dihydro-7-isoquinolinecarbaldehyde

A solution of Example 1I (4.7 g, 18.7 mmol) in THF (80 mL) at −78° C. was treated dropwise with 2.5M n-butyllithium in hexanes (9.0 mL, 22.4 mmol), stirred for 20 minutes, treated dropwise with DMF (2.2 mL, 28.0 mmol), stirred for 20 minutes, quenched with saturated NH$_4$Cl, warmed to room temperature, and extracted with diethyl ether. The combined extracts were washed with brine, dried (MgSO$_4$), filtered, and concentrated to provide the desired product.

MS (DCI/NH$_3$) m/e 202 (M+H)$^+$.

EXAMPLE 1K 8-bromo-6-(2-(1-isopropyl-3,4-dihydro-7-isoquinolinyl)ethenyl)-2-naphthonitrile A solution of Example 1H (3.82 g, 10 mmol) in THF (20 mL) at 5° C. was treated dropwise with 1M LiHMDS in hexanes (11 mL, 11 mmol), stirred for 30 minutes, and treated with Example 1J. The mixture was warmed to room temperature over 16 hours, treated with 2M HCl (20 mL), and extracted with dichloromethane. The combined extracts were washed with water and saturated NaHCO$_3$, dried (MgSO$_4$), filtered, and concentrated. The concentrate was dissolved in dichloromethane, filtered through a pad of silica gel, concentrated, and recrystallized from ethyl acetate to provide the desired product.

EXAMPLE 1L 8-(3-furyl)-6-(2-(1-isopropyl-3,4-dihydro-7-isoquinolinyl)ethenyl)-2-naphthonitrile The desired product was prepared from Example 1K and tributyl(3-furyl)stannane according to the procedure described in *J. Am. Chem. Soc.* 1987, 109, 5478–5486

MS (DCI/NH$_3$) m/e 417 (M+H)$^+$. .

EXAMPLE 1M

8-(3-furyl)-6-(2-(1-isopropyl-3,4-dihydro-7-isoquinolinyl)cyclopropyl)-2-naphthonitrile A solution of Example 1L (0.4 g, 1.0 mmol) in THF (10 mL) was added dropwise to diazomethane (10 mL) at 0° C., treated with Pd(OAc)$_2$ (15 mg), stirred 20 minutes, filtered, and concentrated to provide the desired product.

MS (DCI/NH$_3$) m/e 431 (M+H)$^+$.

EXAMPLE 1N

8-(3-furyl)-6-(2-(1-isopropyl-3,4-dihydro-7-isoquinolinyl)cyclopropyl)-2-naphthalenecarboximidamide A solution of Example 1M (0.4 g, 1.0 mmol) in THF (20 mL) at 0° C. was treated with 1.0M LiHMDS in hexanes (5.0 mL, 5.0 mmol), warmed to room temperature, stirred for 18 hours, treated with 10% HCl (20 mL), stirred for 24 hours, and concentrated. The concentrate was purified by preparative reverse-phase HPLC using 10% to 90% acetonitrile/water/0.1% TFA to provide the desired product.

MS (DCI/NH$_3$) m/e 448 (M+H)$^+$;

$^1$H NMR (300 MHz, DMSO-d$_6$) δ9.41 (br s, 3H), 9.27 (br s, 2H), 8.53 (s, 1H), 8.26 (s, 1H), 8.11 (d, 1H), 7.99 (s, 1H), 7.92 (t, 1H), 7.86 (s, 1H), 7.80 (dd, 1H), 7.64 (dd, 1H), 7.51–7.46 (m, 2H), 7.08–7.05 (m, 1H), 3.90 (hept, 1H), 3.83 (t, 2H), 3.06 (t, 2H), 2.67–2.54 (m, 2H), 1.85–1.72 (m, 2H), 1.33 (t, 6H);

Anal. calcd. for C$_{30}$H$_{29}$N$_3$O.2.5CF$_3$CO$_2$H: C, 57.38; H, 4.33; N, 5.74; F, 19.45. Found C, 57.14; H, 4.28; N, 5.78; F, 19.21.

EXAMPLE 2

6-(2-(1-isopropyl-7-isoquinolinyl)cyclopropyl)-2-naphthalenecarboximidamide

EXAMPLE 2A

6-(2-(1-isopropyl-7-isoquinolinyl)cyclopropyl)-2-naphthonitrile

A suspension of Example 14A (74.0 mg, 0.20 mmol) and 10% Pd/C (7.6 mg) in decalin (5 mL) was heated to 180° C., stirred for 2 hours, and concentrated. The concentrate was purified by flash chromatography on silica gel using dichloromethane then 60% ethyl acetate/hexanes to provide the desired product.

EXAMPLE 2B

6-(2-(1-isopropyl-7-isoquinolinyl)cyclopropyl)-2-naphthalenecarboximidamide

The desired product was prepared by substituting Example 2A for Example 1M in Example 1N.

MS (DCI/NH$_3$) m/e 380 (M+H)$^+$;

$^1$H NMR (300 MHz, DMSO-d$_6$) δ9.05 (br s, 2H), 8.45 (m, 1H), 8.42 (d, 1 H), 8.33 (br s, 1H), 8.07 (s, 2H), 8.05 (s, 2H), 7.94–7.86 (m, 1 H), 7.92 (s, 1H), 7.80 (dd, 1H), 7.79–7.74 (m, 1H), 7.57 (dd, 1H), 4.22–4.12 (m, 1H), 2.78–2.66 (m, 2H), 1.93–1.81 (m, 2H), 1.40 (t, 6H), 9.41 (br s, 2H);

Anal. calcd. for C$_{26}$H$_{25}$N$_3$.2.5CF$_3$CO$_2$H: C, 56.03; H, 4.17; N, 6.32. Found: C, 56.04; H, 4.12; N, 6.40.

EXAMPLE 3

8-(3-furyl)-6-(2-(1-isopropyl-2-methyl-1,2,3,4-tetrahydro-7-isoquinolinyl)cyclopropyl)-2-naphthalenecarboximidamide

EXAMPLE 3A

8-(3-furyl)-6-(2-(1-isopropyl-2-methyl-1,2,3,4-tetrahydro-7-isoquinolinyl)cyclopropyl)-2-naphthonitrile The desired product was prepared by substituting Example 1M for Example 31F in Example 32A.

MS (DCI/NH$_3$) m/e 447 (M+H)$^+$.

EXAMPLE 3B

8-(3-furyl)-6-(2-(1-isopropyl-2-methyl-1,2,3,4-tetrahydro-7-isoquinolinyl)cyclopropyl)-2-naphthalenecarboximidamide The desired product was prepared by substituting Example 3A for Example 1M in Example 1N.

MS (DCI/NH$_3$) m/e 464 (M+H)$^+$;

$^1$H NMR (300 MHz, DMSO-d$_6$) δ9.39 (br s, 3H), 9.11 (br s, 2H), 8.52 (s, 1H), 8.26 (m, 1H), 8.10 (dd, 1H), 7.92 (t, 1H), 7.84 (s, 1H), 7.79 (d, 1H), 7.49 (s, 1H), 7.25–7.18 (m, 2H), 7.08–7.03 (m, 2H), 4.23–4.16 (m, 1H), 3.75–3.61 (m, 2H), 3.33–3.21 (m, 1H), 3.04–2.98 (m, 2H), 2.83 (m, 3H), 2.53–2.32 (m, 1H), 2.20–2.10 (m, 1H), 1.70–1.50 (m, 2H), 1.10 (t, 3H), 0.84 (t, 3H);

Anal. calcd. for C$_{31}$H$_{33}$N$_3$O.2.6CF$_3$CO$_2$H: C, 57.20; H, 4.72; N, 5.53. Found: C, 57.26; H, 4.91; N, 5.33.

EXAMPLE 4

6-(2-(1-isopropyl-3,4-dihydro-7-isoquinolinyl)cyclopropyl)-8-(3-methoxy-1-propenyl)-2-naphthalenecarboximidamide

EXAMPLE 4A

8-bromo-6-(2-(1-isopropyl-3,4-dihydro-7-isoquinolinyl)cyclopropyl)-2-naphthonitrile The desired product was prepared by substituting Example 1K for Example 1L in Example 1M.

MS (DCI/NH$_3$) m/e 445 (M+H)$^+$.

EXAMPLE 4B

2-(3-methoxy-1-propenyl)-4,4,5,5-tetramethyl-1,3,2-dioxaborolane

The desired product was prepared from 3-methoxy-1-propyne according to the procedure described in *Tetrahedron Lett.* 1995, 36, 5665–5668.

EXAMPLE 4C

6-(2-(1-isopropyl-3,4-dihydro-7-isoquinolinyl)cyclopropyl)-8-(3-methoxy-1-propenyl)-2-naphthonitrile A solution of Example 4A (0.4 g, 1.0 mmol) and Example 4B (0.2 g, 1.0 mmol) in THF was treated with PdCl$_2$(PPh$_3$)$_2$ (35 mg, 0.05 mmol), heated to 57° C., and treated with 1M LiOH (2 mL, 2.0 mmol). The reaction was stirred for 3 hours, cooled to room temperature, treated with 2M HCl (20 mL), and stirred for 30 minutes. The mixture was diluted with dichloromethane, washed with water and brine, dried ($Na_2SO_4$), filtered, and concentrated. The concentrate was purified by flash column chromatography on silica gel with 25% ethyl acetate/hexanes to provide the desired product.

MS (APCI(+)) m/e 435 (M+H)$^+$.

EXAMPLE 4D 6-(2-(1-isopropyl-3,4-dihydro-7-isoquinolinyl)cyclopropyl)-8-(3-methoxy-1-propenyl)-2-naphthalenecarboximidamide Example 4C was processed as described in Example 1N, then purified by reverse phase HPLC using 10% to 90% methanol/water/0.1% TFA to provide the desired product.

MS (APCI(+)) m/e 452 (M+H)$^+$;

$^1$H NMR (300 MHz, $CD_3OD$) δ8.65 (s, 1H), 8.05–8.03 (m, 2H), 7.80–7.74 (m, 3H), 7.63 (br s, 3H), 7.48 (d, 1H), 7.37–7.27 (m, 4H), 6.47 (dt, 1H), 4.25 (dd, 1H), 3.66–3.48 (m, 2H), 3.31–3.29 (m, 6H), 2.78–2.75 (m, 2H), 2.49–2.45 (m, 2H), 1.74–1.65 (m, 2H), 1.25 (dd, 6H).

EXAMPLE 5

6-(2-(1-isopropyl-2-methyl-1,2,3,4-tetrahydro-7-isoquinolinyl)cyclopropyl)-8-((1E)-3-methoxy-1-propenyl)-2-naphthalenecarboximidamide

EXAMPLE 5A 6-(2-(1-isopropyl-2-methyl-1,2,3,4-tetrahydro-7-isoquinolinyl)cyclopropyl)-8-((1E)-3-methoxy-1-propenyl)-2-naphthonitrile The desired product was prepared by substituting Example 4C for Example 31F in Example 32A.

MS (APCI(+)) m/e 451 (M+H)$^+$.

EXAMPLE 5B 6-(2-(1-isopropyl-2-methyl-1,2,3,4-tetrahydro-7-isoquinolinyl)cyclopropyl)-8-((1E)-3-methoxy-1-propenyl)-2-naphthalenecarboximidamide The desired product was prepared by substituting Example 5A for Example 1M in Example 1N.

MS (APCI(+)) m/e 468 (M+H)$^+$;

$^1$H NMR (300 MHz, $CD_3OD$) δ8.65 (s, 1H), 8.05–8.03 (m, 2H), 7.80–7.72 (m, 4H), 7.61 (s, 1H), 7.50 (d, 1H), 7.23 (br s, 4H), 7.06–7.05 (m, 1H), 6.47 (dt, 1H), 4.25 (dd, 1H), 3.76–3.68 (m, 1H), 3.31–3.29 (m, 9H), 3.12–3.08 (m, 2H), 2.88 (br s, 2H), 2.45–2.40 (m, 2H), 2.22–2.17 (m, 1H), 1.72–1.57 (m, 2H), 1.20 (dd, 2H), 0.93 (dd, 2H).

EXAMPLE 6

N'-hydroxy-6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide The desired product was prepared by substituting Example 37B for Example 42K in Example 42L.

MS (APCI(+)) m/e 482 (M+H)$^+$;

$^1$H NMR (300 MHz, $CD_3OD$) δ8.51 (s, 1H), 8.02 (d, 1H), 7.68–7.65 (m, 2H), 7.53 (s, 1H), 7.25–7.06 (m, 4H), 6.39–6.31 (m, 1H), 4.22 (dd, 1H), 3.83–3.76 (m, 1H), 3.31–3.29 (m, 3H), 3.13 (dd, 2H), 2.97–2.93 (m, 3H), 2.68–2.61 (m, 1H), 2.43–2.36 (m, 2H), 2.21–2.18 (m, 1H), 1.72–1.55 (m, 2H), 1.27–1.15 (m, 9H), 0.96 (dd, 3H).

EXAMPLE 7

6-(2-(1-isopropyl-3,4-dihydro-7-isoquinolinyl)cyclopropyl)-8-tetrahydro-3-furanyl-2-naphthalenecarboximidamide

EXAMPLE 7A 8-(3-hydroxy-1-(hydroxymethyl)propyl)-6-(2-(1-isopropyl-3,4-dihydro-7-isoquinolinyl)ethenyl)-2-naphthonitrile A solution of Example 1K (3.09 g, 10 mmol) in N-methylpyrrolidinone (10 mL) was treated with $PdCl_2$ (120 mg, 1 mmol), cis-2-butene-1,4-diol (1.23 mL, 15 mmol) and $NaHCO_3$ (1.01 g, 12 mmol), heated to 130° C., stirred for 1 hour, cooled to room temperature, and purified by flash column chromatography on silica gel with 30% ethyl acetate/hexanes to provide the desired product.

EXAMPLE 7B 6-(2-(1-isopropyl-3,4-dihydro-7-isoquinolinyl)ethenyl)-8-tetrahydro-3-furanyl-2-naphthonitrile A solution of Example 7A (140 mg, 0.52 mmol) in dichloromethane (3 mL) at 0° C. was treated with triethylsilane (0.166 mL, 1.04 mmol) and $BF_3.OEt_2$ (0.096 mL, 0.78 mmol), warmed to room temperature, stirred for 4 hours, and concentrated. The concentrate was purified by flash column chromatography on silica gel with 25% ethyl acetate/hexanes to provide the desired product.

MS (APCI(+)) m/e 421 (M+H)$^+$.

EXAMPLE 7C 6-(2-(1-isopropyl-3,4-dihydro-7-isoquinolinyl)cyclopropyl)-8-tetrahydro-3-furanyl-2-naphthonitrile The desired product was prepared by substituting Example 7B for Example 1L in Example 1M.

MS (APCI(+)) m/e 435 (M+H)$^+$.

EXAMPLE 7D 6-(2-(1-isopropyl-3,4-dihydro-7-isoquinolinyl)cyclopropyl)-8-tetrahydro-3-furanyl-2-naphthalenecarboximidamide The desired product was prepared by substituting Example 7C for Example 1M in Example 1N.

MS (APCI(+)) m/e 452 (M+H)$^+$;

$^1$H NMR (300 MHz, DMSO-$d_6$) δ9.51 (s, 2H), 9.15 (s, 2H), 8.70 (s, 1H), 8.05 (d, 1H), 7.97 (s, 1H), 7.85 (dd, 1H), 7.71 (s, 1H), 7.62 (m, 1H), 7.47 (m, 2H), 4.32 (m, 1H), 4.21 (m, 1H), 4.04 (m, 1H), 3.90 (m, 2H), 3.79 (m, 2H), 3.05 (t, 2H), 2.56 (t, 2H), 2.13 (m, 1H), 1.75 (m, 2H), 1.34 (t, 6H);

Anal. calcd. for $C_{30}H_{33}N_3O.1.4HCl$: C, 62.60; H, 6.37; N, 7.30. Found: C, 62.42; H, 6.72; N, 6.94.

EXAMPLE 8

6-(2-(1-isopropyl-3,4-dihydro-7-isoquinolinyl)cyclopropyl)-8-((1E)-3-methyl-1-butenyl)-2-naphthalenecarboximidamide

EXAMPLE 8A methyl 6-cyano-4-nitro-2-naphthoate

A solution of Example 1D (5.2 g, 0.025 mol) in concentrated sulfuric acid (75 mL) at 0° C. was treated with potassium nitrate (0.025 mol), stirred for 10 minutes, poured into ice (500 g), and extracted with ethyl acetate. The combined extracts were washed sequentially with water, 1M NaOH, and brine, dried (MgSO$_4$), treated with silica gel, filtered, and concentrated to a volume of 200 mL. The mixture was heated until the solids dissolved, treated with ethanol (20 mL) and ether (20 mL), and stirred for 16 hours. The resulting precipitate was collected by filtration and washed with ethanol to provide the desired product. The filtrate was concentrated, treated with dichloromethane (250 mL) and silica gel, filtered, and concentrated. Crystallization from ethyl acetate/ethanol provided additional desired product.

MS (DCI/NH$_3$) m/e 257 (M+H)$^+$.

EXAMPLE 8B methyl 4-amino-6-cyano-2-naphthoate

A solution of Example 8A (1.0 g, 3.90 mmol) and 10% Pd/C (112 mg) in ethyl acetate (80 mL) at room temperature was stirred under1 atm of hydrogen for 9 hours, purged with nitrogen for 1 hour, filtered, and concentrated to provide the desired product.

MS (DCI/NH$_3$) m/e 227 (M+NH$_4$)$^+$.

EXAMPLE 8C methyl 6-cyano-4-iodo-2-naphthoate

A solution of Example 8B (2.0 g, 7.60 mmol) in 3M HCl (150 ml) at 0° C. was treated dropwise with 40% sodium nitrite (13 mL), stirred for 10 minutes, treated with a solution of KI (1.9 g, 14.9 mmol) in water (2 mL), warmed to room temperature, and stirred for 16 hours. The mixture was treated with sodium thiosulfate (2 g) and extracted with ethyl acetate. The combined extracts were washed sequentially with 30% sodium thiosulfate, 10% sodium bicarbonate, and 10% NaCl, dried (Na$_2$SO$_4$), filtered, and concentrated. The concentrate was purified by flash column chromatography on silica gel with 25% ethyl acetate/hexanes to provide the desired product.

MS (DCI/NH$_3$) m/e 338 (M+H)$^+$.

EXAMPLE 8D diethyl (6-cyano-4-iodo-2-naphthyl)methylphosphonate

The desired product was prepared by substituting Example 8C for Example 1E in Examples 1F–1H.

MS (DCI/NH$_3$) m/e 446 (M+H)$^+$.

EXAMPLE 8E 8-iodo-6-(2-(1-isopropyl-3,4-dihydro-7-isoquinolinyl)ethenyl)-2-naphthonitrile The desired product was prepared by substituting Example 8D for Example 1H in Example 1K.

MS (APCI(+)) m/e 477 (M+H)$^+$.

EXAMPLE 8F 8-(1-hydroxy-3-methylbutyl)-6-(2-(1-isopropyl-3,4-dihydro-7-isoquinolinyl)ethenyl)-2-naphthonitrile A solution of Example 8E (250 mg, 0.52 mmol) in THF (5 mL) at −90° C. was treated with 2.5M n-butyllithium in hexanes (0.210 mL, 0.525 mmol), stirred for 2 minutes, treated with isovaleraldehyde (0.056 mL, 0.63 mmol), and stirred for 30 minutes. The reaction was warmed to room temperature, quenched with water, and extracted with ethyl acetate. The combined extracts were dried (Na$_2$SO$_4$), filtered, and concentrated. The concentrate was purified by flash column chromatography on silica gel with 25% ethyl acetate/hexanes to provide the desired product.

MS (APCI(+)) m/e 437 (M+H)$^+$.

EXAMPLE 8G 8-(1-hydroxy-3-methylbutyl)-6-(2-(1-isopropyl-3,4-dihydro-7-isoquinolinyl)cyclopropyl)-2-naphthonitrile The desired product was prepared by substituting Example 8F for Example 1L in Example 1M.

MS (APCI(+)) m/e 451 (M+H)$^+$.

EXAMPLE 8H 6-(2-(1-isopropyl-3,4-dihydro-7-isoquinolinyl)cyclopropyl)-8-((1E)-3-methyl-1-butenyl)-2-naphthonitrile A solution of Example 8G (120 mg, 0.27 mmol) in 1,2 diethoxyethane was treated with para-toluenesulfonic acid (253 mg, 1.3 mmol) and 3 Å molecular sieves (500 mg), heated to 185° C., and stirred for 3 hours. The mixture was cooled to room temperature, quenched with saturated NaHCO$_3$, and extracted with ethyl acetate. The combined extracts were washed with water, dried (Na$_2$SO$_4$), filtered, and concentrated. The concentrate was purified by flash column chromatography on silica gel with 25% ethyl acetate/hexanes to provide the desired product.

MS (APCI(+)) m/e 433 (M+H)$^+$.

EXAMPLE 8I 6-(2-(1-isopropyl-3,4-dihydro-7-isoquinolinyl)cyclopropyl)-8-((1E)-3-methyl-1-butenyl)-2-naphthalenecarboximidamide The desired product was prepared by substituting Example 8H for Example 1M in Example 1N.

MS (APCI(+)) m/e 450 (M+H)$^+$;

$^1$H NMR (300 MHz, DMSO-d$_6$) δ9.52 (s, 2H), 9.14 (s, 2H), 8.66 (s, 1H), 8.03 (d, 1H), 7.99(s, 1H), 7.82 (dd, 1H), 7.75 (s, 1H), 7.61(m, 2H), 7.47 (d, 1H), 7.28 (d, 1H), 6.47 (dd, 1H), 3.92 (m, 1H), 3.81 (m, 2H), 3.05 (m, 2H), 2.68–2.54 (m, 3H), 1.77 (m, 2H), 1.34 (t, 6H), 1.17 (d, 6H);

Anal. calcd. for C$_{31}$H$_{35}$N$_3$.1.7HCl: C, 63.70; H, 6.67; N, 7.19. Found; C, 63.74; H, 6.80; N, 7.13.

EXAMPLE 9

6-(2-(1-cyclohexyl-3,4-dihydro-7-isoquinolinyl)cyclopropyl)-2-naphthalenecarboximidamide

EXAMPLE 9A 6-(2-(1-cyclohexyl-3,4-dihydro-7-isoquinolinyl)cyclopropyl)-2-naphthonitrile The desired product was prepared by substituting cyclohexanecarbonyl chloride for butanoyl chloride in Examples 11A–11D.

EXAMPLE 9B 6-(2-(1-cyclohexyl-3,4-dihydro-7-isoquinolinyl)cyclopropyl)-2-naphthalenecarboximidamide The desired product was prepared by substituting Example 9A for Example 1M in Example 1N MS (DCI/NH$_3$) m/e 422 (M+H)$^+$;.

¹H NMR (300 MHz, DMSO-d$_6$) δ9.45 (br s, 1.5H), 9.10 (br s, 1.5H), 8.45 (s, 1H), 8.04 (d, 1H), 8.02 (d, 1H), 7.85 (s, 1H), 7.80 (d, 1H), 7.53 (d, 1H), 7.44 (s, 1H), 7.18 (s, 2H), 3.51 (m, 4H), 3.02 (m, 1H), 2.51 (m, 2H), 1.75 (m, 6H), 1.30 (m, 6H);

Anal. calcd. for C$_{29}$H$_{31}$N$_3$.HCl: C, 76.40; H, 7.04; N, 9.17. Found: C, 72.75; H, 7.06; N, 8.34.

EXAMPLE 10

6-(2-(1-phenyl-3,4-dihydro-7-isoquinolinyl) cyclopropyl)-2-naphthalenecarboximidamide

EXAMPLE 10A 6-(2-(1-phenyl-3,4-dihydro-7-isoquinolinyl) cyclopropyl)-2-naphthonitrile The desired product was prepared by substituting benzoyl chloride for butanoyl chloride in Examples 11A–11D.

EXAMPLE 10B 6-(2-(1-phenyl-3,4-dihydro-7-isoquinolinyl) cyclopropyl)-2-naphthalenecarboximidamide The desired product was prepared by substituting Example 10A for Example 1M in Example 1N.
MS (DCI/NH$_3$) m/e 416 (M+H)$^+$;
¹H NMR (300 MHz, DMSO-d$_6$) δ9.25 (br s, 3H), 8.42 (s, 1H), 8.01 (d, 1H), 7.97 (d, 1H), 7.82 (s, 1H), 7.78 (d, 1H), 7.53 (m, 2H), 7.44 (m, 4H), 7.33 (d, 1H), 7.29 (d, 1H), 7.05 (s, 1H), 3.73 (m, 2H), 2.73 (m, 2H), 2.39 (m, 2H), 1.63 (m, 1H), 1.51 (m, 1H);

Anal. calcd. for C$_{29}$H$_{25}$N$_3$.HCl: C, 77.06; H, 5.80; N, 9.30. Found: C, 72.78; H, 5.70; N, 8.33.

EXAMPLE 11

6-(2-(2-methyl-1-propyl-1,2,3,4-tetrahydro-7-isoquinolinyl)cyclopropyl)-2-naphthalenecarboximidamide

EXAMPLE 11A 7-bromo-1-propyl-3,4-dihydroisoquinoline

The desired product was prepared by substituting butanoyl chloride for 2-methylpropanoyl chloride in Example 1I.
MS (APCI(+)) m/e 252 (M+H)$^+$.

EXAMPLE 11B 1-propyl-3,4-dihydro-7-isoquinolinecarbaldehyde

The desired product was prepared by substituting Example 11A for Example 11 in Example 1J.
MS (ESI(+)) m/e 202 (M+H)$^+$.

EXAMPLE 11C 6-(2-(1-propyl-3,4-dihydro-7-isoquinolinyl)ethenyl)-2-naphthonitrile The desired product was prepared by substituting Example 11B and Example 42C for Example 1J and Example 1H, respectively, in Example 1K
MS (ESI(+)) m/e 351 (M+H)$^+$. .

EXAMPLE 11D 6-(2-(1-propyl-3,4-dihydro-7-isoquinolinyl) cyclopropyl)-2-naphthonitrile The desired product was prepared by substituting Example 11C for Example 1L in Example 1M.
MS (ESI(+)) m/e 365 (M+H)$^+$.

EXAMPLE 11E 6-(2-(2-methyl-1-propyl-1,2,3,4-tetrahydro-7-isoquinolinyl)cyclopropyl)-2-naphthonitrile The desired product was prepared by substituting Example 11D for Example 31F in Example 32A.
MS (APCI(+)) m/e 381 (M+H)$^+$.

EXAMPLE 11F 6-(2-(2-methyl-1propyl-1,2,3,4-tetrahydro-7-isoquinolinyl)cyclopropyl)-2-naphthalenecarboximidamide The desired product was prepared by substituting Example 11E for Example 1M in Example 1N.
MS (DCI/NH$_3$) m/e 398 (M+H)$^+$;
¹H NMR (300 MHz, DMSO-d$_6$) δ9.40 (br s, 2H), 9.11 (br s, 2H), 8.45 (s, 1H), 8.04 (m, 2H), 7.86 (s, 1H), 7.79 (dd, 1H), 7.51 (d, 1H), 7.18 (m, 2H), 7.06 (d, 1H), 4.37 (m, 1H), 3.52 (m, 1H), 3.36 (m, 1H), 3.06 (m, 2H), 2.85 (m, 3H), 2.44 (m, 2H), 1.96 (m, 1H) 1.80 (m, 1H), 1.68 (m, 1H), 1.58 (m, 1H), 1.44 (m, 2H), 0.94 (m, 3H);

Anal. calcd. for C$_{27}$H$_{31}$N$_3$.2.55CF$_3$CO$_2$H: C, 56.01; H, 4.91; N, 6.10. Found: C, 55.99; H, 5.10; N, 5.89.

EXAMPLE 12

6-(2-(1-cyclohexyl-2-methyl-1,2,3,4-tetrahydro-7-isoquinolinyl)cyclopropyl)-2-naphthalenecarboximidamide The desired product was prepared by substituting cyclohexanecarbonyl chloride for butanoyl chloride in Example 11.
MS (DCI/NH$_3$) m/e 438 (M+H)$^+$;
¹H NMR (300 MHz, DMSO-d$_6$) δ9.41 (br s, 2H), 9.14 (br s, 2H), 8.45 (s, 1H), 8.04 (m, 2H), 7.86 (s, 1H), 7.80 (dd, 1H), 7.51 (d, 1H), 7.24 (m, 1H), 7.16 (m, 1H), 7.02 (d, 1H), 4.17 (m, 1H), 3.66 (m, 1H), 3.25 (m, 1H), 3.00 (m, 2H), 2.80 (m, 3H), 2.45 (m, 2H), 2.35 (m, 1H), 1.94–1.36 (m, 7H), 1.35–0.80 (m, 5H);

Anal. calcd. for C$_{30}$H$_{35}$N$_3$.2CF$_3$CO$_2$H.0.95H$_2$O: C, 59.81; H, 5.74; N, 6.15. Found: C, 59.87; H, 5.90; N, 5.76.

EXAMPLE 13

6-(2-(1-isopropyl-1,2,3,4-tetrahydro-7-isoquinolinyl) ethenyl)-2-naphthalenecarboximidamide

EXAMPLE 13A 6-hydroxy-2-naphthonitrile

A solution of 6-bromo-2-naphthol (25.0 g, 112 mmol) and copper(I) cyanide (11 g, 123 mmol) in DMF (30 mL) was heated to 135° C., stirred for 18 hours, cooled to room temperature, diluted with ethyl acetate (50 mL), triturated with 10% sodium hydroxide, and filtered through diatomaceous earth (Celite®). The filtrate was adjusted to pH 2 and extracted with ethyl acetate. The combined extracts were concentrated, dissolved in ethanol (150 mL), triturated with water, and filtered to provide the desired product.

MS (DCI/NH$_3$) m/e 170 (M+H)$^+$.

EXAMPLE 13B 6-cyano-2-naphthyl trifluoromethanesulfonate

A solution of Example 13A (14.01 g, 82.8 mmol) and triethylamine (9.2 g, 91.1 mmol) in dichloromethane (40 mL) at 0° C. was treated dropwise with trifluoromethanesulfonic anhydride (28 g, 99.4 mmol), warmed to room temperature, stirred for 48 hours, concentrated, dissolved in ethanol, (50 mL) triturated with water, and filtered to provide the desired product.

MS (DCI/NH$_3$) m/e 319 (M+NH$_4$)$^+$.

EXAMPLE 13C 6-((trimethylsilyl)ethynyl)-2-naphthonitrile

A solution of Example 13B (350 mg, 1.16 mmol), trimethylsilylacetylene(148 mg, 1.51 mmol), Pd(OAc)$_2$ (26 mg, 0.12 mmol), triphenylphosphine (61 mg, 0.23 mmol), and triethylamine (2 mL) in acetonitrile (1 mL) in a sealed was heated to 100° C., stirred for 19 hours, diluted with ethyl acetate (20 mL), washed with water, dried (MgSO$_4$), filtered, treated with silica gel (4 g), and concentrated. The concentrated was purified by flash column chromatography on silica gel with 10% ethyl acetate/hexanes to provide the desired product.

MS (DCI/NH$_3$) m/e 267 (M+NH$_4$)$^+$.

EXAMPLE 13D 6-ethynyl-2-naphthonitrile

A mixture of Example 13C (0.4 g, 1.6 mmol) and K$_2$CO$_3$ (0.4 g, 3.2 mmol) in methanol (16 mL) was stirred at room temperature for 18 hours, concentrated, treated with water, and extracted with dichloromethane. The combined extracts were washed with 0.5M HCl and brine, dried (MgSO$_4$), filtered, and concentrated to provide the desired product.

MS (DCI/NH$_3$) m/e 195 (M+NH$_4$)$^+$.

EXAMPLE 13E 6-(2-(tributylstannyl)ethenyl)-2-naphthonitrile

A suspension of Example 13D (130 mg, 0.73 mmol), 2,2'-azobisisobutyronitrile (3.3 mg, 0.02 mmol) in toluene (3.5 mL) was treated with tributyltin hydride (0.32 g, 1.1 mmol), heated to 85° C., stirred for 1 hour, cooled to room temperature, and concentrated. The concentrate was purified by flash column chromatography on silica gel with 98:2:1/ hexanes:ethyl acetate:triethylamine to provide the desired product.

MS (APCI(+)) m/e 468 (M+H)$^+$.

EXAMPLE 13F 1-isopropyl-3,4-dihydroisoquinoline

The desired product was prepared by substituting 2-phenylethylamine for 2-(4-bromophenyl)ethylamine in Example 11.

MS (ESI(+)) m/e 174 (M+H)$^+$.

EXAMPLE 13G 1-isopropyl-7-nitro-3,4-dihydroisoquinoline

A solution of Example 13F (0.73 g, 4.2 mmol) in concentrated H$_2$SO$_4$ (7.5 mL) at 0° C. was treated with KNO$_3$ (0.47 g, 4.6 mmol), stirred for 30 minutes, treated with ice water, adjusted to pH>7 with 25% NaOH, and extracted with dichloromethane. The combined extracts were washed with H$_2$O and brine, dried (MgSO$_4$), filtered, and concentrated. The concentrate was purified by flash column chromatography on silica gel with 30% ethyl acetate/hexanes to provide the desired product.

MS (DCI/NH$_3$) m/e 219 (M+H)$^+$.

EXAMPLE 13H 1-isopropyl-3,4-dihydro-7-isoquinolinamine

A solution of Example 13G (180 mg, 0.82 mmol) and Raney nickel (0.12 g) in ethyl acetate (30 mL) at room temperature was hydrogenated in a Parr shaker at 4 atmospheres for 48 hours, filtered through diatomaceous earth (Celite®), and concentrated to provide the desired product.

MS (DCI/NH$_3$) m/e 189 (M+H)$^+$.

EXAMPLE 13I 7-iodo-1-isopropyl-3,4-dihydroisoquinoline

A solution of Example 13H in 2M HCl (5 mL) at 0° C. was treated dropwise with a solution of sodium nitrite (200 mg, 2.9 mmol) in H$_2$O (4.9 mL), stirred for 10 minutes, treated dropwise with a solution of KI (13.5 g, 81.3 mmol) in H$_2$O (9.8 mL), warmed to room temperature, stirred for 1.5 hours, warmed to 80° C., and stirred for 10 minutes. The mixture was cooled to 0° C., adjusted to pH>7 with 28% NH$_4$OH, and extracted with dichloromethane. The combined extracts were washed sequentially with 10% aqueous Na$_2$S$_2$O$_3$, H$_2$O, and brine, dried (MgSO$_4$), filtered, and concentrated to provide the desired product.

MS (DCI/NH$_3$) m/e 300 (M+H)$^+$.

EXAMPLE 13J 6-(2-(1-isopropyl-3,4-dihydro-7-isoquinolinyl) ethenyl)-2-naphthonitrile A solution of Example 13I (70 mg, 0.23 mmol), dichlorobis(triphenylphosphine)palladium (II) (7.0 mg, 0.01 mmol), and LiCl (31 mg, 0.73 mmol) in DMF (1.7 mL) was treated dropwise with a solution of Example 13E (120 mg, 0.26 mmol) in DMF (0.2 mL). The mixture was heated to 80° C., stirred for 1.75 hours, cooled to room temperature, diluted with ethyl acetate, washed with H$_2$O and brine, dried (MgSO$_4$), filtered, and concentrated. The concentrate was purified by flash column chromatography on silica gel with 30% ethyl acetate/hexanes to provide the desired product.

MS (DCI/NH$_3$) m/e 351 (M+H)$^+$.

EXAMPLE 13K 6-(2-(1-isopropyl-1,2,3,4-tetrahydro-7-isoquinolinyl) ethenyl)-2-naphthonitrile A solution of Example 13J (200 mg, 0.5 mmol) in methanol (5 ml) at room temperature was treated with sodium borohydride (80 mg, 2 mmol), stirred for 30 minutes, quenched with water (5 mL), and extracted with dichloromethane. The combined extracts were washed with 10% NaCl, dried (Na$_2$SO$_4$), filtered, and concentrated to provide the desired product.

MS (DCI/NH$_3$) m/e 353 (M+H)$^+$.

EXAMPLE 13L 6-(2-(1-isopropyl-1,2,3,4-tetrahydro-7-isoquinolinyl) ethenyl)-2-naphthalenecarboximidamide The desired product was prepared by substituting Example 13K for Example 1M in Example 1N.

MS (ESI(+)) m/e 370 (M+H)$^+$;

$^1$H NMR (300 MHz, DMSO-d$_6$) δ9.80 (br s, 1H), 9.60 (s, 2H), 9.20 (s, 2H), 8.70 (br s, 1H), 8.50 (s, 1H), 8.15, (d, 2H), 8.05 (d, 2H), 7.85 (d, 1H), 7.65 (d, 2H), 7.50 (s, 2H), 7.35 (d, 1H), 4.45 (m, 1H), 3.85 (t, 2H), 3.05 (t, 2H), 2.50 (m, 2H), 1.25 (d, 3H), 0.95 (m, 3H);

Anal. calcd. for C$_{25}$H$_{27}$N$_3$.2HCl.H$_2$O: C, 65.21; H, 6.79; N, 9.13. Found: C, 65.60; H, 6.62; N, 9.06.

EXAMPLE 14

6-(2-(1-isopropyl-3,4-dihydro-7-isoquinolinyl) cyclopropyl)-2-naphthalenecarboximidamide

EXAMPLE 14A 6-(2-(1-isopropyl-3,4-dihydro-7-isoquinolinyl) cyclopropyl)-2-naphthonitrile The desired product was prepared by substituting Example 13J for Example 1L in Example 1M.

EXAMPLE 14B 6-(2-(1-isopropyl-3,4-dihydro-7-isoquinolinyl) cyclopropyl)-2-naphthalenecarboximidamide The desired product was prepared by substituting Example 14A for Example 1M in Example 1N.

MS (ESI(+)) m/e 382 (M+H)$^+$;

1H NMR (300 MHz, DMSO-d$_6$) δ9.40 (s, 2H), 9.10 (s, 2H), 8.47 (s, 1H), 8.05, (d, 2H), 7.95 (br s, 1H), 7.85 (d, 1H), 7.65 (d, 2H), 7.50 (d, 2H), 7.45 (d, 1H), 3.85–3.65 (m, 3H), 3.05 (t, 2H), 2.50 (m, 2H), 1.84 (m, 2H), 1.35 (m, 6H);

Anal. calcd. for C$_{26}$H$_{27}$N$_3$.2CF$_3$CO$_2$H.H$_2$O: C, 57.42; H, 4.98; N, 6.70. Found: C, 57.62; H, 4.81; N, 6.50.

EXAMPLE 15

6-(2-(2-acetyl-1-isopropyl-1,2,3,4-tetrahydro-7-isoquinolinyl)cyclopropyl)-2-naphthalenecarboximidamide

EXAMPLE 15A 6-(2-(2-acetyl-1-isopropyl-1,2,3,4-tetrahydro-7-isoquinolinyl)ethenyl)-2-naphthonitrile The desired product was prepared by substituting Example 13K and acetyl chloride for Example 42J and methyl chloroformate, respectively, in Example 42K.

EXAMPLE 15B 6-(2-(2-acetyl-1-isopropyl-1,2,3,4-tetrahydro-7-isoquinolinyl)cyclopropyl)-2-naphthonitrile The desired product was prepared by substituting Example 15A for Example 1L in Example 1M.

EXAMPLE 15C 6-(2-(2-acetyl-1-isopropyl-1,2,3,4-tetrahydro-7-isoquinolinyl)cyclopropyl)-2-naphthalenecarboximidamide The desired product was prepared by substituting Example 15B for Example 1M in Example 1N.

MS (ESI(+)) m/e 426 (M+H)$^+$;

$^1$H NMR (300 MHz, DMSO-d$_6$) δ9.40 (s, 2H), 9.10 (s, 2H), 8.47 (s, 1H), 8.05, (d, 2H), 7.95 (br s, 1H), 7.85 (d, 1H), 7.65 (d, 2H), 7.5 (d, 2H), 7.45 (d, 1H), 3.85–3.65 (m, 3H), 3.05 (t, 2H), 2.5 (m, 2H), 2.1 (s, 3H), 1.84 (m, 2H), 1.35 (m, 6H);

Anal. calcd. for C$_{28}$H$_{31}$N$_3$O.CF$_3$CO$_2$H.H$_2$O: C, 64.62; H, 6.15; N, 7.54. Found: C, 64.39; H, 5.99; N, 7.29.

EXAMPLE 16

6-(2-(1-isopropyl-2-methyl-1,2,3,4-tetrahydro-7-isoquinolinyl)ethenyl)-2-naphthalenecarboximidamide

EXAMPLE 16A 6-(2-(1-isopropyl-2-methyl-1,2,3,4-tetrahydro-7-isoquinolinyl)ethenyl)-2-naphthonitrile The desired product was prepared by substituting Example 13J for Example 31F in Example 32A.

MS (ESI(+)) m/e 367 (M+H)$^+$.

EXAMPLE 16B 6-(2-(1-isopropyl-2-methyl-1,2,3,4-tetrahydro-7-isoquinolinyl)ethenyl)-2-naphthalenecarboximidamide The desired product was prepared by substituting Example 16A for Example 1M in Example 1N.

MS (ESI(+)) m/e 384 (M+H)$^+$;

$^1$H NMR (300 MHz, DMSO-d$_6$) δ9.80 (br s, 1H), 9.60 (s, 2H), 9.20 (s, 2H), 8.70 (br s, 1H), 8.50 (s, 1H), 8.15, (d, 2H), 8.05 (d, 2H), 7.85 (d, 1H), 7.65 (d, 2H), 7.50 (s, 2H), 7.35 (d, 1H), 4.45 (m, 1H), 3.85 (t, 2H), 3.05 (t, 2H), 2.85 (s, 3H), 2.50 (m, 2H), 1.25 (d, 3H), 0.95 (m, 3H);

Anal. calcd. for C$_{26}$H$_{29}$N$_3$.2.25CF$_3$CO$_2$H: C, 57.23; H, 4.92; N 6.56. Found: C, 57.55; H, 5.01; N, 6.60.

EXAMPLE 17 methyl 7-(2-(6-(amino(imino)methyl)-2-naphthyl) ethenyl)-1-isopropyl-3,4-dihydro-2(1H)-isoquinolinecarboxylate

EXAMPLE 17A methyl 7-(2-(6-cyano-2-naphthyl)ethenyl)-1-isopropyl-3,4-dihydro-2(1H)-isoquinolinecarboxylate The desired product was prepared by substituting methyl chloroformate for acetyl chloride in Example 15A.

EXAMPLE 17B methyl 7-(2-(6-(amino(imino)methyl)-2-naphthyl) ethenyl)-1-isopropyl-3,4-dihydro-2(1H)-isoquinolinecarboxylate The desired product was prepared by substituting Example 17A for Example 1M in Example 1N.

MS (ESI(+)) m/e 428 (M+H)$^+$;

¹H NMR (300 MHz, DMSO-d₆) δ9.60 (s, 2H), 9.20 (s, 2H), 8.70 (br s, 1H), 8.50 (s, 1H), 8.15, (d, 2H), 8.05 (d, 2H), 7.85 (d, 1H), 7.65 (d, 2H), 7.50 (s, 2H), 7.35 (d, 1H), 4.45 (m, 1H), 3.85 (t, 2H), 3.61 (s, 3H), 3.05 (t, 2H), 2.50 (m, 2H), 1.25 (d, 3H), 0.95 (m, 3H);

Anal. calcd. for $C_{27}H_{29}N_3O_2 \cdot CF_3CO_2H$: C, 64.32; H, 5.58; N, 7.76. Found: C, 64.01; H, 5.61; N, 7.31.

EXAMPLE 18

6-(2-(1-isopropyl-2-methyl-1,2,3,4-tetrahydro-7-isoquinolinyl)cyclopropyl)-2-naphthalenecarboximidamide

EXAMPLE 18A 6-(2-(1-isopropyl-2-methyl-1,2,3,4-tetrahydro-7-isoquinolinyl)cyclopropyl)-2-naphthonitrile The desired product was prepared by substituting Example 16A for Example 1L in Example 1M.

EXAMPLE 18B 6-(2-(1-isopropyl-2-methyl-1,2,3,4-tetrahydro-7-isoquinolinyl)cyclopropyl)-2-naphthalenecarboximidamide The desired product was prepared by substituting Example 18A for Example 1M in Example 1N.

MS (ESI(+)) m/e 398 (M+H)⁺;

¹H NMR (300 MHz, DMSO-d₆) δ9.40 (s, 2H), 9.10 (s, 2H), 8.47 (s, 1H), 8.05, (d, 2H), 7.95 (br s, 1H), 7.85 (d, 1H), 7.65 (d, 2H), 7.50 (d, 2H), 7.45 (d, 1H), 3.85–3.65 (m, 3H), 3.05 (t, 2H), 2.85 (s, 3H), 2.50 (m, 2H), 1.84 (m, 2H), 1.35 (m, 6H);

Anal. calcd. for $C_{27}H_{31}N_3 \cdot 2CF_3CO_2H \cdot H_2O$: C, 57.85; H, 5.48; N, 6.53. Found: C, 57.86; H, 5.38; N, 6.32.

EXAMPLE 19

6-(2-(2-benzyl-1-isopropyl-1,2,3,4-tetrahydro-7-isoquinolinyl)cyclopropyl)-2-naphthalenecarboximidamide The desired product was prepared by substituting Example 13K for Example 49A in Examples 49B–49D.

MS (ESI(+)) m/e 474 (M+H)⁺;

¹H NMR (300 MHz, DMSO-d₆) δ9.40 (s, 2H), 9.10 (s, 2H), 8.47 (s, 1H), 8.05, (d, 2H), 7.95 (br s, 1H), 7.85 (d, 1H), 7.65 (d, 2H), 7.50 (d, 2H), 7.45 (d, 1H), 7.30–7.08 (m, 5H), 3.85–3.65 (m, 3H), 3.05 (t, 2H), 2.50 (m, 2H), 2.20 (s, 2H), 1.84 (m, 2H), 1.35 (m, 6H);

Anal. calcd. for $C_{33}H_{35}N_3 \cdot 2CF_3CO_2H \cdot 0.5H_2O$: C, 62.53; H, 5.39; N, 5.91. Found: C, 62.30; H, 5.33; N, 5.49.

EXAMPLE 20

6-(2-(1-isopropyl-1,2,3,4-tetrahydro-7-isoquinolinyl)cyclopropyl)-2-naphthalenecarboximidamide

EXAMPLE 20A 6-(2-(1-isopropyl-1,2,3,4-tetrahydro-7-isoquinolinyl)cyclopropyl)-2-naphthonitrile The desired product was prepared by substituting Example 13K for Example 1L in Example 1M.

EXAMPLE 20B 6-(2-(1-isopropyl-1,2,3,4-tetrahydro-7-isoquinolinyl)cyclopropyl)-2-naphthalenecarboximidamide The desired product was prepared by substituting Example 20A for Example 1M in Example 1N.

MS (ESI(+)) m/e 384 (M+H)⁺;

¹H NMR (300 MHz, DMSO-d₆) δ9.80 (br s, 1H), 9.40 (s, 2H), 9.10 (s, 2H), 8.47 (s, 1H), 8.05, (d, 2H), 7.95 (br s, 1H), 7.85 (d, 1H), 7.65 (d, 2H), 7.50 (d, 2H), 7.45 (d, 1H), 3.85–3.65 (m, 3H), 3.05 (t, 2H), 2.50 (m, 2H), 1.84 (m, 2H), 1.35 (m, 6H);

Anal. calcd. for $C_{26}H_{29}N_3 \cdot 2CF_3CO_2H \cdot 0.5H_2O$: C, 58.06; H, 5.20; N, 6.77. Found: C, 58.08; H, 4.96; N, 6.42.

EXAMPLE 21

6-(2-(1-isopropyl-2-(3-pyridinylmethyl)-1,2,3,4-tetrahydro-7-isoquinolinyl)cyclopropyl)-2-naphthalenecarboximidamide The desired product was prepared by substituting nicotinaldehyde for benzaldehyde in Example 19.

MS (ESI(+)) m/e 475 (M+H)⁺;

1H NMR (300 MHz, DMSO-d₆) δ9.40 (s, 2H), 9.10 (s, 2H), 8.47 (s, 1H), 8.24 (m, 1H), 8.12 (d, 1H), 8.05, (d, 2H), 7.95 (br s, 1H), 7.89 (s, 1H), 7.85 (d, 1H), 7.75 (d, 1H), 7.65 (d, 2H), 7.50 (d, 2H), 7.45 (d, 1H), 3.85–3.65 (m, 3H), 3.05 (t, 2H), 2.50 (m, 2H), 2.31 (s, 2H), 1.84 (m, 2H), 1.35 (m, 6H);

Anal. calcd. for $C_{32}H_{34}N_3 \cdot 2.6CF_3CO_2H$: C, 57.94; H, 4.78; N, 7.27. Found: C, 58.11; H, 4.84; N, 6.81.

EXAMPLE 22

8-bromo-6-(2-(1-isopropyl-3,4-dihydro-7-isoquinolinyl)ethenyl)-2-naphthalenecarboximidamide The desired product was prepared by substituting Example 1K for Example 1M in Example 1N.

MS (ESI(+)) m/e 446 (M+H)⁺;

¹H NMR (300 MHz, DMSO-d₆) δ9.58 (s, 2H), 9.27 (s, 2H), 8.55 (s, 1H), 8.44 (s, 1H), 8.36 (s, 1H), 8.23 (d, 1H), 8.21 (s, 1H), 8.08 (d, 1H), 7.91 (dd, 1H), 7.69 (d, 2H), 7.60 (d, 1H), 3.85 (m, 3H), 3.09 (t, 2H), 1.38 (d, 6H);

Anal. calcd. for $C_{25}H_{24}BrN_3 \cdot 2CF_3CO_2H$: C, 51.65; H, 3.89; N, 6.23. Found: C, 51.66; H, 4.11; N, 5.99.

EXAMPLE 23

6-(2-(2-(cyclopropylmethyl)-1-isopropyl-1,2,3,4-tetrahydro-7-isoquinolinyl)cyclopropyl)-2-naphthalenecarboximidamide

EXAMPLE 23A 6-(2-(2-(cyclopropylmethyl)-1-isopropyl-1,2,3,4-tetrahydro-7-isoquinolinyl)cyclopropyl)-2-naphthonitrile A solution of Example 20A (0.25 g, 0.95 mmol), cyclopropanecarboxaldehyde (71 mL, 0.95 mmol), and sodium cyanoborohydride (119 mg, 1.86 mmol), in methanol (3.5 mL) was heated to 50° C., stirred for 2 hours, cooled to room temperature, and treated with water. The resulting precipitate was collected by filtration, dried, and purified by flash column chromatography with 30% ethyl acetate/hexanes to provide the desired product.

MS (DCI/NH$_3$) m/e 421 (M+H)$^+$.

EXAMPLE 23B 6-(2-(2-(cyclopropylmethyl)-1-isopropyl-1,2,3,4-tetrahydro-7-isoquinolinyl)cyclopropyl)-2-naphthalenecarboximidamide The desired product was prepared by substituting Example 23A for Example 1M in Example 1N.

MS (ESI(+)) 438 (M+H)$^+$;

hu 1H NMR (300 MHz, DMSO-d$_6$) δ9.41 (s, 2H), 9.30 (s, 2H), 8.46 (s, 1H), 8.03 (m, 2H), 7.80 (m, 1H), 7.50 (m, 1H), 7.46 (s, 1H), 7.26–7.16 (m, 2H), 7.09 (d, 1H), 4.40 (m, 1H), 3.46 (m, 1H), 3.35 (m, 1H), 2.43 (m, 1H), 2.25 (m, 1H), 1.67 (m, 2H), 1.15 (dd, 3H), 0.80 (dd, 3H), 0.65 (m, 2H), 0.43 (m, 1H), 0.30 (m, 1H);

Anal. calcd. for C$_{30}$H$_{35}$N$_3$.2CF$_3$CO$_2$H.1.5H$_2$O: C, 58.95; H, 5.82; N, 6.07. Found: C, 58.95; H, 5.30; N, 6.16.

EXAMPLE 24

6-(2-(2-ethyl-1-isopropyl-1,2,3,4-tetrahydro-7-isoquinolinyl)cyclopropyl)-2-naphthalenecarboximidamide

EXAMPLE 24A 6-(2-(2-ethyl-1-isopropyl-1,2,3,4-tetrahydro-7-isoquinolinyl)cyclopropyl)-2-naphthonitrile A solution of Example 20A (240 mg, 0.66 mmol), ethyl iodide (0.11 mL, 1.32 mmol), and triethylamine (0.18 mL, 1.32 mmol) in THF at 45° C. was stirred for 4 hours and concentrated. The concentrate was purified by flash column chromatography with 30% ethyl acetate/hexanes to provide the desired product.

MS (DCI/NH$_3$) m/e 395 (M+H)$^+$.

EXAMPLE 24B 6-(2-(2-ethyl-1-isopropyl-1,2,3,4-tetrahydro-7-isoquinolinyl)cyclopropyl)-2-naphthalenecarboximidamide The desired product was prepared by substituting Example 24A for Example 1M in Example 1N.

MS (ESI(+)) m/e 412 (M+H)$^+$;

$^1$H NMR (300 MHz, DMSO-d$_6$) δ9.53 (s, 2H), 9.45 (s, 2H), 8.48 (s, 1H), 8.03 (m, 2H) 7.86 (s, 1H), 7.83(d, 1H), 7.52 (d, 1H), 7.25–7.15 (m, 2H), 7.10 (d, 1H), 4.27 (s, 1H), 3.65(m, 1H), 3.34 (m, 1H), 3.12 (m, 2H), 3.01 (t, 2H), 2.45 (m, 2H), 2.21 (m, 1H), 1.67 (t, 2H), 1.29 (dd, 3H), 1.14 (t, 3H), 0.81 (t, 3H);

Anal. calcd. for C$_{28}$H$_{33}$N$_3$.2CF$_3$CO$_2$H.H$_2$O: C, 58.44; H, 5.67; N, 6.39. Found: C, 58.34; H, 5.43; N, 6.38.

EXAMPLE 25

6-(2-(2-allyl-1-isopropyl-1,2,3,4-tetrahydro-7-isoquinolinyl)cyclopropyl)-2-naphthalenecarboximidamide

EXAMPLE 25A 6-(2-(2-allyl-1-isopropyl-1,2,3,4-tetrahydro-7-isoquinolinyl)cyclopropyl)-2-naphthonitrile The desired product was prepared by substituting allyl bromide for ethyl iodide in Example 24A MS (DCI/NH$_3$) m/e 407 (M+H)$^+$. .

EXAMPLE 25B 6-(2-(2-allyl-1-isopropyl-1,2,3,4-tetrahydro-7-isoquinolinyl)cyclopropyl)-2-naphthalenecarboximidamide The desired product was prepared by substituting Example 25A for Example 1M in Example 1N.

MS (ESI(+)) m/e 424 (M+H)$^+$;

$^1$H NMR (300 MHz, DMSO-d$_6$) δ9.48 (s, 1H), 9.41 (s, 2H), 9.20 (s, 2H), 8.45 (s, 1H), 8.03 (m, 2H), 7.86 (s, 1H), 7.80 (m, 1H), 7.60 (d, 1H), 7.50 (m, 1H), 7.26–7.16 (m, 2H), 6.06–6.01 (m, 1H), 5.55–5.49 (m, 2H), 4.21 (s, 1H), 3.75 (s, 2H), 3.63 (s, 2H), 3.00 (m, 2H), 2.49–2.34 (m, 2H), 2.20 (s, 1H), 1.67 (m, 1H), 1.10 (t, 3H), 0.79 (t, 3H);

Anal. calcd. for C$_{29}$H$_{33}$N$_3$.2CF$_3$CO$_2$H.H$_2$O: C, 59.19; H, 5.57; N, 6.27. Found: C, 59.51; H, 5.39; N, 5.88.

EXAMPLE 26

6-(2-(2-(2-hydroxyethyl)-1-isopropyl-1,2,3,4-tetrahydro-7-isoquinolinyl)cyclopropyl)-2-naphthalenecarboximidamide

EXAMPLE 26A 6-(2-(2-(2-hydroxyethyl)-1-isopropyl-1,2,3,4-tetrahydro-7-isoquinolinyl)cyclopropyl)-2-naphthonitrile The desired product was prepared by substituting 2-bromoethanol for ethyl iodide in Example 24A.

MS (DCI/NH$_3$) m/e 411 (M+H)$^+$.

EXAMPLE 26B 6-(2-(2-(2-hydroxyethyl)-1-isopropyl-1,2,3,4-tetrahydro-7-isoquinolinyl)cyclopropyl)-2-naphthalenecarboximidamide The desired product was prepared by substituting Example 26A for Example 1M in Example 1N.

MS (ESI(+)) m/e 428 (M+H)$^+$;

$^1$H NMR (300 MHz, DMSO-d$_6$) δ9.41 (s, 2H), 9.18 (s, 2H), 9.04 (s, 1H), 8.45 (s, 1H), 8.04 (m, 2H), 7.86 (s, 1H), 7.80 (m, 1H), 7.50 (d, 1H), 7.25–7.15 (m, 2H), 7.07 (d, 1H), 5.45 (s, 1H), 4.35 (s, 2H), 3.78–3.67 (m, 4H), 3.18–3.04 (m, 4H), 2.45–2.35 (m, 2H), 2.20 (m, 1H), 1.67 (t, 2H), 1.15 (t, 3H), 0.80 (t, 3H);

Anal. calcd. for C$_{28}$H$_{33}$N$_3$O.2CF$_3$CO$_2$H.H$_2$O: C, 57.05; H, 5.54; N, 6.24. Found: C, 57.29; H, 5.31; N, 6.14.

EXAMPLE 27

6-(2-(1,2-diisopropyl-1,2,3,4-tetrahydro-7-isoquinolinyl)cyclopropyl)-2-naphthalenecarboximidamide

EXAMPLE 27A 6-(2-(1,2-diisopropyl-1,2,3,4-tetrahydro-7-isoquinolinyl)cyclopropyl)-2-naphthonitrile The desired product was prepared by substituting 2-iodopropane for ethyl iodide in Example 24A.

MS (DCI/NH$_3$) m/e 409 (M+H)$^+$.

EXAMPLE 27B 6-(2-(1,2-diisopropyl-1,2,3,4-tetrahydro-7-isoquinolinyl)cyclopropyl)-2-naphthalenecarboximidamide The desired product was prepared by substituting Example 27A for Example 1M in Example 1N.

MS (ESI(+)) m/e 426 (M+H)$^+$;

$^1$H NMR (300 MHz, DMSO-d$_6$) δ9.38 (s, 2H), 9.00 (s, 2H), 8.67 (s, 1H), 8.44 (s, 1H), 8.06–8.00 (m, 2H), 7.86 (s, 1H), 7.80–7.76 (m, 1H), 7.52–7.49 (m, 1H), 7.25–7.21 (m, 2H), 7.18–7.12 (m, 1H), 4.39 (s, 1H), 3.62 (s, 1H), 3.18 (s, 1H), 2.95 (m, 2H), 2.45–2.32 (m, 2H), 2.15 (m, 1H), 1.69 (m, 2H), 1.34–1.27 (m, 6H), 1.13 (m, 3H), 0.72 (dd, 2H);

Anal. calcd. for $C_{29}H_{35}N_3 \cdot 2CF_3CO_2H \cdot H_2O$: C, 58.44; H, 5.67; N, 6.39. Found: 58.34; H, 5.43; N, 6.38.

EXAMPLE 28

6-((1S,2S)-2-(1-isopropyl-3,4-dihydro-7-isoquinolinyl)cyclopropyl)-2-naphthalenecarboximidamide

EXAMPLES 28A AND 28B 6-((1S,2S)-2-(1-isopropyl-3,4-dihydro-7-isoquinolinyl)cyclopropyl)-2-naphthonitrile and 6-((1R,2R)-2-(1-isopropyl-3,4-dihydro-7-isoquinolinyl)cyclopropyl)-2-naphthonitrile Example 14B was separated into individual enantiomers by preparative chiral HPLC using 10% ethanol/hexanes to provide the desired products.

EXAMPLE 28C 6-((1S,2S)-2-(1-isopropyl-3,4-dihydro-7-isoquinolinyl)cyclopropyl)-2-naphthalenecarboximidamide The desired product was prepared by substituting Example 28A for Example 1M in Example 1N.

(α)$_D$ –268° (c 0.56, CH$_3$OH);

MS (ESI(+)) m/e 382 (M+H)$^+$;

$^1$H NMR (300 MHz, DMSO-d$_6$) δ9.41 (s, 2H), 9.11 (s, 2H), 8.45 (d, 1H), 8.04 (dd, 2H), 7.96 (s, 1H), 7.87 (s, 1H), 7.80 (dd, 1H), 7.62 (d, 1H), 7.53 (dd, 1H), 7.47 (d, 1H), 3.86 (m, 1H), 3.80 (t, 2H), 3.04 (t, 2H), 2.56 (m, 1H), 1.76 (t, 2H), 1.31 (t, 6H);

Anal. calcd. for $C_{26}H_{27}N_3 \cdot 2CF_3CO_2H$ 1.25H$_2$O: C, 57.01; H, 5.02; N, 6.65. Found: C, 56.91; H, 4.61; N, 6.40.

EXAMPLE 29

6-((1R,2R)-2-(1-isopropyl-3,4-dihydro-7-isoquinolinyl)cyclopropyl)-2-naphthalenecarboximidamide The desired product was prepared by substituting Example 28B for Example 1M in Example 1N.

(α)$_D$ +211° (c 0.56, CH$_3$OH);

MS (ESI(+)) m/e 382 (M+H)$^+$;

$^1$H NMR (300 MHz, DMSO-d$_6$) δ9.41 (s, 2H), 9.14 (s, 2H), 8.45 (s, 1H), 8.03 (d, 2H), 7.94 (s, 1H), 7.87 (s, 1H), 7.80 (d, 1H), 7.61 (d, 1H), 7.53 (d, 1H), 7.46 (d, 1H), 3.88 (m, 1H), 3.80 (t, 2H), 3.02 (m, 2H), 2.55 (m, 1H), 1.75 (t, 2H), 1.30 (t, 6H);

Anal. calcd. for $C_{26}H_{27}N_3 \cdot 2.1CF_3CO_2H \cdot H_2O$: C, 57.01; H, 5.02; N, 6.65. Found: C, 57.18; H, 4.85; N, 6.09.

EXAMPLE 30

6-(2-(1,2-dimethyl-1,2,3,4-tetrahydro-7-isoquinolinyl)cyclopropyl)-2-naphthalenecarboximidamide

EXAMPLE 30A 7-bromo-1-methyl-3,4-dihydroisoquinoline

The desired product was prepared by substituting acetic anhydride for 2-methylpropanoyl chloride in Example 1I MS (DCI/NH$_3$) m/e 224 (M+H)$^+$. .

EXAMPLE 30B methyl 1-methyl-3,4-dihydro-7-isoquinolinecarboxylate

A mixture of Example 30A (1.25 g, 5.6 mmol), bis (diphenylphosphino)ferrocenedichloropalladium (II) (457 mg, 0.56 mmol), and triethylamine (2 mL) in methanol (40 mL) was heated to 115° C. in a Parr shaker under 500 psi of carbon monoxide for 18 hours. The mixture was cooled to room temperature, filtered, and concentrated. The concentrate was purified by flash column chromatography on silica gel with 1% ethanol/dichloromethane to provide the desired product.

MS (DCI/NH$_3$) m/e 204 (M+H)$^+$.

EXAMPLE 30C methyl 1-methyl-1,2,3,4-tetrahydro-7-isoquinolinecarboxylate

A suspension of Example 30B (0.59 g, 2.9 mmol) in ethanol (6 mL) at 50° C. was treated with 10% Pd/C (300 mg) and stirred under 60 psi of hydrogen for 15 hours. The mixture was cooled to room temperature, filtered, and concentrated to provide the desired product.

MS (DCI/NH$_3$) m/e 206 (M+H)$^+$.

EXAMPLE 30D (1-methyl-1,2,3,4-tetrahydro-7-isoquinolinyl) methanol

A solution of Example 30C (0.51 g, 2.5 mmol) in THF (5 mL) at 0° C. was treated with LAH (190 mg, 5.0 mmol), heated to reflux, stirred for 1.5 hours, cooled to 0° C., treated with 20% NH$_4$Cl, and extracted with ethyl acetate. The combined extracts were washed with 10% NaCl, dried (Na$_2$SO$_4$), filtered, and concentrated to provide the desired product.

MS (DCI/NH$_3$) m/e 178 (M+H)$^+$.

EXAMPLE 30E tert-butyl 7-(hydroxymethyl)-1-methyl-3,4-dihydro-2(1H)-isoquinolinecarboxylate The desired product was prepared from Example 30D according to the procedure described in *Synthesis* 1986, 48.

MS (DCI/NH$_3$) m/e 278 (M+H)$^+$.

EXAMPLE 30F tert-butyl 7-formyl-1-methyl-3,4-dihydro-2(1H)-isoquinolinecarboxylate The desired product was prepared from Example 30E according to the procedure described in *J. Org. Chem.* 1974, 39, 3365.

MS (DCI/NH$_3$) m/e 276 (M+H)$^+$.

EXAMPLE 30G tert-butyl 7-(2-(6-cyano-2-naphthyl)ethenyl)-1-methyl-3,4-dihydro-2(1H)-isoquinolinecarboxylate The desired product was prepared by substituting Example 30F and Example 42C for Example 1J and Example 1H, respectively, in Example 1K.

MS (DCI/NH$_3$) m/e 425 (M+H)$^+$.

EXAMPLE 30H tert-butyl 7-(2-(6-cyano-2-naphthyl)cyclopropyl)-1-methyl-3,4-dihydro-2(1H)-isoquinolinecarboxylate The desired product was prepared by substituting Example 30G for Example 1L in Example 1M.

MS (DCI/NH$_3$) m/e 439 (M+H)$^+$.

EXAMPLE 30I 6-(2-(1-methyl-1,2,3,4-tetrahydro-7-isoquinolinyl)cyclopropyl)-2-naphthonitrile A solution of Example 30H (170 mg, 0.39 mmol) in 4M HCl in dioxane (2.5 mL) at 0° C. was stirred for 1.5 hours, then concentrated to provide the desired product.

MS (DCI/NH$_3$) m/e 339 (M+H)$^+$.

EXAMPLE 30J 6-(2-(1,2-dimethyl-1,2,3,4-tetrahydro-7-isoquinolinyl)cyclopropyl)-2-naphthonitrile A solution of Example 30I (130 mg, 0.38 mmol) in methanol (3.5 mL) at 0° C. was treated with sodium cyanoborohydride (65 mg, 1.03 mmol) and 37% formalin (1.0 mL), warmed to room temperature, stirred for 1 hour, treated with water, and extracted with dichloromethane. The combined extracts were washed with brine, dried (MgSO$_4$), filtered, and concentrated to provide the desired product.

MS (DCI/NH$_3$) m/e 353 (M+H)$^+$.

EXAMPLE 30K 6-(2-(1,2-dimethyl-1,2,3,4-tetrahydro-7-isoquinolinyl)cyclopropyl)-2-naphthalenecarboximidamide The desired product was prepared by substituting Example 30J for Example 1M in Example 1N.

MS (ESI(+)) m/e 370 (M+H)$^+$;

$^1$H NMR (300 MHz, DMSO-d$_6$) δ9.41 (s, 2H), 9.23 (s, 2H), 8.45 (s, 1H), 8.05 (d, 1H), 8.02 (d, 1H), 7.85 (s, 1H), 7.80 (dd, 1H), 7.51 (dd, 1H), 7.15 (m, 3H), 4.63–4.47 (m, 1H), 3.72–3.63 (m, 1H), 3.47 (m, 1H), 3.02 (m, 2H), 2.91 (s, 2H), 2.83 (d, 1H), 2.41 (m, 2H), 1.64 (m, 3H), 1.53 (t, 2H);

Anal. calcd. for C$_{25}$H$_{27}$N$_3$.2CF$_3$COOH.H$_2$O: C, 56.58; H, 5.08; N, 6.83. Found: C, 56.84; H, 4.90; N, 6.85.

EXAMPLE 31

6-(2-(4,4-diethyl-1-isopropyl-3,4-dihydro-6-isoquinolinyl)cyclopropyl)-2-naphthalenecarboximidamide

EXAMPLE 31A 2-(3-bromophenyl)-2-ethylbutanenitrile

A solution of (3-bromophenyl)acetonitrile (250 mg, 1.27 mmol) and ethyl iodide (0.22 mL, 2.78 mmol) in dichloromethane (1.3 mL) at room temperature was treated with 10% NaOH (1.3 mL) and tetrabutylammonium hydrogen sulfate (0.47 g, 1.39 mmol), stirred for 24 hours, treated with water, and extracted with dichloromethane. The combined extracts were concentrated and the concentrate was purified by flash column chromatography on silica gel with hexanes to provide the desired product.

MS (DCI/NH$_3$) m/e 251 (M+H)$^+$.

EXAMPLE 31B 2-(3-bromophenyl)-2-ethyl-1-butanamine

A solution of Example 31A (4.75 g, 18.9 mmol) in THF (80 mL) was treated with 1M BH$_3$ in THF (80 mL), heated to reflux, stirred for 2.5 hours, cooled to 0° C., and treated with methanol (20 mL). The mixture was concentrated, treated with methanolic HCl (80 mL), heated to reflux, stirred for 1.5 hours, cooled to room temperature, and concentrated. The concentrate was treated with toluene and concentrated to provide the desired product.

MS (DCI/NH$_3$) m/e 256 (M+H)$^+$.

EXAMPLE 31 C 6-bromo-4,4-diethyl-1-isopropyl-3,4-dihydroisoquinoline

The desired product was prepared by substituting Example 31B for 2-(4-bromophenyl)ethylamine in Example 1I.

MS (DCI/NH$_3$) m/e 308 (M+H)$^+$.

EXAMPLE 31D 4,4-diethyl-1-isopropyl-3,4-dihydro-6-isoquinolinecarbaldehyde

The desired product was prepared by substituting Example 31C for Example 1I in Example 1J.

MS (DCI/NH$_3$) m/e 258 (M+H)$^+$.

EXAMPLE 31E 6-(2-(4,4-diethyl-1-isopropyl-3,4-dihydro-6-isoquinolinyl)ethenyl)-2-naphthonitrile The desired product was prepared by substituting Example 31D and Example 42C for Example 1J and Example 1H, respectively, in Example 1K.

MS (DCI/NH$_3$) m/e 407 (M+H)$^+$.

EXAMPLE 31F 6-(2-(4,4-diethyl-1-isopropyl-3,4-dihydro-6-isoquinolinyl)cyclopropyl)-2-naphthonitrile The desired product was prepared by substituting Example 31E for Example 1L in Example 1M.

MS (DCI/NH$_3$) m/e 421 (M+H)$^+$.

EXAMPLE 31G 6-(2-(4,4-diethyl-1-isopropyl-3,4-dihydro-6-isoquinolinyl)cyclopropyl)-2-naphthalenecarboximidamide The desired product was prepared by substituting Example 31F for Example 1M in Example 1N.

MS (ESI(+)) m/e 438 (M+H)$^+$;

$^1$H NMR (300 MHz, DMSO-d$_6$) δ12.31 (s, 1H), 9.43 (s, 2H), 9.26 (s, 2H), 8.47 (s, 1H), 8.14 (d, 1H), 8.06 (d, 2H), 7.91 (s, 1H), 7.81 (dd, 1H), 7.54 (dd, 1H), 7.44 (s, 1H), 7.39 (d, 1H), 3.86 (m, 1H), 1.92–1.82 (m, 2H), 1.80–1.60 (m, 4H), 1.32 (d, 6H), 0.78 (t, 3H); 0.74 (t, 3H);

Anal. calcd. for $C_{30}H_{35}N_3 \cdot 2CF_3CO_2H \cdot H_2O$: C, 59.73; H, 5.75; N, 6.15. Found: C, 59.70; H, 5.32; N, 6.01.

EXAMPLE 32

6-(2-(4,4-diethyl-1-isopropyl-2-methyl-1,2,3,4-tetrahydro-6-isoquinolinyl)cyclopropyl)-2-naphthalenecarboximidamide

EXAMPLE 32A 6-(2-(4,4-diethyl-1-isopropyl-2-methyl-1,2,3,4-tetrahydro-6-isoquinolinyl)cyclopropyl)-2-naphthonitrile A solution of Example 31F (200 mg, 0.48 mmol) in methanol (2.5 mL) at room temperature was treated with sodium cyanoborohydride (61 mg, 0.95 mmol), 37% formalin (0.19 mL), and glacial acetic acid (4 drops). The mixture was stirred for 2 hours, treated with water, adjusted to pH>7 with 1M KOH, and extracted with dichloromethane. The combined extracts were washed with water, dried (MgSO$_4$), filtered, and concentrated to provide the desired product.

MS (DCI/NH$_3$) m/e 437 (M+H)$^+$.

EXAMPLE 32B 6-(2-(4,4-diethyl-1-isopropyl-2-methyl-1,2,3,4-tetrahydro-6-isoquinolinyl)cyclopropyl)-2-naphthalenecarboximidamide The desired product was prepared by substituting Example 32A for Example 1M in Example 1N.

MS (ESI(+)) m/e 454 (M+H)$^+$;

$^1$H NMR (300 MHz, DMSO-d$_6$) δ9.41 (s, 2H), 9.17 (s, 2H), 8.45 (s, 1H), 8.05 (dd, 2H), 7.87 (s, 1H), 7.80 (dd, 1H), 7.52 (dd, 1H), 7.25 (d, 1H), 7.18–7.09 (m, 2H), 4.33 (m, 0.5H), 4.19 (m, 0.5H), 3.24–3.17 (m, 1H), 3.01 (s, 3H), 2.47 (m, 2.5H), 2.27, (m, 0.5H), 1.91–1.75 (m, 2H), 1.69 (m, 4H), 1.26–1.15 (m, 3H), 0.90–0.70 (m, 9H);

Anal. calcd. for $C_{31}H_{39}N_3 \cdot 2CF_3CO_2H \cdot 0.5H_2O$: C, 60.86; H, 6.13; N, 6.08. Found: C, 60.99; H, 6.11; N, 5.97.

EXAMPLE 33

6-(2-(1-isopropyl-2-(2,2,2-trifluoroethyl)-1,2,3,4-tetrahydro-7-isoquinolinyl)cyclopropyl)-2-naphthalenecarboximidamide

EXAMPLE 33A 6-(2-(1-isopropyl-2-(2,2,2-trifluoroethyl)-1,2,3,4-tetrahydro-7-isoquinolinyl)cyclopropyl)-2-naphthonitrile A solution of 2,2,2-trifluoroethanol (0.88 mL, 12 mmol) and pyridine (0.9 mL, 12 mmol) in dichloromethane (10 mL) at 0° C. was treated dropwise with trifluoromethanesulfonic anhydride (2.0 mL, 12 mmol), stirred for 15 minutes, warmed to room temperature, and stirred for 18 hours. The solution (0.7 mL, 0.84 mmol) was added dropwise to a mixture of Example 20A (150 mg, 0.41 mmol) and K$_2$CO$_3$ (172 mg, 1.2 mmol) in DMF (1.1 mL), stirred for 24 hours, treated with water, and extracted with dichloromethane. The combined extracts were washed with brine, dried (MgSO$_4$), filtered, and concentrated. The concentrate was purified by flash column chromatography on silica gel using 10% ethyl acetate/hexanes to provide the desired product.

MS (DCI/NH$_3$) m/e 449 (M+H)$^+$.

EXAMPLE 33B 6-(2-(1-isopropyl-2-(2,2,2-trifluoroethyl)-1,2,3,4-tetrahydro-7-isoquinolinyl)cyclopropyl)-2-naphthalenecarboximidamide The desired product was prepared by substituting Example 33A for Example 1M in Example 1N.

MS (ESI(+)) m/e 466 (M+H)$^+$:

$^1$H NMR (300 MHz, DMSO-d$_6$) δ9.40 (s, 2H), 9.08 (s, 2H), 8.44 (s, 1H), 8.05–8.00 (m, 2H), 7.85 (s, 1H), 7.80–7.76 (m, 1H), 7.53–7.48 (m, 1H), 7.06–6.96 (m, 2H), 6.92 (d, 1H), 3.40 (m, 2H), 3.32–3.19 (m, 3H), 3.07–2.82 (m, 3H), 2.49 (m, 1H), 2.37–2.30 (m, 1H), 1.87–1.80 (m, 1H), 1.63 (t, 1H), 1.01 (dd, 3H), 0.87 (dd, 3H);

Anal. calcd. for $C_{28}H_{30}F_3N_3 \cdot 2CF_3CO_2H$: C, 62.17; H, 5.39; N, 7.25. Found: C, 62.10; H, 5.52; N, 6.89.

EXAMPLE 34

8-((1E)-3,3-dimethyl-1-butenyl)-6-(2-(1-isopropyl-3,4-dihydro-7-isoquinolinyl)cyclopropyl)-2-naphthalenecarboximidamide

EXAMPLE 34A 2-((1E)-3,3-dimethyl-1-butenyl)-4,4,5,5-tetramethyl-1,3,2-dioxaborolane The desired product was prepared by substituting 3,3-dimethyl-1-butyne for 3-methoxy-1propyne in Example 4B.

EXAMPLE 34B 8-((1E)-3,3-dimethyl-1-butenyl)-6-(2-(1-isopropyl-3,4-dihydro-7-isoquinolinyl)cyclopropyl)-2-naphthonitrile The desired product was prepared by substituting Example 34A for Example 4B in Example 4C.

MS (APCI(+)) m/e 447 (M+H)$^+$.

EXAMPLE 34C 8-((1E)-3,3-dimethyl-1-butenyl)-6-(2-(1-isopropyl-3,4-dihydro-7-isoquinolinyl)cyclopropyl)-2-naphthalenecarboximidamide The desired product was prepared by substituting Example 34B for Example 1M in Example 1N.

MS (APCI(+)) m/e 464 (M+H)$^+$;

$^1$NMR (300 MHz, DMSO-d$_6$) δ9.47 (s, 2H), 9.13 (s, 2H), 8.60 (s, 1H), 8.04 (d, 1H), 7.98 (s, 1H), 7.80 (dd, 1H), 7.74 (s, 1H), 7.63 (d, 1H), 7.58 (s, 1H), 7.48 (d, 1H), 7.17 (d, 1H), 6.53 (d, 1H), 3.84–3.78 (m, 1H), 3.07–3.05 (m, 2H), 2.58–2.55 (m, 2H), 1.87–1.70 (m, 2H), 1.38–1.36 (m, 1H), 1.31 (dd, 6H), 1.26–1.22 (m, 1H), 1.21 (s, 9H);

Anal. calcd. for $C_{32}H_{37}N_3 \cdot 2.2CF_3CO_2H$: C, 59.70; H, 5.74; N, 6.11. Found: C, 60.16; H, 5.67; N, 5.62.

EXAMPLE 35

8-bromo-6-(2-(1-isopropyl-3,4-dihydro-7-isoquinolinyl)cyclopropyl)-2-naphthalenecarboximidamide The desired product was prepared by substituting Example 4A for Example 1M in Example 1N.

MS (APCI(+)) m/e 460 (M+H)$^+$;

$^1$H NMR (300 MHz, DMSO-d$_6$) δ9.55 (s, 2H), 9.18 (s, 2H), 8.53 (s, 1H), 8.12 (d, 1H), 7.99 (s, 1H), 7.94 (s, 1H), 7.92 (s, 1H), 7.87 (dd, 1H), 7.63 (dd, 1H), 7.48 (d, 1H), 3.92–3.87 (m, 2H), 3.82 (dd, 2H), 3.06 (dd, 2H), 2.61–2.55 (m, 1H), 1.82–1.76 (m, 2H), 1.33 (d, 3H), 1.31 (d, 3H);

Anal. calcd. for C$_{26}$H$_{26}$BrN$_3$.2.3CF$_3$CO$_2$H: C, 48.90; H, 4.10; N, 6.05. Found: C, 49.11; H, 3.79; N, 5.53.

EXAMPLE 36

8-bromo-6-(2-(1-isopropyl-2-methyl-1,2,3,4-tetrahydro-7-isoquinolinyl)cyclopropyl)-2-naphthalenecarboximidamide The desired product was prepared by substituting Example 41A for Example 1M in Example 1N.

MS (APCI(+)) m/e 476 (M+H)$^+$;

$^1$H NMR (300 MHz, DMSO-d$_6$) δ10.27 (br s, 1H), 9.61 (s, 2H), 9.27 (s, 2H), 8.53 (m, 1H), 8.11 (dd, 1H), 7.92–7.86 (m, 3H), 7.24–7.14 (m, 2H), 7.05–7.03 (m, 1H), 3.65–3.55 (m, 1H), 3.25–3.15 (m, 1H), 3.10–3.05 (m, 1H), 3.05–2.95 (m, 2H), 2.85–2.35 (m, 1H), 2.84–2.78 (m, 3H), 2.30–2.15 (m, 1H), 1.73–1.68 (m, 2H), 1.21–1.18 (m, 1H), 1.16–1.11 (m, 3H), 0.88–0.82 (m, 3H);

Anal. calcd. for C$_{27}$H$_{30}$BrN$_3$.2.1HCl: C, 58.64; H, 5.85; N, 7.60. Found: C, 58.43; H, 6.14; N, 7.54.

EXAMPLE 37

6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide

EXAMPLE 37A 4,4,5,5-tetramethyl-2-((1E)-3-methyl-1-butenyl)-1,3,2-dioxaborolane The desired product was prepared by substituting 3-methyl-1-butyne for 3-methoxy-1-propyne in Example 4B.

EXAMPLE 37B 6-(2-(1-isopropyl-2-methyl-1,2,3,4-tetrahydro-7-isoquinolinyl)cyclopropyl)-8-((1E)-3-methyl-1-butenyl)-2-naphthonitrile The desired product was prepared by substituting Example 41A and Example 37A for Example 4A and Example 4B, respectively, in Example 4C.

MS (APCI(+)) m/e 449 (M+H)$^+$.

EXAMPLE 37C 6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide The desired product was prepared by substituting Example 37B for Example 1M in Example 1N.

MS (APCI(+)) m/e 466 (M+H)$^+$;

$^1$NMR (300 MHz, DMSO-d$_6$) δ9.51 (s, 2H), 9.13 (s, 2H), 8.66 (s 1H), 8.02 (dd, 1H), 7.82 (d, 1H), 7.74 (s, 1H), 7.60–7.59 (m, 1H), 7.30–7.14 (m, 3H), 7.04 (d, 1H), 6.52–6.43 (m, 1H), 3.65–3.55 (m, 1H), 3.25–3.15 (m, 1H), 3.02–2.98 (m, 2H), 2.82–2.78 (m, 3H), 2.62 (dd, 1H), 2.54–2.46 (m, 1H), 2.40–2.35 (m, 1H), 2.30–2.15 (m, 1H), 1.74–1.63 (m, 2H), 1.60–1.52 (m, 1H), 1.22–1.10 (m, 9H), 0.85 (d, 3H);

Anal. calcd. for C$_{32}$H$_{39}$N$_3$.2CF$_3$CO$_2$H: C, 60.98; H, 6.17; N, 6.27. Found: C, 60.69; H, 5.83; N, 6.10.

EXAMPLE 38

6-(2-(1-isopropyl-2-methyl-1,2,3,4-tetrahydro-7-isoquinolinyl)cyclopropyl)-8-((1E)-3-methyl-1,3-butadienyl)-2-naphthalenecarboximidamide

EXAMPLE 38A 8-((1E)-3-hydroxy-3-methyl-1-butenyl)-6-(2-(1-isopropyl-2-methyl-1,2,3,4-tetrahydro-7-isoquinolinyl)cyclopropyl)-2-naphthonitrile A solution of Example 41A (224 mg, 0.50 mmol) in acetonitrile (5 mL) was treated with 2-methyl-3-buten-2-ol (175 mg, 2.0 mmol), Pd(OAc)$_2$ (11 mg, 0.05 mmol), tri-o-tolylphosphine (30 mg, 0.10 mmol), and triethylamine (76 mg, 0.75 mmol), flushed with argon, sealed in a tube, and heated to 100° C. for 24 hours. The mixture was diluted with ethyl acetate (10 mL), filtered, and concentrated. The concentrate was purified by flash column chromatography on silica gel with 10% methanol/dichloromethane to provide the desired product.

MS (APCI(+)) m/e 465 (M+H)$^+$.

EXAMPLE 38B 6-(2-(1-isopropyl-2-methyl-1,2,3,4-tetrahydro-7-isoquinolinyl)cyclopropyl)-8-((1E)-3-methyl-1,3-butadienyl)-2-naphthalenecarboximidamide The desired product was prepared by substituting Example 38A for Example 1M in Example 1N, then dissolving the resulting product in a 1:1 mixture of acetonitrile:water containing 0.1% TFA. The mixture was concentrated and purified as in Example 1N to provide the desired product.

MS (APCI(+)) m/e 464 (M+H)$^+$;

$^1$H NMR (300 MHz, DMSO-d$_6$) δ9.45 (br s, 2H), 9.30 (br s, 1H), 9.05 (br s, 2H), 8.68 (s, 1H), 8.04 (dd, 1H), 7.82 (s, 1H), 7.80–7.78 (m, 1H), 7.71–7.70 (m, 1H), 7.44 (m, 1H), 7.26–7.17 (m, 3H), 7.05 (dd, 1H), 4.26 (m, 2H), 3.10–2.90 (m, 2H), 2.85–2.81 (m, 3H), 2.51–2.49 (m, 3H), 2.15–2.10 (m, 1H), 2.10 (s, 3H), 1.79–1.27 (series of m, 4H), 1.10 (dd, 3H), 0.84 (dd, 3H).

EXAMPLE 39

8-cyclopropyl-6-(2-(1-isopropyl-2-methyl-1,2,3,4-tetrahydro-7-isoquinolinyl)cyclopropyl)-2-naphthalenecarboximidamide

EXAMPLE 39A 8-cyclopropyl-6-(2-(1-isopropyl-2-methyl-1,2,3,4-tetrahydro-7-isoquinolinyl)cyclopropyl)-2-naphthonitrile A solution of Example 41B (250 mg, 0.61 mmol) in THF (50 mL) at 0° C. was treated with Pd(OAc)$_2$ (14 mg) and 0.68M diazomethane in ether (23 mL) portionwise. The mixture was stirred for 1 hour, filtered, and concentrated. The concentrate was purified by flash column chromatography on silica gel with 10% methanol/dichloromethane to provide the desired product MS (APCI(+)) m/e 421 (M+H)$^+$. .

EXAMPLE 39B 8-cyclopropyl-6-(2-(1-isopropyl-2-methyl-1,2,3,4-tetrahydro-7-isoquinolinyl)cyclopropyl)-2-naphthalenecarboximidamide The desired product was prepared by substituting Example 39A for Example 1M in Example 1N.

MS (APCI(+)) m/e 438 (M+H)$^+$;

$^1$NMR (300 MHz, DMSO-d$_6$) δ9.45 (br s, 2H), 9.39 (br s, 1H), 9.14 (br s, 2H), 8.34 (s, 1H), 8.03 (dd, 1H), 7.81 (d, 1H), 7.66 (s, 1H), 7.25–7.14 (m, 3H), 7.03 (dd, 1H), 3.29–3.27 (m, 1H), 3.00 (m, 1H), 2.85–2.81 (m, 2H), 2.56–2.52 (m, 1H), 2.50 (s, 3H), 2.45–2.43 (m, 1H), 1.71–1.66 (m, 2H), 1.53–1.48 (m, 1H), 1.12–1.08 (m, 5H), 0.86–0.81 (m, 7H).

EXAMPLE 40

6(2-(1-isopropyl-2-methyl-1,2,3,4-tetrahydro-7-isoquinolinyl)cyclopropyl)-8-(2-methoxyphenyl)-2-naphthalenecarboximidamide

EXAMPLE 40A 6-(2-(1-isopropyl-2-methyl-1,2,3,4-tetrahydro-7-isoquinolinyl)cyclopropyl)-8-(2-methoxyphenyl)-2-naphthonitrile The desired product was prepared by substituting Example 41A and 2-methoxyphenylboronic acid for Example 4A and Example 4B, respectively, in Example 4C.

MS (APCI(+)) m/e 487 (M+H)$^+$.

EXAMPLE 40B 6-(2-(1-isopropyl-2-methyl-1,2,3,4-tetrahydro-7-isoquinolinyl)cyclopropyl)-8-(2-methoxyphenyl)-2-naphthalenecarboximidamide The desired product was prepared by substituting Example 40A for Example 1M in Example 1N.

MS (APCI(+)) m/e 503 (M+H)$^+$;

$^1$H NMR (300 MHz, DMSO-d$_6$) δ9.63 (br s, 1H), 9.30 (br s, 2H), 9.20 (br s, 2H), 8.08 (dd, 1H), 7.88 (s, 1H), 7.85 (s, 1H), 7.76 (d, 1H), 7.51 (m, 1H), 7.33 (s, 2H), 7.24–7.11 (m, 4H), 7.05 (d, 1H), 3.66 (s, 3H), 3.28–3.27 (m, 1H), 3.03–2.99 (m, 2H), 2.83 (s, 3H), 2.50–2.49 (m, 1H), 2.40–2.39 (m, 1H), 2.19–2.14 (m, 1H), 1.72–1.64 (m, 2H), 1.53–1.52 (m, 1H), 1.19–1.15 (m, 1H), 1.10 (dd, 3H), 0.83 (dd, 3H);

Anal. calcd. for $C_{34}H_{37}N_3O.2.5CF_3CO_2H$: C, 57.78; H, 5.25; N, 5.54. Found C, 57.73; H, 4.97; N, 5.12.

EXAMPLE 41

6-(2-(1-isopropyl-2-methyl-1,2,3,4-tetrahydro-7-isoquinolinyl)cyclopropyl)-8-vinyl-2-naphthalenecarboximidamide

EXAMPLE 41A 8-bromo-6-(2-(1-isopropyl-2-methyl-1,2,3,4-tetrahydro-7-isoquinolinyl)cyclopropyl)-2-naphthonitrile The desired product was prepared by substituting Example 4A for Example 31F in Example 32A.

MS (APCI(+)) m/e 459 (M+H)$^+$.

EXAMPLE 41B 6-(2-(1-isopropyl-2-methyl-1,2,3,4-tetrahydro-7-isoquinolinyl)cyclopropyl)-8-vinyl-2-naphthonitrile A solution of Example 41A (430 mg, 0.94 mmol) in toluene (10 mL) was treated with tributyl(vinyl)stannane (298 mg, 0.94 mmol), and Pd(PPh$_3$)$_4$ (109 mg, 0.09 mmol), flushed with argon, sealed in a tube, and heated to 100° C. for 20 hours. The mixture was cooled to room temperature, treated with ethyl acetate (10 mL), filtered, and concentrated. The concentrate was purified by flash column chromatography on silica gel with 10% methanol/dichloromethane to provide the desired product.

MS (APCI(+)) m/e 407 (M+H)$^+$.

EXAMPLE 41C 6-(2-(1-isopropyl-2-methyl-1,2,3,4-tetrahydro-7-isoquinolinyl)cyclopropyl)-8-vinyl-2-naphthalenecarboximidamide The desired product was prepared by substituting Example 41B for Example 1M in Example 1N.

MS (APCI(+)) m/e 424 (M+H)$^+$.

EXAMPLE 42 methyl 6-(2-(6-(amino(hydroxyimino)methyl)-2-naphthyl)ethenyl)-3,4-dihydro-2(1H)-isoquinolinecarboxylate

EXAMPLE 42A 6-(hydroxymethyl)-2-naphthonitrile

A solution of Example 1D (14.5 g, 68.6 mmol) in THF (350 mL) at room temperature was treated with a solution of calcium chloride (15.2 g) in ethanol (350 mL) and sodium borohydride (10.38 g). The mixture was stirred for 16 hours, treated sequentially with water, 10% KHSO$_3$, and 1M HCl, and extracted with dichloromethane. The combined extracts were washed with water and brine, dried (MgSO$_4$), filtered, and concentrated. The concentrate was recrystallized from ether/hexanes to provide the desired product.

MS (DCI/NH$_3$) m/e 184 (M+H)$^+$.

EXAMPLE 42B 6-(bromomethyl)-2-naphthonitrile

A solution of Example 42A (2.7 g, 14.7 mmol) in THF (80 mL), at room temperature was treated with carbon tetrabromide (6.85 g) and triphenylphosphine (4.83 g), stirred for 16 hours, and concentrated. The concentrate was purified by flash column chromatography on silica gel with 50% dichloromethane/hexanes to provide the desired product.

MS (DCI/NH$_3$) m/e 246 (M+H)$^+$.

EXAMPLE 42C diethyl (6-cyano-2-naphthyl)methylphosphonate

A suspension of Example 42B (3.0 g, 12.2 mmol) in triethylphosphite (3.0 mL) was heated to 150° C., stirred for 3 hours, cooled to room temperature, and treated with diethyl ether and hexanes. The resulting precipitate was collected by filtration and dried to provide the desired product MS (DCI/NH$_3$) m/e 304 (M+H)$^+$. .

EXAMPLE 42D 1,2,3,4-tetrahydro-6-isoquinolinol

A solution of boron tribromide (1.2 mL, 12.5 mmol) in dichloromethane (12.5 mL) was added dropwise to a −78° C. solution of 6-methoxytetrahydroisoquinoline (1.0 g, 5.0 mol, prepared as described in Org. Synth 1988, 67, 60) in dichloromethane (38 mL). The mixture was stirred for 1 hour, warmed to 0° C., stirred for 1 hour, warmed to room temperature, and stirred for 1 hour. The mixture was cooled to −78° C., treated dropwise with methanol (20 mL), warmed to room temperature, stirred for 1 hour, and concentrated to provide the desired product.

MS (DCI/NH$_3$) m/e 150 (M+H)$^+$.

EXAMPLE 42E tert-butyl 6-hydroxy-3,4-dihydro-2(1H)-isoquinolinecarboxylate

Example 42D (1.15 g, 5.0 mmol) and di-tert-butyldicarbonate were processed according to the procedure described in Synthesis, 1986, 48. A portion of the resulting product (2.1 g) was stirred at reflux for 1.5 hour with 60 mL methanol and 9 mL 10% aqueous NaOH. After cooling to room temperature the mixture was concentrated, treated with water, adjusted to pH<7 with 1M HCl, and extracted with dichloromethane. The combined extracts were washed with water and brine, dried (MgSO$_4$), filtered, and concentrated to provide the desired product.

MS (DCI/NH$_3$) m/e 267 (M+NH$_4$)$^+$.

EXAMPLE 42F tert-butyl 6-((trifluoroacetyl)oxy)-3,4-dihydro-2(1H)-isoquinolinecarboxylate A solution of Example 42E (1.0 g, 4.0 mmol) and triethylamine (0.5 mL, 4.0 mmol) in dichloromethane (20 mL) at 0° C. was treated dropwise with trifluoromethanesulfonic anhydride (1.12 g, 4.0 mmol), warmed to room temperature, stirred for 48 hours, concentrated, dissolved in ethanol (10 mL), triturated with water, and filtered to provide the desired product.

MS (DCI/NH$_3$) m/e 382 (M+H)$^+$.

EXAMPLE 42G tert-butyl 6-((methoxy(methyl)amino)carbonyl)-3,4-dihydro-2(1H)-isoquinolinecarboxylate A solution of Example 42F (1.4 g, 4.60 mmol) in THF (40 mL) and water (5 mL) was treated with triethylamine (0.63 g) and PdCl$_2$(dppf) (0.28 g) and stirred under 400 psi of carbon monoxide at 115° C. for 18 hours. The mixture was filtered, concentrated, treated sequentially with diisopropylethylamine (2 mL), N,O-dimethylhydroxylamine hydrochloride (750 mg), and (O-(7-azabenzotriazol-1-yl)-1,1,3,3-tetramethyluronium hexafluorophosphate) (1.5 g), and stirred for 16 hours. The mixture was treated with dichloromethane, washed sequentially with 3% HCl, water, and 1M NaOH, dried (MgSO$_4$), filtered, and concentrated. The concentrate was purified by flash column chromatography with 50% ethyl acetate/hexanes to provide the desired product.

MS (DCI/NH$_3$) m/e 293 (M+H)$^+$.

EXAMPLE 42H tert-butyl 6-formyl-3,4-dihydro-2(1H)-isoquinolinecarboxylate

A solution of Example 42G (5.6 g, 19.1 mmol), in THF (95 mL) at 0° C. was treated with 1M LAH in THF (18 mL, 18 mmol), stirred for 30 minutes, quenched with 10% KHSO$_3$, diluted with ethyl acetate and adjusted to pH 2 with1M HCl. The extract was washed with water and brine, dried (MgSO$_4$), filtered, and concentrated. The concentrate was purified by flash column chromatography on silica gel with dichloromethane to provide the desired product.

MS (DCI/NH$_3$) m/e 262 (M+H)$^+$.

EXAMPLE 42I tert-butyl 6-(2-(6-cyano-2-naphthyl)ethenyl)-3,4-dihydro-2(1H)-isoquinolinecarboxylate A solution of Example 42C (2.3 g, 7.60 mmol) in THF (100 mL) at 0° C. was treated with 1M LiHMDS in hexanes (9.5 mL, 9.5 mmol), stirred for 40 minutes, treated with Example 42H (1.98 g, 26 mmol), and warmed to room temperature over 50 minutes. The mixture was quenched with water and extracted with dichloromethane. The combined extracts were washed with water and brine, dried (MgSO$_4$), filtered, and concentrated. The concentrate was purified by flash column chromatography on silica gel with dichloromethane to provide the desired product.

MS (ESI(+)) m/e 411 (M+H)$^+$.

EXAMPLE 42J 6-(2-(1,2,3,4-tetrahydro-6-isoquinolinyl)ethenyl)-2-naphthonitrile A solution of Example 42I (2.28 g, 0.55 mmol) in 1:1 dichloromethane:TFA (10 mL) at room temperature was stirred for 1 hour, then concentrated to provide the desired product.

MS (ESI(+)) m/e 311 (M+H)$^+$.

EXAMPLE 42K methyl 6-(2-(6-cyano-2-naphthyl)ethenyl)-3,4-dihydro-2(1H)-isoquinolinecarboxylate A solution of Example 42J (650 mg, 1.53 mmol) in dioxane (30 mL) at room temperature was treated with 10% K$_2$CO$_3$ (10 mL) and methyl chloroformate (700 mg) and stirred for 16 hours. The mixture was treated with water and extracted with dichloromethane. The combined extracts were washed sequentially with 5% HCl, water, and brine, dried (MgSO$_4$), filtered, and concentrated. The concentrate was purified by flash column chromatography on silica gel with dichloromethane to provide the desired product.

MS (ESI(+)) m/e 369 (M+H)$^+$.

EXAMPLE 42L methyl 6-(2-(6-amino(hydroxyimino)methyl)-2-naphthyl)ethenyl)-3,4-dihydro-2(1H)-isoquinolinecarboxylate A solution of Example 42K (150 mg, 0.4 mmol) in ethanol (2 mL), was treated with triethylamine (0.5 mL) and hydroxylamine hydrochloride (283 mg), then sealed in a tube, heated to 80° C., stirred for 2.5 hours, and cooled to room temperature. The resulting precipitate was collected by filtration, washed with ethanol, and dried to provide the desired product.

MS (ESI(+)) m/e 402 (M+H)$^+$;

$^1$H NMR (300 MHz, DMSO-d$_6$) δ9.80 (s, 1H), 8.18 (s, 1H), 8.00 (s, 1H), 7.91–7.85 (m, 4H), 7.50–7.39 (m, 3H), 7.24–7.21 (m, 2H), 5.93 (s, 2H), 4.57 (s, 2H), 3.65 (s, 3H), 3.63 (t, 2H), 2.85 (t, 2H);

Anal. calcd. for C$_{24}$H$_{23}$N$_3$O$_3$·0.3H$_2$O: C, 70.85; H, 5.85; N, 10.33. Found: C, 70.85; H, 5.66; N, 10.27.

EXAMPLE 43

6-(2-(2-acetyl-1,2,3,4-tetrahydro-6-isoquinolinyl) ethenyl)-N'-hydroxy-2-naphthalenecarboximidamide

EXAMPLE 43A 6-(2-(2-acetyl-1,2,3,4-tetrahydro-6-isoquinolinyl) ethenyl)-2-naphthonitrile The desired product was prepared by substituting acetyl chloride for methyl chloroformate in Example 42K.

MS (DCI/NH$_3$) m/e 353 (M+H)$^+$.

EXAMPLE 43B 6-(2-(2-acetyl-1,2,3,4-tetrahydro-6-isoquinolinyl) ethenyl)-N'-hydroxy-2-naphthalenecarboximidamide The desired product was prepared by substituting Example 43A for Example 42K in Example 42L.

MS (ESI(+)) m/e 386 (M+H)$^+$;

$^1$H NMR (300 MHz, DMSO-d$_6$) δ9.8 (s, 1H), 8.18 (s, 1H), 8.00 (s, 1H), 7.95–7.85 (m, 4H), 7.52–7.40 (m, 3H), 7.24–7.21 (m, 2H), 5.93 (s, 2H), 4.66–4.60 (m, 2H), 3.68 (t, 2H), 2.92–2.78 (m, 2H), 2.10 (s, 3H);

Anal. calcd. for C$_{24}$H$_{23}$N$_3$O$_2$·0.2H$_2$O: C, 74.09; H, 6.06; N, 10.80. Found: C, 74.05; H, 6.06; N, 10.55.

EXAMPLE 44

6-(2-(2-acetyl-1,2,3,4-tetrahydro-6-isoquinolinyl) ethenyl)-2-naphthalenecarboximidamide The desired product was prepared by substituting Example 43A for Example 1M in Example 1N.

MS (ESI(+)) m/e 371 (M+H)$^+$;

$^1$H NMR (300 MHz, DMSO-d$_6$) δ9.42 (s, 2H), 9.00 (s, 2H), 8.45 (s, 1H), 8.15–8.02 (m, 4H), 7.83–7.79 (m, 1H), 7.54–7.48 (m, 4H), 7.25 (d, 1H), 4.67–4.62 (m, 2H), 3.69 (t, 2H), 2.94–2.80 (m, 2H), 2.10 (s, 3H);

Anal. calcd. for C$_{24}$H$_{23}$N$_3$O·CF$_3$CO$_2$H: C, 64.59; H, 5.00; N, 8.69. Found: C, 64.69; H, 4.98; N, 8.76.

EXAMPLE 45

N'-hydroxy-6-(2-(1,2,3,4-tetrahydro-6-isoquinolinyl) ethenyl)-2-naphthalenecarboximidamide

EXAMPLE 45A tert-butyl 6-(2-(6-amino(hydroxyimino)methyl)-2-naphthyl)ethenyl)-3,4-dihydro-2(1H)-isoquinolinecarboxylate The desired product was prepared by substituting Example 42I for Example 42K in Example 42L.

MS (DCI/NH$_3$) m/e 444 (M+H)$^+$.

EXAMPLE 45B

N'-hydroxy-6-(2-(1,2,3,4-tetrahydro-6-isoquinolinyl) ethenyl)-2-naphthalenecarboximidamide The desired product was prepared by substituting Example 45A for Example 42I in Example 42J.

MS (ESI(+)) m/e 344 (M+H)$^+$;

$^1$H NMR (300 MHz, DMSO-d$_6$) δ10.9 (br s, 1H), 9.06, (br s, 3H), 8.30 (s, 1H), 8.10 (s, 1H), 8.05–7.96 (m, 3H), 7.80–7.76 (m, 1H), 7.59–7.48 (m, 4H), 7.27 (d, 1H), 4.31 (br s, 2H), 3.60–3.40 (br s, 4H), 3.05 (t, 2H);

Anal. calcd. for C$_{22}$H$_{21}$N$_3$O·CF$_3$CO$_2$H: C, 54.64; H, 4.06; N, 7.35. Found: C, 54.10; H, 4.06; N, 7.25.

EXAMPLE 46

6-(2-(1,2,3,4-tetrahydro-6-isoquinolinyl) cyclopropyl)-2-naphthalenecarboximidamide

EXAMPLE 46A tert-butyl 6-(2-(6-cyano-2-naphthyl)cyclopropyl)-3,4-dihydro-2(1H)-isoquinolinecarboxylate A solution of Example 42I (207 mg, 0.5 mmol) and Pd(OAc)$_2$ (5 mg) in THF (100 mL), at 0° C. was treated with a 0° C. 2M solution of diazomethane in diethyl ether (20 mL), warmed to room temperature over 10 minutes, treated with Pd(OAc)$_2$ (5 mg) and 2M diazomethane in diethyl ether (20 mL), and treated two more times with Pd(OAc)$_2$ and 2M diazomethane after 10 minute stirring intervals. After the final addition, the mixture was stirred for 1 hour, filtered through diatomaceous earth (Celite®) and concentrated. The concentrate was purified by flash column chromatography on silica gel with 10% ethyl acetate/hexanes to provide the desired product.

MS (DCI/NH$_3$) m/e 425 (M+H)$^+$.

EXAMPLE 46B 6-(2-(1,2,3,4-tetrahydro-6-isoquinolinyl) cyclopropyl)-2-naphthalenecarboximidamide The desired product was prepared by substituting Example 46A for Example 1M in Example 1N, then substituting the resulting product for Example 42I in Example 42J.

MS (ESI(+)) m/e 342 (M+H)$^+$;

1H NMR (300 MHz, DMSO-d$_6$) δ9.39 (s, 2H), 9.14 (s, 2H), 9.03 (br. s, 2H), 8.45 (s, 1H), 8.04–8.00 (m, 2H), 7.84 (s, 1H), 7.81–7.77 (m, 1H), 7.52–7.49 (m, 1H), 7.16–7.09 (m, 2H), 4.25 (br s, 2H), 2.97 (t, 2H), 2.42–2.35 (m, 2H), 1.68–1.59 (m, 2H);

Anal. calcd. for C$_{23}$H$_{23}$N$_3$·2.3CF$_3$CO$_2$H: C, 54.91; H, 4.22; N, 6.96. Found: C, 54.98; H, 4.17; N, 6.78.

EXAMPLE 47

6-(2-(2-acetyl-1,2,3,4-tetrahydro-6-isoquinolinyl) cyclopropyl)-N'-hydroxy-2-naphthalenecarboximidamide

EXAMPLE 47A 6-(2-(2-acetyl-1,2,3,4-tetrahydro-6-isoquinolinyl) cyclopropyl)-2-naphthonitrile The desired product was prepared by substituting Example 43A for Example 42I in Example 46A.

EXAMPLE 47B 6-(2-(2-acetyl-1,2,3,4-tetrahydro-6-isoquinolinyl)cyclopropyl)-N'-hydroxy-2-naphthalenecarboximidamide The desired product was prepared by substituting Example 47A for Example 42K in Example 42L.

MS (ESI(+)) m/e 400 (M+H)$^+$;

$^1$H NMR (300 MHz, DMSO-d$_6$) δ9.72 (s, 1H), 8.14 (s, 1H), 7.84–7.75 (m, 3H), 7.68 (s, 1H), 7.36–7.33 (m, 1H), 7.11–7.02 (m, 3H), 5.89 (s, 2H), 4.60–4.54 (m, 2H), 3.63 (t, 2H), 2.85–2.71 (m, 2H), 2.34–2.24 (m, 2H), 2.07 (s, 3H), 1.60–1.51 (m, 2H);

Anal. calcd. for C$_{25}$H$_{25}$N$_3$O$_2$.0.5H$_2$O: C, 73.51; H, 6.42; N, 10.29. Found: C, 73.68; H, 6.33; N, 10.12.

EXAMPLE 48

6-(2-(4-ethyl-1,2,3,4-tetrahydro-6-isoquinolinyl)cyclopropyl)-2-naphthalenecarboximidamide

EXAMPLE 48A 4-ethyl-6-methoxy-1,2,3,4-tetrahydroisoquinoline

A solution of 2-(3-methoxyphenyl)-1-butanamine (25 g, 131 mmol, prepared according to the procedure described in *J. Med. Chem.* 1990, 33, 153–160) in formic acid (120 mL) at room temperature was treated with paraformaldehyde (4.18 g, 131 mmol), stirred for 16 hours, treated with 25% KOH (30 mL) and ethanol (100 mL), and refluxed for 2.5 hours. The mixture was cooled to room temperature, extracted with dichloromethane, and the combined extracts were dried (MgSO$_4$), filtered, and concentrated. The concentrate was purified by flash column chromatography on silica gel with dichloromethane to provide the desired product.

MS (DCI/NH$_3$) m/e 192 (M+H)$^+$.

EXAMPLE 48B tert-butyl 6-(2-(6-cyano-2-naphthyl)ethenyl)-4-ethyl-3,4-dihydro-2(1H)-isoquinolinecarboxylate The desired product was prepared by substituting Example 48A for 6-methoxytetrahydroisoquinoline in Examples 42D–42I.

MS (DCI/NH$_3$) m/e 439 (M+H)$^+$.

EXAMPLE 48C tert-butyl 6-(2-(6-cyano-2-naphthyl)cyclopropyl)-4-ethyl-3,4-dihydro-2(1H)-isoquinolinecarboxylate The desired product was prepared by substituting Example 48B for Example 42I in Example 46A.

MS (DCI/NH$_3$) m/e 453 (M+H)$^+$.

EXAMPLE 48D 6-(2-(4-ethyl-1 2,3,4-tetrahydro-6-isoquinolinyl)cyclopropyl)-2-naphthalenecarboximidamide The desired product was prepared by substituting Example 48C for Example 1M in Example 1N.

MS (ESI(+)) m/e 370 (M+H)$^+$;

$^1$H NMR (300 MHz, DMSO-d$_6$) δ9.41 (s, 2H), 9.19 (s, 2H), 9.05 (s, 2H), 8.45 (s, 1H), 8.05–8.01 (m, 2H), 7.86 (s, 1H), 7.79 (d, 1H), 7.50 (d, 1H), 7.22 (s, 1H), 7.17–7.09 (m, 2H), 4.23 (s, 2H), 3.48–3.42 (m, 2H), 3.23–3.16 (m, 2H), 2.46–2.35 (m, 2H), 1.96–1.86 (m, 1H), 1.70–1.58 (m, 2H), 0.97–0.90 (m, 3H);

Anal. calcd. for C$_{29}$H$_{27}$N$_3$.2CF$_3$CO$_2$H.0.25H$_2$O: C, 57.85; H,4.94; N, 6.98. Found: C, 57.64; H, 4.68; N, 6.90.

EXAMPLE 49

6-(2-(2-benzyl-4-ethyl-1,2,3,4-tetrahydro-6-isoquinolinyl)cyclopropyl)-2-naphthalenecarboximidamide

EXAMPLE 49A 6-(2-(4-ethyl-1,2,3,4-tetrahydro-6-isoquinolinyl)ethenyl)-2-naphthonitrile The desired product was prepared by substituting Example 48B for Example 42I in Example 42J.

EXAMPLE 49B 6-(2-(2-benzyl-4-ethyl-1,2,3,4-tetrahydro-6-isoquinolinyl)ethenyl)-2-naphthonitrile A solution of Example 49A (600 mg) in dichloromethane (25 mL) was treated sequentially with benzaldehyde (0.7 mL), sodium triacetoxyborohydride (1.3 g), and acetic acid (319 mg), stirred for 24 hours, diluted with dichloromethane, washed with 1M NaOH and brine, dried (MgSO4), filtered, and concentrated. The concentrate was crystallized from diethyl ether/hexanes to provide the desired product.

MS (DCI/NH$_3$) m/e 429 (M+H)$^+$.

EXAMPLE 49C 6-(2-(2-benzyl-4-ethyl-1,2,3,4-tetrahydro-6-isoquinolinyl)cyclopropyl)-2-naphthonitrile The desired product was prepared by substituting Example 49B for Example 42I in Example 46A.

MS (DCI/NH$_3$) m/e 443 (M+H)$^+$.

EXAMPLE 49D 6-(2-(2-benzyl-4-ethyl-1,2,3,4-tetrahydro-6-isoquinolinyl)cyclopropyl)-2-naphthalenecarboximidamide The desired product was prepared by substituting Example 49C for Example 1M in Example 1N.

MS (ESI(+)) m/e 460 (M+H)$^+$;

$^1$H NMR (300 MHz, DMSO-d$_6$) δ9.40 (s, 2H), 9.17 (s, 2H), 8.45 (s, 1H), 8.04–8.00 (m, 2H), 7.85–7.77 (m, 2H), 7.56–7.49 (m, 6H), 7.28–7.10 (m, 3H), 4.50–4.22 (m, 4H), 3.58–3.42 (m, 2H), 3.20–3.10 (m, 2H), 2.45–2.39 (m, 2H), 2.01–1.94 (m, 1H), 1.67–1.64 (m, 2H), 0.89–0.83 (m, 3H);

Anal. calcd. for C$_{32}$H$_{33}$N$_3$.2.1TFA.H$_2$O: C, 60.63; H, 5.21; N, 5.86. Found: C, 60.37; H, 5.09; N, 5.88.

EXAMPLE 50

6-(2-(4-ethyl-1,2,3,4-tetrahydro-6-isoquinolinyl)ethenyl)-2-naphthalenecarboximidamide The desired product was prepared by substituting Example 49A for Example 1M in Example 1N.

MS (ESI(+)) m/e 356 (M+H)$^+$;
$^1$H NMR (300 MHz, DMSO-d$_6$) δ9.43 (s, 2H), 9.17 (m, 3H), 9.05 (m, 1H), 8.48–8.46(m, 2H), 8.16–8.02 (m, 4H), 7.87–7.81 (m, 1H), 7.68 (s, 1H), 7.60 (d, 1H), 7.53 (s, 1H), 7.29 (d, 1H), 4.30 (s, 2H), 3.27–3.04 (m, 3H), 2.00–1.75 (m, 2H), 0.98 (t, 3H);

Anal. calcd. for C$_{24}$H$_{25}$N$_3$.2TFA.H$_2$O: C, 55.91; H, 4.86; N, 6.99. Found: C, 55.90; H, 4.61; N, 6.89.

EXAMPLE 51

6-(2-(4-ethyl-2-methyl-1,2,3,4-tetrahydro-6-isoquinolinyl)cyclopropyl)-2-naphthalenecarboximidamide

EXAMPLE 51A 6-(2-(4-ethyl-2-methyl-1,2,3,4-tetrahydro-6-isoquinolinyl)cyclopropyl)-2-naphthonitrile A solution of Example 48C (284 mg) in 1:1 dichloromethane:TFA at room temperature was stirred for 1 hour, concentrated, and dissolved in methanol. The mixture was treated with 37% formaldehyde in water (1.1 mL) and sodium cyanoborohydride 70.0 mg), heated to 50° C., stirred for 16 hours, and extracted with dichloromethane. The combined extracts were washed with water and brine, dried (MgSO$_4$), filtered, and concentrated to provide the desired product.

MS (ESI(+)) m/e 367 (M+H)$^+$.

EXAMPLE 51B 6-(2-(4-ethyl-2-methyl-1,2,3,4-tetrahydro-6-isoquinolinyl)cyclopropyl)-2-naphthalenecarboximidamide The desired product was prepared by substituting Example 51A for Example 1M in Example 1N.

MS (ESI(+)) m/e 384 (M+H)$^+$;
$^1$H NMR (300 MHz, DMSO-d$_6$) δ10.00–9.80 (m, 1H), 9.41 (s, 2H), 9.18 (s, 2H), 8.45 (s, 1H), 8.04–8.01 (m, 2H), 7.86 (s, 1H), 7.80 (d, 1H), 7.51 (d, 1H), 7.29–7.22 (m, 1H), 7.12 (s, 2H), 4.50–4.20 (m, 2H), 3.73–3.60 (m, 2H), 3.28–3.06(m, 2H), 2.96 (s, 3H), 2.45–2.40 (m, 2H), 1.76–1.59 (m, 3H), 1.02–0.83 (m, 3H);

Anal. calcd. for C$_{26}$H29N$_3$.2.2CF$_3$CO$_2$H.H$_2$O: C, 55.97; H, 5.13; N, 6.44. Found C, 56.22; H, 4.95; N, 6.44.

EXAMPLE 52

6-(2-(2-acetyl-4-ethyl-1,2,3,4-tetrahydro-6-isoquinolinyl)cyclopropyl)-2-naphthalenecarboximidamide

EXAMPLE 52A 6-(2-(2-acetyl-4-ethyl-1,2,3,4-tetrahydro-6-isoquinolinyl)cyclopropyl)-2-naphthonitrile A solution of Example 48C in 1:1 methylene chloride-:TFA at room temperature was stirred for 1 hour and concentrated. The resulting product and acetyl chloride were substituted for Example 42J and methyl chloroformate, respectively, in Example 42K to provide the desired product.

MS (DCI/NH$_3$) m/e 395 (M+H)$^+$.

EXAMPLE 52B 6-(2-(2-acetyl-4-ethyl-1,2,3,4-tetrahydro-6-isoquinolinyl)cyclopropyl)-2-naphthalenecarboximidamide The desired product was prepared by substituting Example 52A for Example 1M in Example 1N.

MS(ESI(+)) m/e 412 (M+H)$^+$;
$^1$H NMR (300 MHz, DMSO-d$_6$) δ9.39 (s, 2H), 9.04 (s, 2H), 8.44 (s, 1H), 8.05–8.00 (m, 2H), 7.85 (s, 1H), 7.80–7.76 (m, 1H), 7.52–7.50 (m, 1H), 7.13–6.98 (m, 3H), 4.81–4.25 (m, 3H), 3.05–3.01 (m, 1H), 2.74–2.65 (m, 1H), 2.44–2.35 (m, 2H), 2.10–2.08 (m, 3H), 1.65–1.51 (m, 4H), 1.01–0.91 (m, 3H);

Anal. calcd. for C$_{27}$H$_{29}$N$_3$O.1.5CF$_3$CO$_2$H.0.25H$_2$O: C, 61.38; H, 5.32; N, 7.16. Found C, 61.29; H, 5.21; N, 7.07.

EXAMPLE 53

6-(2-(1-isopropyl-3,4-dihydro-6-isoquinolinyl)cyclopropyl)-2-naphthalenecarboximidamide

EXAMPLE 53A

N-(2-(3-bromophenyl)ethyl)-2-methylpropanamide

A solution of 2-(3-bromophenyl)ethylamine (3.0 g) in dichloromethane (180 mL) at room temperature was treated sequentially with triethylamine (7.0 mL), DMAP (10 mg), and a solution of 2-methylpropanoyl chloride(1.52 mL) in dichloromethane (30 mL). The mixture was stirred for 3 hours, quenched with N$^1$,N$^2$-dimethyl-1,2-ethanediamine, washed sequentially with 0.5M HCl, water, and brine, dried (MgSO$_4$), filtered, and concentrated to provide the desired product.

MS (DCI/NH$_3$) m/e 270 (M+H)$^+$.

EXAMPLE 53B 6-bromo-1-isopropyl-3,4-dihydroisoquinoline

A solution of Example 53A in dichloromethane (80 mL) at 0° C. was treated with oxalyl chloride (1.62 g), stirred for 15 minutes, warmed to room temperature, stirred for 2.5 hours, cooled to −78° C., treated with ferrous(III)chloride (2.34 g), warmed to room temperature, and stirred for 16 hours. The mixture was cooled to 0° C., treated dropwise with 2M HCl (55 mL), warmed to room temperature, stirred for 5 hours, and extracted with dichloromethane. The combined extracts were washed with water and brine, dried (MgSO$_4$), filtered, and concentrated. The concentrate was suspended in methanol (50 mL), slowly treated with concentrated H$_2$SO$_4$(6.0 mL), heated to reflux, stirred for 16 hours, cooled to room temperature, and concentrated. The concentrate was diluted with water and washed with ethyl acetate. The aqueous layer was cooled to 0° C., slowly adjusted to pH>7 with 50% NaOH, and extracted with dichloromethane. The combined extracts were washed with water and brine, dried (MgSO$_4$), filtered, and concentrated to provide the desired product.

MS (DCI/NH$_3$) m/e 252 (M+H)$^+$.

EXAMPLE 53C 1-isopropyl-3,4-dihydro-6-isoquinolinecarbaldehyde

A solution of Example 53B (1.4 g) in THF (30 mL) at −78° C. was treated with 1M butyllithium in hexanes (4.16 mL), stirred for 10 minutes, treated with N-formylmorpholine (250 mg), warmed to room temperature, and stirred for 15 minutes. The mixture was quenched with water and concentrated. The concentrate was purified by flash column chromatography on silica gel with 15% ethyl acetate/hexanes to provide the desired product.

MS (DCI/NH$_3$) m/e 202 (M+H)$^+$.

EXAMPLE 53D 6-(2-(1-isopropyl-3,4-dihydro-6-isoquinolinyl)
ethenyl)-2-naphthonitrile The desired product was prepared by substituting
Example 53C for Example 42H in Example 42I.

EXAMPLE 53E 6-(2-(1-isopropyl-3,4-dihydro-6-isoquinolinyl)
cyclopropyl)-2-naphthonitrile The desired product was prepared by substituting
Example 53D for Example 1L in Example 1M.

MS (DCI/NH$_3$) m/e 365 (M+H)$^+$.

EXAMPLE 53F 6-(2-(1-isopropyl-3,4-dihydro-6-isoquinolinyl)
cyclopropyl)-2-naphthalenecarboximidamide The desired product was prepared by substituting
Example 53E for Example 1M in Example 1N.

MS (ESI(+)) m/e 382 (M+H)$^+$;
$^1$H NMR (300 MHz, DMSO-d$_6$) δ12.22 (br s, 1H), 9.41
(s, 2H), 9.21 (s, 2H), 8.46 (s, 1H), 8.05 (m, 3H) 7.89 (s, 1H),
7.80 (d, 1H), 7.53 (d, 1H), 7.42 (d, 1H), 7.39 (s, 1H),
3.84–3.79 (m, 2H), 3.09–3.04 (m, 2H), 2.66–2.50 (m, 3H),
1.89–1.80 (m, 2H), 1.31 (d, 6H);

Anal. calcd. for C$_{26}$H$_{27}$N$_3$.2.3CF$_3$CO$_2$H.0.5H$_2$O: C,
56.30; H, 4.68; N, 6.44. Found C, 5 56.05; H, 4.66; N, 6.13.

EXAMPLE 54

6-(2-(4-ethyl-1-isopropyl-3,4-dihydro-6-
isoquinolinyl)cyclopropyl)-2-
naphthalenecarboximidamide The desired product was prepared by substituting
Example 55B for 2-(3-bromophenyl)ethylamine in Example
53.

MS (ESI(+)) m/e 410 (M+H)$^+$;
$^1$NMR (300 MHz, DMSO-d$_6$) δ12.22 (br s, 1H), 9.43 (s,
2H), 9.26 (s, 2H), 8.47 (s, 1H), 8.11–8.03 (m, 3H), 7.90 (s,
1H), 7.81 (d, 1H), 7.55–7.41(m, 2H), 7.54 (d, 1H),
3.91–3.81 (m, 3H), 3.03–3.01 (m, 1H), 2.70–2.57 (m, 2H),
1.91–1.79 (m, 2H), 1.54–1.47 (m, 2H), 1.38 (d, 3H), 1.26 (d,
3H), 0.94–0.86 (m, 3H);

Anal. calcd. for C$_{28}$H$_{31}$N$_3$.2.4CF$_3$CO$_2$H.0.5H$_2$O: C,
56.91; H, 5.01; N, 5.86. Found: C, 56.97; H, 4.93; N, 5.93.

EXAMPLE 55

6-(2-(4-ethyl-1-isopropyl-3,4-dihydro-6-
isoquinolinyl)ethenyl)-2-
naphthalenecarboximidamide

EXAMPLE 55A 2-(3-bromophenyl)butanenitrile

A solution of 3-bromophenylacetonitrile (8.12 g) in
dichloromethane (150 mL) at room temperature was treated
sequentially with tetrabutylammonuim hydrogen sulfate
(14.1 g), iodoethane (10 mL), and 15% NaOH (35 mL),
stirred for 4 hours, and separated. The aqueous phase was
extracted with dichloromethane, and the combined extracts
were washed with water and brine, dried (MgSO$_4$), filtered,
and concentrated. The concentrate was purified by flash
column chromatography on silica gel with 50%
dichloromethane/hexanes to provide the desired product.

MS (DCI/NH$_3$) m/e 224 (M+H)$^+$.

EXAMPLE 55B 2-(3-bromophenyl)-1-butanamine

A solution of Example 55A (8 g) in THF (250 mL) at
room temperature was treated with1M BH$_3$ in THF (100
mL) stirred for 16 hours, treated with ethanol (20 mL) and
4M HCl in dioxane (80 mL), and concentrated. The con-
centrate was suspended in methanol (150 mL), treated with
HCl gas, boiled for 3 hours, cooled to room temperature, and
treated with diethyl ether. The resulting precipitate was
collected by filtration, washed with diethyl ether and hexane,
and dried to provide the desired product.

MS (DCI/NH$_3$) m/e 228 (M+H)$^+$.

EXAMPLE 55C 6-(2-(4-ethyl-1-isopropyl-3,4-dihydro-6-
isoquinolinyl ethenyl)-2-naphthonitrile The desired product was prepared by substituting
Example 55B for 2-(3-bromophenyl)ethylamine in
Examples 53A–53D.

MS (DCI/NH$_3$) m/e 379 (M+H)$^+$.

EXAMPLE 55D 6-(2-(4-ethyl-1-isopropyl-3,4-dihydro-6-
isoquinolinyl)ethenyl)-2-napthenecarboximidamide The desired product was prepared by substituting
Example 55C for Example 1M in Example 1N.

MS (ESI(+)) m/e 396 (M+H)$^+$;
$^1$H NMR (300 MHz, DMSO-d$_6$) δ9.45 (s, 2H), 9.15 (s,
2H), 8.48 (s, 1 H), 8.26–8.08 (m, 5H), 7.88–7.82 (m, 4H),
7.80–7.65 (m, 1H), 3.90–3.85 (m, 3H), 3.03–3.01 (m, 1H),
1.62–1.52 (m, 2H), 1.39 (d, 3H), 1.29 (d, 3H), 0.94 (d, 3H);

Anal. calcd. for C$_{27}$H$_{29}$N$_3$.2.5CF$_3$CO$_2$H.H$_2$O: C, 55.02;
H, 4.83; N, 6.01. Found: C, 55.23; H, 4.75; N, 6.00.

EXAMPLE 56

8-bromo-6-(2-(1-cyclohexyl-3,4-dihydro-7-
isoquinolinyl)cyclopropyl)-2-
naphthalenecarboximidamide

EXAMPLE 56A 8-bromo-6-(2-(1-cyclohexyl-3,4-dihydro-7-
isoquinolinyl)ethenyl)-2-naphthonitrile The desired product was prepared by substituting cyclo-
hexanecarbonyl chloride for 2-methylpropanyl chloride in
Examples 1I–1K.

EXAMPLE 56B 8-bromo-6-(2-(1-cyclohexyl-3,4-dihydro-7-
isoquinolinyl)cyclopropyl)-2-
naphthalenecarboximidamide The desired product was prepared by substituting
Example 56A for Example 1L in Examples 1M–1N.

MS (APCI(+)) m/e 500 (M+H)$^+$;

¹H NMR (300 MHz, DMSO-d₆) δ9.55 (s, 2H), 9.21 (s, 2H), 8.53 (s, 1H), 8.13 (d, 1H), 8.05 (s, 1H), 7.95 (s, 1H), 7.91 (s, 1H), 7.86 (dd, 1H), 7.59 (d, 1H), 7.49 (d, 1H), 3.80 (t, 2H), 3.05 (t, 2H), 2.64–2.55 (m, 3H), 1.90–1.73 (m, 7H), 1.55–1.45 (m, 4H), 1.30–1.18 (m, 1H);

Anal. calcd. for $C_{29}H_{30}BrN_3.2.5CF_3CO_2H$: C, 50.08; H, 4.34; N, 5.56. Found: C, 50.26; H, 3.92; N, 5.26.

EXAMPLE 57

8-bromo-6-(2-(1-cyclohexyl-2-methyl-1,2,3,4-tetrahydro-7-isoquinolinyl)cyclopropyl)-2-naphthalenecarboximidamide The desired product was prepared by substituting Example 56A for Example 11C in Examples 11D–11F.

MS (APCI(+)) m/e 516 (M+H)⁺;

¹H NMR (300 MHz, DMSO-d₆) δ9.54 (br s, 2H), 9.43 (br s, 1H), 9.20 (br s, 2H), 8.52 (s, 1H), 8.11 (dd, 1H), 7.92 (s, 1H), 7.91 (s, 1H), 7.86 (dd, 1H), 7.23 (d, 1H), 7.13 (dd, 1H), 7.05 (s, 1H), 4.17–4.15 (m, 2H), 3.30–3.15 (m, 2H), 3.02–2.98 (m, 1H), 2.80 (d, 3H), 2.39–2.36 (m, 1H), 1.95–1.85 (m, 1H), 1.80–1.55 (m, 7H), 1.44–1.43 (m, 1H), 1.28–1.11 (m, 4H), 0.95–0.80 (m, 1H);

Anal. calcd. for $C_{30}H_{34}BrN_3.2.6CF_3CO_2H$: C, 50.09; H, 4.72; N, 5.38. Found: C, 50.46; H, 4.55; N, 5.04.

EXAMPLE 58

6-(2-(1-cyclohexyl-3,4-dihydro-7-isoquinolinyl)cyclopropyl)-8-((1E)-3-methyl-1-butenyl)-2-naphthalenecarboximidamide

EXAMPLE 58A 8-bromo-6-(2-(1-cyclohexyl-3,4-dihydro-7-isoquinolinyl)cyclopropyl)-2-naphthonitrile The desired product was prepared by substituting Example 56A for Example 1L in Example 1M.

EXAMPLE 58B 6-(2-(1-cyclohexyl-3,4-dihydro-7-isoquinolinyl)cyclopropyl)-8-((1E)-3-methyl-1-butenyl)-2-naphthonitrile The desired product was prepared by substituting Example 37A and Example 58A for Example 4B and Example 4A, respectively, in Example 4C.

EXAMPLE 58C 6-(2-(1-cyclohexyl-3,4-dihydro-7-isoquinolinyl)cyclopropyl)-8-((1E)-3-methyl-1-butenyl)-2-naphthalenecarboximidamide The desired product was prepared by substituting Example 58B for Example 1M in Example 1N.

MS (APCI(+)) m/e 490 (M+H)⁺;

1H NMR (300 MHz, DMSO-d₆) δ12.35 (br s, 1H), 9.45 (s, 2H), 9.18 (s, 2H), 8.65 (s, 1H), 8.05 (s, 1H), 8.04 (d, 1H), 7.81 (dd, 1H), 7.75 (s, 1H), 7.61 (s, 1H), 7.60 (dd, 1H), 7.49 (d, 1H), 7.26 (d, 1H), 6.49 (dd, 1H), 3.83–3.73 (m, 2H), 3.05 (t, 2H), 2.67–2.49 (m, 6H), 1.91–1.71 (m, 6H), 1.55–1.49 (m, 3H), 1.23–1.19 (m, 1H), 1.17 (dd, 6H);

Anal. calcd. for $C_{34}H_{39}BrN_3 2.6CF_3CO_2H$: C, 58.23; H, 5.55; N, 5.57. Found: C, 58.37; H, 5.20; N, 5.17.

EXAMPLE 59

6-(2-(1-cyclohexyl-2-methyl-1,2,3,4-tetrahydro-7-isoquinolinyl)cyclopropyl)-8-((1E)-3-methyl-1-butenyl)-2-naphthalenecarboximidamide

EXAMPLE 59A 8-bromo-6-(2-(1-cyclohexyl-2-methyl-1,2,3,4-tetrahydro-7-isoquinolinyl)cyclopropyl)-2-naphthonitrile The desired product was prepared by substituting Example 58A for Example 31F in Example 32A.

EXAMPLE 59B 6-(2-(1-cyclohexyl-2-methyl-1,2,3,4-tetrahydro-7-isoquinolinyl)cyclopropyl)-8-((1E)-3-methyl-1-butenyl)-2-naphthalenecarboximidamide The desired product was prepared by substituting Example 59A for Example 58A in Examples 58B and 58C.

MS (APCI(+)) m/e 506 (M+H)⁺;

¹H NMR (300 MHz, DMSO-d₆) δ9.43 (br s, 3H), 9.16 (s, 2H), 8.63 (s, 1H), 8.02 (d, 1H), 7.82 (s, 1H), 7.74 (s, 1H), 7.58 (s, 1H), 7.27–7.13 (m, 3H), 7.02 (s, 1H), 6.52–6.45 (m, 1H), 4.19–4.10 (m, 1H), 3.32–3.18 (m, 1H), 3.05–3.00 (m, 2H), 2.81–2.79 (m, 2H), 2.66–2.49 (m, 6H), 2.38–2.36 (m, 1H), 1.90–1.44 (m, 8H), 1.25–1.11 (m, 2H), 1.17 (d, 6H), 0.95–0.80 (m, 1H);

Anal. calcd. for $C_{35}H_{43}N_3.2.5CF_3CO_2H$: C, 59.20; H, 6.03; N, 5.52. Found: C, 59.23; H, 5.88; N, 5.35.

EXAMPLE 60

8-allyl-6-(2-(1-isopropyl-2-methyl-1,2,3,4-tetrahydro-7-isoquinolinyl)cyclopropyl)-2-naphthalenecarboximidamide The desired product was prepared by substituting1-propyne for 3-methyl 1-butyne in Example 37.

MS (APCI(+)) m/e 438 (M+H)⁺;

¹H NMR (300 MHz, DMSO-d₆) δ9.42 (s, 3H), 9.13 (s, 2H), 8.55 (s, 1H), 8.04 (dd, 1H), 7.81 (d, 1H), 7.71 (s, 1H), 7.36 (s, 1H), 7.25–7.17 (m, 1H), 7.03 (d, 1H), 6.20–6.11 (m, 1H), 5.18–5.10 (m, 2H), 3.92 (d, 1H), 3.70–3.20 (m, 4H), 3.10–3.00 (m, 2H), 2.85–2.81 (m, 2H), 2.51–2.10 (m, 2H), 1.68–1.65 (m, 1H), 1.12–1.08 (m, 4H), 0.86–0.81 (m, 4H);

Anal. calcd. for $C_{30}H_{35}N_3.2.5CF_3CO_2H$: C, 56.36; H, 5.46; N, 6.07. Found: C, 56.52; H, 5.01; N, 5.90.

It will be evident to one skilled in the art that the instant invention is not limited to the forgoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims and therefore intended to be embraced therein.

What is claimed is:

1. A compound of formula (I)

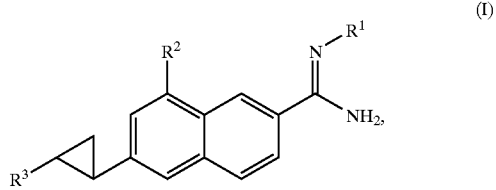

or a pharmaceutically acceptable salt thereof, wherein

R¹ is hydrogen or hydroxy;

R² is selected from the group consisting of hydrogen, halo, alkyl, alkenyl, alkynyl, alkoxyalkyl, heterocycloalkyl, aryl, heteroaryl, cycloalkyl, and —NRᵃRᵇ, wherein Rᵃ and Rᵇ are independently selected from the group consisting of hydrogen, aryl, and heteroaryl; and R³ is

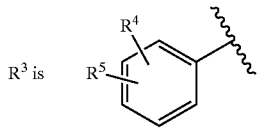

wherein R⁴ and R⁵ are on adjacent carbon atoms and, taken together with the carbon atoms to which they are attached, are pyridine or a nitrogen-containing heterocycloalkyl, wherein the groups defining R³ can be optionally substituted with one. two, three, four, or five substituents independently selected from the group consisting of alkyl, cycloalkyl, (cycloalkyl)alkyl, hydroxy, hydroxyalkyl, aryl, arylalkyl, alkanoyl, alkoxycarbonyl, alkenyl, alkynyl, halo, haloalkyl, heteroaryl, heteroarylalkyl, and a nitrogen protecting group.

2. A compound according to claim 1, wherein R³ is optionally substituted isoquinolinyl.

3. A compound according to claim 2 which is 6-(2-(-isopropyl-7-isoquinolinyl)cyclopropyl)-2-naphthalenecarbonximidamide.

4. A compound according to claim 1, wherein R³ is optionally substituted 3,4-dihydro-6-isoquinolinyl.

5. A compound according to claim 4 selected from the group consisting of 6-(2-(4,4-diethyl-1-isopropyl-3,4-dihydro-6-isoquinolinyl)cyclopropyl)-2-naphthalenecarboximidamide,
6-(2-(1-isopropyl-3,4-dihydro-6-isoquinolinyl)cyclopropyl)-2-naphthalenecarboximidamide, and
6-(2-(4-ethyl-1-isopropyl-3,4-dihydro-6-isoquinolinyl)cyclopropyl)-2-naphthalenecarboximidamide.

6. A compound according to claim 1, wherein R³ is optionally substituted 3,4-dihydro-7-isoquinolinyl.

7. A compound according to claim 6 selected from the group consisting of 8-(3-furyl)-6-(2-(1-isopropyl-3,4-dihydro-7-isoquinolinyl)cyclopropyl)-2-naphthalenecarboximidamide,
6-(2-(-isopropyl-3,4-dihydro-7-isoquinolinyl)cyclopropyl)-8-((1E)-3-methoxy-1-propenyl)-2-naphthalenecarboximidamide,
6-(2-(1-isopropyl-3,4-dihydro-7-isoquinolinyl)cyclopropyl)-8-tetrahydro-3-furanyl-2-naphthalenecarboximidamide,
6-(2-(1-isopropyl-3,4-dihydro-7-isoquinolinyl)cyclopropyl)-8-((1E)-3-methyl-1-butenyl)-2-naphthalenecarboximidamide,
6-(2-(1-cyclohexyl-3,4-dihydro-7-isoquinolinyl)cyclopropyl)-2-naphthalenecarboximidamide,
6-(2-(1-phenyl-3,4-dihydro-7-isoquinolinyl)cyclopropyl)-2-naphthalenecarboximidamide,
6-(2-(1-isopropyl-3,4-dihydro-7-isoquinolinyl)cyclopropyl)-2-naphthalenecarboximidamide,
6-((1S,2S)-2-(1-isopropyl-3,4-dihydro-7-isoquinolinyl)cyclopropyl)-2-naphthalenecarboximidamide,
6-((1R,2R)-2-(1-isopropyl-3,4-dihydro-7-isoquinolinyl)cyclopropyl)-2-naphthalenecarboximidamide,
8-((1E)-3,3-dimethyl-1-butenyl)-6-(2-(1-isopropyl-3,4-dihydro-7-isoquinolinyl)cyclopropyl)-2-naphthalenecarboximidamide,
8-bromo-6-(2-(1-isopropyl-3,4-dihydro-7-isoquinolinyl)cyclopropyl)-2-naphthalenecarboximidamide,
8-bromo-6-(2-(1-cyclohexyl-3,4-dihydro-7-isoquinolinyl)cyclopropyl)-2-naphthalenecarboximidamide, and
6-(2-(1-cyclohexyl-3,4-dihydro-7-isoquinolinyl)cyclopropyl)-8-((1E)-3-methyl-1-butenyl)-2-naphthalenecarboximidamide.

8. A compound according to claim 1, wherein R³ is optionally substituted 1,2,3,4-tetrahydro-6-isoquinolinyl.

9. A compound according to claim 8 selected from the group consisting of 6-(2-(4,4-diethyl-1-isopropyl-2-methyl-1,2,3,4-tetrahydro-6-isoquinolinyl)cyclopropyl)-2-naphthalenecarboximidamide,
6-(2-(1,2,3,4-tetrahydro-6-isoquinolinyl)cyclopropyl)-2-naphthalenecarboximidamide,
6-(2-(2-acetyl-1,2,3,4-tetrahydro-6-isoquinolinyl)cyclopropyl)-N'-hydroxy-2-naphthalenecarboximidamide,
6-(2-(4-ethyl-1,2,3,4-tetrahydro-6-isoquinolinyl)cyclopropyl)-2-naphthalenecarboximidamide,
6-((2-(2-benzyl-4-ethyl-1,2,3,4-tetrahydro-6-isoquinolinyl)cyclopropyl)-2-naphthalenecarboximidamide,
6-(2-(4-ethyl-2-methyl-1,2,3,4-tetrahydro-6-isoquinolinyl)cyclopropyl)-2-naphthalenecarboximidamide, and
6-(2-(1-isopropyl-3,4-dihydro-6-isoquinolinyl)cyclopropyl)-2-naphthalenecarboximidamide.

10. A compound according to claim 1, wherein R³ is optionally substituted 1,2,3,4-tetrahydro-7-isoquinolinyl.

11. A compound according to claim 10 selected from the group consisting of 8-(3-furyl)-6-(2-(1-isopropyl-2-methyl-1,2,3,4-tetrahydro-7-isoquinolinyl)cyclopropyl)-2-naphthalenecarboximidamide,
6-(2-(1-isopropyl-2-methyl-1,2,3,4-tetrahydro-7-isoquinolinyl)cyclopropyl-8-((1E)-3-methoxy-1-propenyl)-2-naphthalenecarboximidamide,
N'-hydroxy-6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide,
6-(2-(2-methyl-1-propyl-1,2,3,4-tetrahydro-7-isoquinolinyl)cyclopropyl)-2-naphthalenecarboximidamide,
6-(2-(1-cyclohexyl-2-methyl-1,2,3,4-tetrahydro-7-isoquinolinyl)cyclopropyl)-2-naphthalenecarboximidamide,
6-(2-(2-acetyl-1-isopropyl-1,2,3,4-tetrahydro-7-isoquinolinyl)cyclopropyl)-2-naphthalenecarboximidamide,
6-(2-(1-isopropyl-2-methyl-1,2,3,4-tetrahydro-7-isoquinolinyl)cyclopropyl)-2-naphthalenecarboximidamide,
6-(2-(2-benzyl-1-isopropyl-1,2,3,4-tetrahydro-7-isoquinolinyl)cyclopropyl)-2-naphthalenecarboximidamide,
6-(2-(1-isopropyl-1,2,3,4-tetrahydro-7-isoquinolinyl)cyclopropyl)-2-naphthalenecarboximidamide,
6-(2-(1-isopropyl-2-(3-pyridinylmethyl)-1,2,3,4-tetrahydro-7-isoquinolinyl)cyclopropyl-2-naphthalenecarboximidamide,
6-(2-(2-cyclopropylmethyl)-1-isopropyl-1,2,3,4-tetrahydro-7-isoquinolinyl)cyclopropyl)-2-naphthalenecarboximidamide,
6-(2-(2-ethyl-1-isopropyl-1,2,3,4-tetrahydro-7-isoquinolinyl)cyclopropyl)-2-naphthalenecarboximidamide,
6-(2-(2-allyl-1-isopropyl-1,2,3,4-tetrahydro-7-isoquinolinyl)cyclopropyl)-2-naphthalenecarboximidamide, 6-(2-(2-(2-hydroxyethyl)-1-isopropyl-1,2,3,4-tetrahydro-7-isoquinolinyl)cyclopropyl)-2-naphthalenecarboximidamide, 6-(2-(1,2-diisopropyl-1,2,3,4-tetrahydro-7-isoquinolinyl)cyclopropyl)-2-naphthalenecarboximidamide, 6-(2-(4,4-diethyl-1-isopropyl-3,4-dihydro-6-isoquinolinyl)cyclopropyl)-2-naphthalenecarboximidamide, 6-(2-(1-isopropyl-2-(2,2,2-trifluoroethyl)-1,2,3,4-tetrahydro-7-isoquinolinyl)cyclopropyl)-2-naphthalenecarboximidamide, 8-bromo-6-(2-(1-isopropyl-2-methyl-1,2,3,4-tetrahydro-7-isoquinolinyl)cyclopropyl)-2-naphthalenecarboximidamide, 6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide, 6-(2-(1-isopropyl-2-methyl-1,2,3,4-tetrahydro-7-isoquinolinyl)cyclopropyl)-8-((1E)-3-methyl-1,3-butanienyl)-2-naphthalenecarboximidamide, 8-cyclopropyl-6-(2-(1-isopropyl-2-methyl-1,2,3,4-tetrahydro-7-isoquinolinyl)cyclopropyl)-2-naphthalenecarboximidamide, 6-(2-(1-isopropyl-2-methyl-1,2,3,4-tetrahydro-7-isoquinolinyl)cyclopropyl)-8-(2-methoxyphenyl)-2-naphthalenecarboximidamide, 6-(2-(1-isopropyl-2-methyl-1,2,3,4-tetrahydro-7-isoqunolinyl)cyclopropyl)-8-vinyl-2-naphthalenecarboximidamide, 8-bromo-6-(2-(1-cyclohexyl-2-methyl-1,2,3,4-tetrahydro-7-isoquinolinyl)cyclopropyl)-2-naphthalenecarboximidamide, 6-(2-(1-cyclohexyl-2-methyl-1,2,3,4-tetrahydro-7-isoquinolinyl)cyclopropyl)-8-((1E)-3-methyl-1-butenyl)-2-naphthalenecarboximidamide, and 8-allyl-6-(2-(1-isopropyl-2-methyl-1,2,3,4-tetrahydro-7-isoquinolinyl)cyclopropyl)-2-naphthalenecarboximidamide.

12. A method for the preparation of a compound of formula (I),

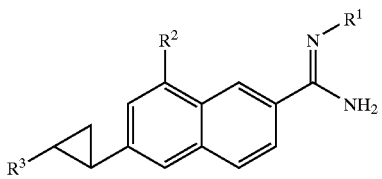

or a pharmaceutically acceptable salt thereof, wherein
$R^1$ is hydrogen or hydroxy;
$R^2$ is selected from the group consisting of hydrogen, halo, alkyl, alkenyl, alkynyl, alkoxyalkyl, heterocycloalkyl, aryl, heteroaryl, cycloalkyl, and —$NR^aR^b$, wherein $R^a$ and $R^b$ are independently selected from the group consisting of hydrogen, aryl, and heteroaryl; and $R^3$ is 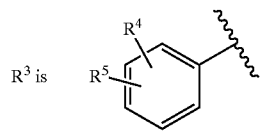

wherein $R^4$ and $R^5$ are on adjacent carbon atoms and, taken together with the carbon atoms to which they are attached, are pyridine or a nitrogen-containing heterocycloalkyl, wherein the groups defining $R^3$ can be optionally substituted with one, two, three, four, or five substituents independently selected from the group consisting of alkyl, cycloalkyl, (cycloalkyl)alkyl, hydroxy, hydroxyalkyl, aryl, arylalkyl, alkanoyl, alkoxycarbonyl, alkenyl, alkynyl, halo, haloalkyl, heteroaryl, heteroarylalkyl, and a nitrogen protecting group, the method comprising (a) reacting a compound of formula (Ia)

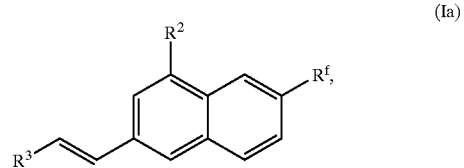

wherein $R^f$ is cyano or —$C(=NR^1)NH_2$, with diazomethane or trimethylsilyldiazomethane in the presence of a palladium catalyst;

(b) optionally reacting the product from step (a) with an anionic nitrogen source.

13. A method according to claim 12, wherein the palladium catalyst is selected from the group consisting of palladium (II) acetate, palladium (II) chloride, and palladium (II) dibenzylideneacetone.

14. A method according to claim 12, wherein the anionic nitrogen source is selected from the group consisting of lithium hexamethyldisilazide, potassium hexamethyldisilazide, and sodium hexamethyldisilazide.

15. A compound selected from the group consisting of 6-(2-(1-isopropyl-1,2,3,4-tetrahydro-7-isoquinolinyl)ethenyl)-2-naphthalenecarboximidamide, 6-(2-(1-isopropyl-2-methyl-1,2,3,4-tetrahydro-7-isoquinolinyl)ethenyl)-2-naphthalenecarboximidamide, methyl 7-(2-(6-(amino(imino)methyl)-2-naphthyl)ethenyl)-1-isopropyl-3,4-dihydro-2(1H)-isoquinolinecarboxylate, 8-bromo-6-(2-(1-isopropyl-3,4-dihydro-7-isoquinolinyl)ethenyl)-2-naphthalenecarboximidamide, methyl 6-(2-(6-(amino(hydroxyimino)methyl)-2-naphthyl)ethenyl)-3,4-dihydro-2(1H)-isoquinolinecarboxylate, 6-(2-(2-acetyl-1,2,3,4-tetrahydro-6-isoquinolinyl)ethenyl-N'-hydroxy-2-naphthalenecarboximidamide, 6-(2-(2-acetyl-1,2,3,4-tetrahydro-6-isoquinolinyl)ethenyl)-2-naphthalenecarboximidamide, N'-hydroxy-6-(2-(1,2,3,4-tetrahydro-6-isoquinolinyl)ethenyl)-2-naphthalenecarboximidamide, 6-(2-(4-ethyl-1,2,3,4-tetrahydro-6-isoquinolinyl)ethenyl)-2-naphthalenecarboximidamide, and 6-(2-(4-ethyl-1-isopropyl-3,4-dihydro-6-isoquinolinyl)ethenyl)-2-naphthalenecarboximidamide.

16. A pharmaceutical composition comprising a compound of claim 1, or a pharmaceutically acceptable salt thereof, in combination with a pharmaceutically acceptable carrier.

17. A method of inhibiting urokinase in a mammal in recognized need of such treatment comprising administering to the mammal a pharmaceutically acceptable amount of a compound of claim 1, or a pharmaceutically acceptable salt thereof.

18. A compound selected from the group consisting of 8-(3-furyl)-6-(2-(1-isopropyl-3,4-dihydro-7-isoquinolinyl)cyclopropyl)-2-naphthalenecarboximidamide, 6-(2-(1-isopropyl-7-isoquinolinyl)cyclopropyl)-2-naphthalenecarbonximidamide, 8-(3-furyl)-6-(2-(1-isopropyl-2-methyl-1,2,3,4-tetrahydro-7-isoquinolinyl)cyclopropyl)-2-naphthalenecarboximidamide, 6-(2-(1-isopropyl-3,4-dihydro-7-isoquinolinyl)cyclopropyl)-8-((1E)-3-methoxy-1-propenyl)-2-naphthalenecarboximidamide, 6-(2-(1-isopropyl-2-methyl-1,2,3,4-tetrahydro-7-isoquinolinyl)cyclopropyl-8-((1E)-3-methoxy-1-propenyl)-2-naphthalenecarboximidamide, N'-hydroxy-6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide, 6-(2-(1-isopropyl-3,4-dihydro-7-isoquinolinyl)cyclopropyl)-8-tetrahydro-3-furanyl-2-naphthalenecarboximidamide, 6-(2-(1-isopropyl-3,4-dihydro-7-isoquinolinyl)cyclopropyl)-8-((1E)-3-methyl-1-butenyl)-2-naphthalenecarboximidamide, 6-(2-(1-cyclohexyl-3,4-dihydro-7-isoquinolinyl)cyclopropyl)-2-naphthalenecarboximidamide, 6-(2-(1-phenyl-3,4-dihydro-7-isoquinolinyl)cyclopropyl)-2-naphthalenecarboximidamide, 6-(2-(2-methyl-1-propyl-1,2,3,4-tetrahydro-7-isoquinolinyl)cyclopropyl)-2-naphthalenecarboximidamide, 6-(2-(1-cyclohexyl-2-methyl-1,2,3,4-tetrahydro-7-isoquinolinyl)cyclopropyl)-2-naphthalenecarboximidamide, 6-(2-(1-isopropyl-1,2,3,4-tetrahydro-7-isoquinolinyl)ethenyl)-2-naphthalenecarboximidamide, 6-(2-(1-isopropyl-3,4-dihydro-7-isoquinolinyl)cyclopropyl)-2-naphthalenecarboximidamide, 6-(2-(2-acetyl-1-isopropyl-1,2,3,4-tetrahydro-7-isoquinolinyl)cyclopropyl)-2-naphthalenecarboximidamide, 6-(2-(1-isopropyl-2-methyl-1,2,3,4-tetrahydro-7-isoquinolinyl)ethenyl)-2-naphthalenecarboximidamide, methyl 7-(2-(6-(amino(imino)methyl)-2-naphthyl)ethenyl)-1-isopropyl-3,4-dihydro-2(1H)-isoquinolinecarboxylate, 6-(2-(1-isopropyl-2-methyl-1,2,3,4-tetrahydro-7-isoquinolinyl)cyclopropyl)-2-naphthalenecarboximidamide, 6-(2-(2-benzyl-1-isopropyl-1,2,3,4-tetrahydro-7-isoquinolinyl)cyclopropyl)-2-naphthalenecarboximidamide, 6-(2-(1-isopropyl-1,2,3,4-tetrahydro-7-isoquinolinyl)cyclopropyl)-2-naphthalenecarboximidamide, 6-(2-(1-isopropyl-2-(3-pyridinylmethyl)-1,2,3,4-tetrahydro-7-isoquinolinyl)cyclopropyl-2-naphthalenecarboximidamide, 8-bromo-6-(2-(1-isopropyl-3,4-dihydro-7-isoquinolinyl)ethenyl)-2-naphthalenecarboximidamide, 6-(2-(2-cyclopropylmethyl)-1-isopropyl-1,2,3,4-tetrahydro-7-isoquinolinyl)cyclopropyl)-2-naphthalenecarboximidamide, 6-(2-(2-ethyl-1-isopropyl-1,2,3,4-tetrahydro-7-isoquinolinyl)cyclopropyl)-2-naphthalenecarboximidamide, 6-(2-(2-allyl-1-isopropyl-1,2,3,4-tetrahydro-7-isoquinolinyl)cyclopropyl)-2-naphthalenecarboximidamide, 6-(2-(2-(2-hydroxyethyl)-1-isopropyl-1,2,3,4-tetrahydro-7-isoquinolinyl)cyclopropyl)-2-naphthalenecarboximidamide, 6-(2-(1,2-diisopropyl-1,2,3,4-tetrahydro-7-isoquinolinyl)cyclopropyl)-2-naphthalenecarboximidamide, 6-((1S,2S)-2-(1-isopropyl-3,4-dihydro-7-isoquinolinyl)cyclopropyl)-2-naphthalenecarboximidamide, 6-((1R,2R)-2-(1-isopropyl-3,4-dihydro-7-isoquinolinyl)cyclopropyl)-2-naphthalenecarboximidamide, 6-(2-(4,4-diethyl-1-isopropyl-3,4-dihydro-6-isoquinolinyl)cyclopropyl)-2-naphthalenecarboximidamide, 6-(2-(4,4-diethyl-1-isopropyl-3,4-dihydro-6-isoquinolinyl)cyclopropyl)-2-naphthalenecarboximidamide, 6-(2-(4,4-diethyl-1-isopropyl-2-methyl-1,2,3,4-tetrahydro-6-isoquinolinyl)cyclopropyl)-2-naphthalenecarboximidamide, 6-(2-(1-isopropyl-2-(2,2,2-trifluoroethyl)-1,2,3,4-tetrahydro-7-isoquinolinyl)cyclopropyl)-2-naphthalenecarboximidamide, 8-((1E)-3,3-dimethyl-1-butenyl)-6-(2-(1-isopropyl-3,4-dihydro-7-isoquinolinyl)cyclopropyl)-2-naphthalenecarboximidamide, 8-bromo-6-(2-(1-isopropyl-3,4-dihydro-7-isoquinolinyl)cyclopropyl)-2-naphthalenecarboximidamide, 8-bromo-6-(2-(1-isopropyl-2-methyl-1,2,3,4-tetrahydro-7-isoquinolinyl)cyclopropyl)-2-naphthalenecarboximidamide, 6-(2-(1-isopropyl-2-methyl-1,2,3,4-tetrahydro-7-isoquinolinyl)cyclopropyl)-8-((1E)-3-methyl-1-butenyl)-2-naphthalenecarboximidamide, 6-(2-(1-isopropyl-2-methyl-1,2,3,4-tetrahydro-7-isoquinolinyl)cyclopropyl)-8-((1E)-3-methyl-1,3-butanienyl)-2-naphthalenecarboximidamide, 8-cyclopropyl-6-(2-(1-isopropyl-2-methyl-1,2,3,4-tetrahydro-7-isoquinolinyl)cyclopropyl)-2-naphthalenecarboximidamide, 6-(2-(1-isopropyl-2-methyl-1,2,3,4-tetrahydro-7-isoquinolinyl)cyclopropyl)-8-(2-methoxyphenyl)-2-naphthalenecarboximidamide, 6-(2-(1-isopropyl-2-methyl-1,2,3,4-tetrahydro-7-isoquinolinyl)cyclopropyl)-8-vinyl-2-naphthalenecarboximidamide, methyl 6-(2-(6-(amino(hydroxyimino)methyl)-2-naphthyl)ethenyl)-3,4-dihydro-2(1H)-isoquinolinecarboxylate, 6-(2-(2-acetyl-1,2,3,4-tetrahydro-6-isoquinolinyl)ethenyl-N'-hydroxy-2-naphthalenecarboximidamide, 6-(2-(2-acetyl-1,2,3,4-tetrahydro-6-isoquinolinyl)ethenyl)-2-naphthalenecarboximidamide, N'-hydroxy-6-(2-(1,2,3,4-tetrahydro-6-isoquinolinyl)ethenyl)-2-naphthalenecarboximidamide, 6-(2-(1,2,3,4-tetrahydro-6-isoquinolinyl)cyclopropyl)-2-naphthalenecarboximidamide, 6-(2-(2-acetyl-1,2,3,4-tetrahydro-6-isoquinolinyl)cyclopropyl)-N'-hydroxy-2-naphthalenecarboximidamide, 6-(2-(4-ethyl-1,2,3,4-tetrahydro-6-isoquinolinyl)cyclopropyl)-2-naphthalenecarboximidamide, 6-((2-(2-benzyl-4-ethyl-1,2,3,4-tetrahydro-6-isoquinolinyl)cyclopropyl)-2-naphthalenecarboximidamide, 6-(2-(4-ethyl-1,2,3,4-tetrahydro-6-isoquinolinyl)ethenyl)-2-naphthalenecarboximidamide, 6-(2-(4-ethyl-2-methyl-1,2,3,4-tetrahydro-6-isoquinolinyl)cyclopropyl)-2-naphthalenecarboximidamide, 6-(2-(1-isopropyl-3,4-dihydro-6-isoquinolinyl)cyclopropyl)-2-naphthalenecarboximidamide, 6-(2-(1-isopropyl-3,4-dihydro-6-isoquinolinyl)cyclopropyl)-2-naphthalenecarboximidamide, 6-(2-(4-ethyl-1-isopropyl-3,4-dihydro-6-isoquinolinyl)cyclopropyl)-2-naphthalenecarboximidamide, 6-(2-(4-ethyl-1-isopropyl-3,4-dihydro-6-isoquinolinyl) ethenyl)-2-naphthalenecarboximidamide, 8-bromo-6-(2-(1-cyclohexyl-3,4-dihydro-7-isoquinolinyl) cyclopropyl)-2-naphthalenecarboximidamide, 8-bromo-6-(2-(1-cyclohexyl-2-methyl-1,2,3,4-tetrahydro-7-isoquinolinyl)cyclopropyl)2-naphthalenecarboximidamide, 6-(2-(1-cyclohexyl-3,4-dihydro-7-isoquinolinyl) cyclopropyl)-8-((1E)-3-methyl-1-butenyl)-2-naphthalenecarboximidamide, 6-(2-(1-cyclohexyl-2-methyl-1,2,3,4-tetrahydro-7-isoquinolinyl)cyclopropyl)-8-((1E)-3-methyl-1-butenyl)-2-naphthalenecarboximidamide, and 8-allyl-6-(2-(1-isopropyl-2-methyl-1,2,3,4-tetrahydro-7-isoquinolinyl)cyclopropyl)-2-naphthalenecarboximidamide.

\* \* \* \* \*